(12) United States Patent
Naidu et al.

(10) Patent No.: US 7,902,182 B2
(45) Date of Patent: Mar. 8, 2011

(54) HIV INTEGRASE INHIBITORS

(75) Inventors: B. Narasimhulu Naidu, Durham, CT (US); Margaret E. Sorenson, Meriden, CT (US); Yasutsugu Ueda, Clinton, CT (US); John D. Matiskella, Wallingford, CT (US); Michael A. Walker, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 915 days.

(21) Appl. No.: 11/595,429

(22) Filed: Nov. 10, 2006

(65) Prior Publication Data

US 2007/0111985 A1    May 17, 2007

Related U.S. Application Data

(60) Provisional application No. 60/737,062, filed on Nov. 16, 2005.

(51) Int. Cl.
| | |
|---|---|
| *A61P 31/00* | (2006.01) |
| *A61K 31/55* | (2006.01) |
| *A61K 31/54* | (2006.01) |
| *A61K 31/535* | (2006.01) |
| *C07D 417/00* | (2006.01) |
| *C07D 498/00* | (2006.01) |

(52) U.S. Cl. .................. 514/210.21; 514/217.06; 514/228.5; 514/230.5; 544/61; 544/105

(58) Field of Classification Search ............ 514/210.21, 514/217.06, 228.5, 230.5; 544/61, 105
See application file for complete search history.

(56) References Cited

U.S. PATENT DOCUMENTS

2006/0046985 A1    3/2006 Crescenzi et al.

FOREIGN PATENT DOCUMENTS

| | | |
|---|---|---|
| EP | 1698628 A1 | 9/2006 |
| WO | WO 2005/061490 A1 | 7/2005 |
| WO | WO 2005/061501 A2 | 7/2005 |
| WO | WO 2006/103399 A1 | 10/2006 |
| WO | WO 2006/121831 A2 | 11/2006 |

OTHER PUBLICATIONS

U.S. Appl. No. 11/599,580, filed Nov. 14, 2006, B. Narasimhulu Naidu.
U.S. Appl. No. 60/817,009, filed Jun. 28, 2006, Michael A. Walker, et al.
U.S. Appl. No. 11/511,751, filed Aug. 29, 2006, Jacques Banville, et al.
U.S. Appl. No. 11/138,773, filed May 26, 2005, B. Narasimhulu Naidu, et al.
U.S. Appl. No. 11/138,726, filed May 26, 2005, Jacques Banville, et al.
U.S. Appl. No. 11/126,891, filed May 11, 2005, B. Narasimhulu Naidu, et al.
U.S. Appl. No. 11/288,533, filed Nov. 29, 2005, B. Narasimhulu Naidu, et al.
U.S. Appl. No. 11/110,589, filed Apr. 20, 2005, B. Narasimhulu Naidu.
U.S. Appl. No. 11/273,671, filed Nov. 14, 2005, B. Narasimhulu Naidu.

*Primary Examiner*—Brenda L Coleman
(74) *Attorney, Agent, or Firm*—James Epperson

(57) ABSTRACT

The invention encompasses a series bicyclic pyrimidinone compounds of Formula I which inhibit HIV integrase and prevent viral integration into human DNA. This action makes the compounds useful for treating HIV infection and AIDS. The invention also encompasses pharmaceutical compositions and methods for treating those infected with HIV.

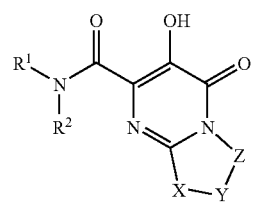

9 Claims, No Drawings

HIV INTEGRASE INHIBITORS

CROSS-REFERENCE TO RELATED APPLICATIONS

This application claims the benefit of U.S. Provisional Application Ser. No. 60/737,062 filed Nov. 16, 2005.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. N. Engl. J. Med. 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. JAMA 2000, 283, 381-390). Clearly there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. Science 2000, 287, 646). And recently, HIV integrase inhibitors have been accepted into clinical trials for treating AIDS and HIV infection (Neamati Expert. Opin. Ther. Patents 2002, 12, 709, Pais and Burke Drugs Fut. 2002, 27, 1101).

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention are compounds of Formula I

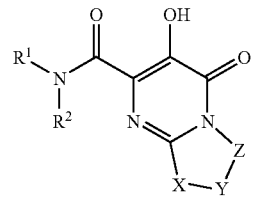

$R^1$ is $(Ar^1)$alkyl;
$R^2$ is hydrogen, alkyl, hydroxy, or alkoxy;
$R^3$ is $SO_2N(R^6)(R^7)$;
$R^4$ is hydrogen, halo, hydroxy, cyano, alkyl, alkoxy, haloalkyl, or haloalkoxy;
$R^5$ is hydrogen, halo, hydroxy, cyano, alkyl, alkoxy, haloalkyl, or haloalkoxy;
$R^6$ and $R^7$ taken together with the nitrogen to which they are attached is azetidinyl,
$(R^8)$-azetidinyl, pyrrolidinyl, $(R^8)$-pyrrolidinyl, piperidinyl, $(R^8)$-piperidinyl, dialkylpiperidinyl, trialkylpiperidinyl piperazinyl, 4-$(R^9)$-piperazinyl, dialkylpiperazinyl, dialkyl-4-$(R^9)$-piperazinyl, homopiperidinyl, morpholinyl, thiomorpholinyl,

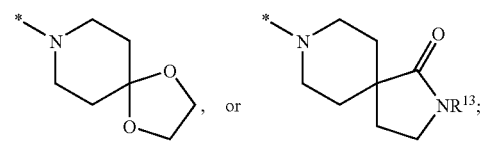

$R^8$ is hydroxy, alkyl, hydroxy, alkoxy, amino, alkylamino, dialklyamino, alkylCONH, alkylCON(alkyl), (methylthio)tetrahydrofiranyl, (amino)tetrahydrofiiranyl, (alkylamino)tetrahydrofuranyl, (dialkylamino)tetrahydrofuranyl, azetidinyl, pyrrolidinyl, piperidinyl, piperazinyl, homopiperidinyl, morpholinyl, (azetidinyl)alkyl, (pyrrolidinyl)alkyl,
(piperidinyl)alkyl, (piperazinyl)alkyl, (homopiperidinyl) alkyl, or (morpholinyl)alkyl;
$R^9$ is alkyl, (cycloalkyl)alkyl, $SO_2R^{10}$, or $COR^{11}$;
$R^{10}$ is hydrogen, alkyl, amino, alkylamino, dialkylamino, azetidinyl, pyrrolidinyl, piperidinyl, hydroxypiperidinyl, piperizinyl, 4-(alkyl)piperizinyl, morpholinyl, or thiomorpholinyl;
$R^{11}$ hydrogen, alkyl, hydroxy, alkoxy, amino, alkylamino, dialkylamino, azetidinyl, pyrrolidinyl, piperidinyl, hydroxypiperidinyl, piperizinyl, 4-(alkyl)piperizinyl, morpholinyl, or thiomorpholinyl;
$R^{12}$ is hydrogen or alkyl;

or two R$^{12}$'s taken together are CH$_2$CH$_2$, CH$_2$CH$_2$CH$_2$, CH$_2$CH$_2$CH$_2$CH$_2$, CH$_2$CH$_2$CH$_2$CH$_2$CH$_2$, CH$_2$CH$_2$CH$_2$CH$_2$CH$_2$CH$_2$, OCH$_2$CH$_2$, CH$_2$OCH$_2$, OCH$_2$CH$_2$CH$_2$, CH$_2$OCH$_2$CH$_2$, OCH$_2$CH$_2$CH$_2$CH$_2$, CH$_2$OCH$_2$CH$_2$CH$_2$, CH$_2$CH$_2$OCH$_2$CH$_2$, OCH$_2$CH$_2$CH$_2$CH$_2$CH$_2$, CH$_2$OCH$_2$CH$_2$CH$_2$CH$_2$, CH$_2$CH$_2$OCH$_2$CH$_2$CH$_2$, N(R$^{13}$)CH$_2$CH$_2$, CH$_2$N(R$^{13}$)CH$_2$, N(R$^{13}$)CH$_2$CH$_2$CH$_2$, CH$_2$N(R$^{13}$)CH$_2$CH$_2$, N(R$^{13}$)CH$_2$CH$_2$CH$_2$CH$_2$, CH$_2$N(R$^{13}$)CH$_2$CH$_2$CH$_2$, CH$_2$CH$_2$N(R$^{13}$)CH$_2$CH$_2$, N(R$^{13}$)CH$_2$CH$_2$CH$_2$CH$_2$CH$_2$, CH$_2$N(R$^{13}$)CH$_2$CH$_2$CH$_2$CH$_2$, or CH$_2$CH$_2$N(R$^{13}$)CH$_2$CH$_2$CH$_2$, provided that the two R$^{12}$'s are attached to a common carbon atom;

R$^{13}$ is hydrogen or alkyl;

R$^{14}$ and R$^{15}$ taken together are C$_{3-5}$alkylene;

Ar$^1$ is

Ar$^2$ is phenyl or pyridinyl substituted with 0-2 substituents selected from halo, alkyl, and alkoxy; and X-Y-Z is C(R$^{12}$)$_2$OC(R$^{12}$)$_2$, C(R$^{12}$)$_2$OC(R$^{12}$)$_2$C(R$^{12}$)$_2$, C(R$^{12}$)$_2$OC(R$^{12}$)$_2$C(R$^{12}$)$_2$C(R$^{12}$)$_2$, C(R$^{12}$)$_2$CH$_2$CH$_2$, C(R$^{12}$)$_2$CH$_2$CH$_2$CH$_2$, C(R$^{12}$)$_2$CH$_2$CH$_2$CH$_2$CH$_2$, C(Ar$^2$)=CHCH$_2$, C(Ar$^2$)=CHCH$_2$CH$_2$, C(Ar$^2$)=CHCH$_2$CH$_2$CH$_2$, (R$^{12}$)$_2$N(R$^{13}$)C(R$^{12}$)$_2$, C(R$^{12}$)$_2$N(R$^{13}$)C(R$^{12}$)$_2$C(R$^{12}$)$_2$, C(R$^{12}$)$_2$N(R$^{13}$)C(R$^{12}$)$_2$C(R$^{12}$)$_2$C(R$^{12}$)$_2$, N(R$^{12}$)COC(R$^{12}$)$_2$, N(R$^{12}$)COC(R$^{12}$)$_2$C(R$^{12}$)$_2$, N(R$^{12}$)COC(R$^{12}$)$_2$C(R$^{12}$)$_2$C(R$^{12}$)$_2$, N(R$^{12}$)SO$_2$C(R$^{12}$)$_2$, N(R$^{12}$)SO$_2$C(R$^{12}$)$_2$C(R$^{12}$)$_2$, N(R$^{12}$)SO$_2$C(R$^{12}$)$_2$C(R$^{12}$)$_2$C(R$^{12}$)$_2$, N(R$^{12}$)N(R$^{12}$)COC(R$^{12}$)$_2$, N(R$^{12}$)N(R$^{12}$)COC(R$^{12}$)$_2$C(R$^{12}$)$_2$, N(R$^{14}$)N(R$^{15}$)COC(R$^{12}$)$_2$, N(R$^{14}$)N(R$^{15}$)COC(R$^{12}$)$_2$C(R$^{12}$)$_2$, C(R$^{12}$)$_2$N(R$^{12}$)CO, C(R$^{12}$)$_2$N(R$^{12}$)COC(R$^{12}$)$_2$, C(R$^{12}$)$_2$N(R$^{12}$)COC(R$^{12}$)$_2$C(R$^{12}$)$_2$, C(R$^{14}$)$_2$N(R$^{15}$)CO, C(R$^{14}$)$_2$N(R$^{15}$)COC(R$^{12}$)$_2$, C(R$^{14}$)$_2$N(R$^{15}$)COC(R$^{12}$)$_2$C(R$^{12}$)$_2$, SC(R$^{12}$)$_2$C(R$^{12}$)$_2$, SC(R$^{12}$)$_2$C(R$^{12}$)$_2$C(R$^{12}$)$_2$, or SC(R$^{12}$)$_2$C(R$^{12}$)$_2$C(R$^{12}$)$_2$C(R$^{12}$)$_2$;

or a pharmaceutically acceptable salt thereof.

Another aspect of the invention are compounds of Formula I

R$^1$ is (Ar$^1$)alkyl;
R$^2$ is hydrogen, alkyl, hydroxy, or alkoxy;
R$^3$ is SO$_2$N(R$^6$)(R$^7$);
R$^4$ is hydrogen, halo, hydroxy, cyano, alkyl, alkoxy, haloalkyl, or haloalkoxy;
R$^5$ is hydrogen, halo, hydroxy, cyano, alkyl, alkoxy, haloalkyl, or haloalkoxy;
R$^6$ and R$^7$ taken together with the nitrogen to which they are attached is azetidinyl, pyrrolidinyl, piperidinyl, (R$^8$)-piperidinyl, piperazinyl, 4-(R$^9$)-piperazinyl, homopiperidinyl, morpholinyl, or thiomorpholinyl;

R$^8$ is hydroxy or alkyl;

R$^9$ is alkyl, (cycloalkyl)alkyl, SO$_2$R$^{10}$, or COR$^{11}$;

R$^{10}$ is hydrogen, alkyl, amino, alkylamino, dialkylamino, azetidinyl, pyrrolidinyl, piperidinyl, hydroxypiperidinyl, piperizinyl, 4-(alkyl)piperizinyl, morpholinyl, or thiomorpholinyl;

R$^{11}$ hydrogen, alkyl, hydroxy, alkoxy, amino, alkylamino, dialkylamino, azetidinyl, pyrrolidinyl, piperidinyl, hydroxypiperidinyl, piperizinyl, 4-(alkyl)piperizinyl, morpholinyl, or thiomorpholinyl;

R$^{12}$ is hydrogen or alkyl;

or two R$^{12}$'s taken together are CH$_2$CH$_2$, CH$_2$CH$_2$CH$_2$, CH$_2$CH$_2$CH$_2$CH$_2$, CH$_2$CH$_2$CH$_2$CH$_2$CH$_2$, CH$_2$CH$_2$CH$_2$CH$_2$CH$_2$CH$_2$, OCH$_2$CH$_2$, CH$_2$OCH$_2$, OCH$_2$CH$_2$CH$_2$, CH$_2$OCH$_2$CH$_2$, OCH$_2$CH$_2$CH$_2$CH$_2$, CH$_2$OCH$_2$CH$_2$CH$_2$, CH$_2$CH$_2$OCH$_2$CH$_2$, OCH$_2$CH$_2$CH$_2$CH$_2$CH$_2$, CH$_2$OCH$_2$CH$_2$CH$_2$CH$_2$, CH$_2$CH$_2$OCH$_2$CH$_2$CH$_2$, N(R$^{13}$)CH$_2$CH$_2$, CH$_2$N(R$^{13}$)CH$_2$, N(R$^{13}$)CH$_2$CH$_2$CH$_2$, CH$_2$N(R$^{13}$)CH$_2$CH$_2$, N(R$^{13}$)CH$_2$CH$_2$CH$_2$CH$_2$, CH$_2$N(R$^{13}$)CH$_2$CH$_2$CH$_2$, CH$_2$CH$_2$N(R$^{13}$)CH$_2$CH$_2$, N(R$^{13}$)CH$_2$CH$_2$CH$_2$CH$_2$CH$_2$, CH$_2$N(R$^{13}$)CH$_2$CH$_2$CH$_2$CH$_2$, or CH$_2$CH$_2$N(R$^{13}$)CH$_2$CH$_2$CH$_2$, provided that the two R$^{12}$'s are attached to a common carbon atom;

R$^{13}$ is hydrogen or alkyl;

R$^{14}$ and R$^{15}$ taken together are C$_{3-5}$alkylene;

Ar$^1$ is

Ar$^2$ is phenyl or pyridinyl substituted with 0-2 substituents selected from halo, alkyl, and alkoxy; and X—Y—Z is C(R$^{12}$)$_2$OC(R$^{12}$)$_2$, C(R$^{12}$)$_2$OC(R$^{12}$)$_2$C(R$^{12}$)$_2$, C(R$^{12}$)$_2$OC(R$^{12}$)$_2$C(R$^{12}$)$_2$C(R$^{12}$)$_2$, C(R$^{12}$)$_2$CH$_2$CH$_2$, C(R$^{12}$)$_2$CH$_2$CH$_2$CH$_2$, C(R$^{12}$)$_2$CH$_2$CH$_2$CH$_2$CH$_2$, C(Ar$^2$)=CHCH$_2$, C(Ar$^2$)=CHCH$_2$CH$_2$, C(Ar$^2$)=CHCH$_2$CH$_2$CH$_2$, (R$^{12}$)$_2$N(R$^{13}$)C(R$^{12}$)$_2$, C(R$^{12}$)$_2$N(R$^{13}$)C(R$^{12}$)$_2$C(R$^{12}$)$_2$, C(R$^{12}$)$_2$N(R$^{13}$)C(R$^{12}$)$_2$C(R$^{12}$)$_2$C(R$^{12}$)$_2$, N(R$^{12}$)COC(R$^{12}$)$_2$, N(R$^{12}$)COC(R$^{12}$)$_2$C(R$^{12}$)$_2$, N(R$^{12}$)COC(R$^{12}$)$_2$C(R$^{12}$)$_2$C(R$^{12}$)$_2$, N(R$^{12}$)SO$_2$C(R$^{12}$)$_2$, N(R$^{12}$)SO$_2$C(R$^{12}$)$_2$C(R$^{12}$)$_2$, N(R$^{12}$)SO$_2$C(R$^{12}$)$_2$C(R$^{12}$)$_2$C(R$^{12}$)$_2$, N(R$^{12}$)N(R$^{12}$)COC(R$^{12}$)$_2$, N(R$^{12}$)N(R$^{12}$)COC(R$^{12}$)$_2$C(R$^{12}$)$_2$, N(R$^{14}$)N(R$^{15}$)COC(R$^{12}$)$_2$, N(R$^{14}$)N(R$^{15}$)COC(R$^{12}$)$_2$C(R$^{12}$)$_2$, C(R$^{12}$)$_2$N(R$^{12}$)CO, C(R$^{12}$)$_2$N(R$^{12}$)COC(R$^{12}$)$_2$, C(R$^{12}$)$_2$N(R$^{12}$)COC(R$^{12}$)$_2$C(R$^{12}$)$_2$, C(R$^{14}$)$_2$N(R$^{15}$)CO, C(R$^{14}$)$_2$N(R$^{15}$)COC(R$^{12}$)$_2$, C(R$^{14}$)$_2$N(R$^{15}$)COC(R$^{12}$)$_2$C(R$^{12}$)$_2$, SC(R$^{12}$)$_2$C(R$^{12}$)$_2$, SC(R$^{12}$)$_2$C(R$^{12}$)$_2$C(R$^{12}$)$_2$, or SC(R$^2$)$_2$C(R$^{12}$)$_2$C(R$^{12}$)$_2$C(R$^{12}$)$_2$;

or a pharmaceutically acceptable salt thereof.

Another aspect of the invention is a compound of Formula I where $R^1$ is

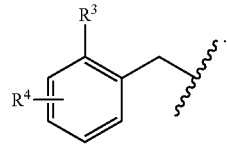

Another aspect of the invention is a compound of Formula I where $R^4$ is hydrogen or halo.

Another aspect of the invention is a compound of Formula I where $R^2$ is hydrogen.

Another aspect of the invention is a compound of Formula I where X—Y—Z is $C(R^{12})_2OC(R^{12})_2$, $C(R^{12})_2OC(R^{12})_2C(R^{12})_2$, or $C(R^{12})_2OC(R^{12})_2C(R^{12})_2C(R^{12})_2$.

Another aspect of the invention is a compound of Formula I where X—Y—Z is $C(R^{12})_2CH_2CH_2$, $C(R^{12})_2CH_2CH_2CH_2$, or $C(R^{12})_2CH_2CH_2CH_2CH_2$.

Another aspect of the invention is a compound of Formula I where X—Y—Z is $C(Ar^2)=CHCH_2$, $C(Ar^2)=CHCH_2CH_2$, or $C(Ar^2)=CHCH_2CH_2CH_2$.

Another aspect of the invention is a compound of Formula I where X—Y—Z is $(R^{12})_2N(R^{13})C(R^{12})_2$, $C(R^{12})_2N(R^{13})C(R^{12})_2C(R^{12})_2$, or $C(R^{12})_2N(R^{13})C(R^{12})_2C(R^{12})_2C(R^{12})_2$.

Another aspect of the invention is a compound of Formula I where X—Y—Z is $N(R^{12})COC(R^{12})_2$, $N(R^{12})COC(R^{12})_2C(R^{12})_2$, $N(R^{12})COC(R^{12})_2C(R^{12})_2C(R^{12})_2$, $N(R^{12})SO_2C(R^{12})_2$, $N(R^{12})SO_2C(R^{12})_2C(R^{12})_2$, $N(R^{12})SO_2C(R^{12})_2C(R^{12})_2C(R^{12})_2$, $N(R^{12})N(R^{12})COC(R^{12})_2$, $N(R^{12})N(R^{12})COC(R^{12})_2C(R^{12})_2$, $N(R^{14})N(R^{15})COC(R^{12})_2$, $N(R^{14})N(R^{15})COC(R^{12})_2C(R^{12})_2$, $C(R^{12})_2N(R^{12})CO$, $C(R^{12})_2N(R^{12})COC(R^{12})_2$, $C(R^{12})_2N(R^{12})COC(R^{12})_2C(R^{12})_2$, $C(R^{14})_2N(R^{15})CO$, $C(R^{14})_2N(R^{15})COC(R^{12})_2$, or $C(R^{14})_2N(R^{15})COC(R^{12})_2C(R^{12})_2$.

Another aspect of the invention is a compound of Formula I where X—Y—Z is $SC(R^{12})_2C(R^{12})_2$, $SC(R^{12})_2C(R^{12})_2C(R^{12})_2$, or $SC(R^{12})_2C(R^{12})_2C(R^{12})_2C(R^{12})_2$.

Another aspect of the invention is a compound of selected from the group consisting of

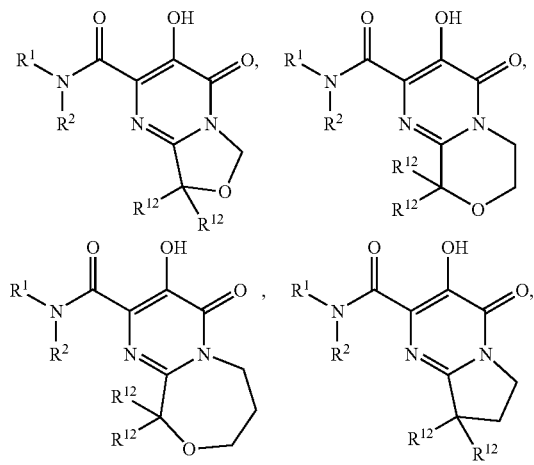

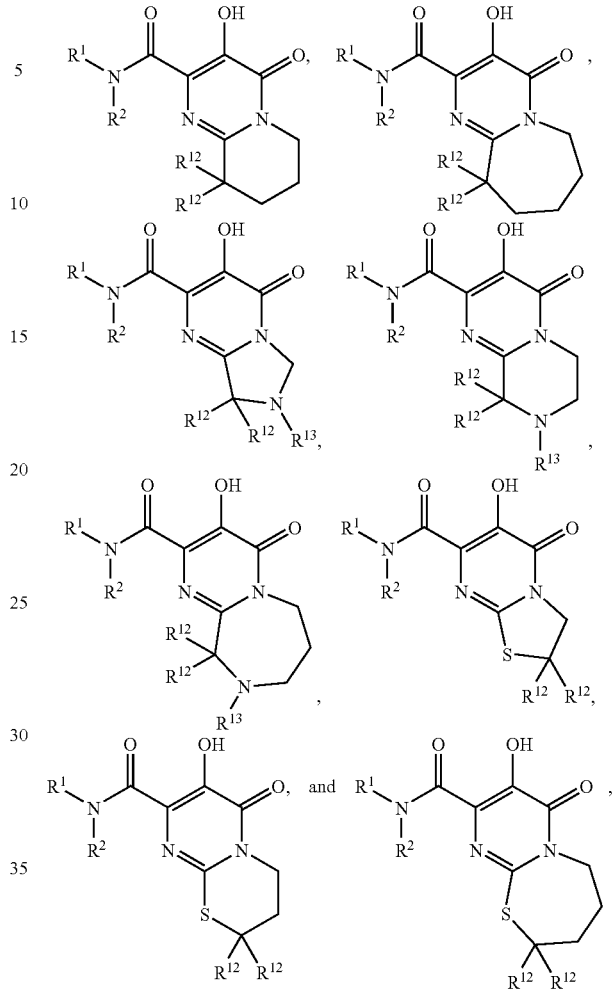

and where $R^1$ is $(Ar^1)$alkyl;

$R^2$ is hydrogen, alkyl, hydroxy, or alkoxy;

$R^3$ is $SO_2N(R^6)(R^7)$;

$R^4$ is hydrogen, halo, hydroxy, cyano, alkyl, alkoxy, haloalkyl, or haloalkoxy;

$R^5$ is hydrogen, halo, hydroxy, cyano, alkyl, alkoxy, haloalkyl, or haloalkoxy;

$R^6$ and $R^7$ taken together with the nitrogen to which they are attached is azetidinyl, pyrrolidinyl, piperidinyl, $(R^8)$-piperidinyl, piperazinyl, 4-$(R^9)$-piperazinyl, homopiperidinyl, morpholinyl, or thiomorpholinyl;

$R^8$ is hydroxy or alkyl;

$R^9$ is alkyl, (cycloalkyl)alkyl, $SO_2R^{10}$, or $COR^{11}$;

$R^{10}$ is hydrogen, alkyl, amino, alkylamino, dialkylamino, azetidinyl, pyrrolidinyl, piperidinyl, hydroxypiperidinyl, piperizinyl, 4-(alkyl)piperizinyl, morpholinyl, or thiomorpholinyl;

$R^{11}$ hydrogen, alkyl, hydroxy, alkoxy, amino, alkylamino, dialkylamino, azetidinyl, pyrrolidinyl, piperidinyl, hydroxypiperidinyl, piperizinyl, 4-(alkyl)piperizinyl, morpholinyl, or thiomorpholinyl;

$R^{12}$ is hydrogen or alkyl;

or two $R^{12}$'s taken together are $CH_2CH_2$, $CH_2CH_2CH_2$, $CH_2CH_2CH_2CH_2$, $CH_2CH_2CH_2CH_2CH_2$, CH$_2$CH$_2$CH$_2$CH$_2$CH$_2$CH$_2$, OCH$_2$CH$_2$, CH$_2$OCH$_2$, OCH$_2$CH$_2$CH$_2$, CH$_2$OCH$_2$CH$_2$, OCH$_2$CH$_2$CH$_2$CH$_2$, CH$_2$OCH$_2$CH$_2$CH$_2$, CH$_2$CH$_2$OCH$_2$CH$_2$, OCH$_2$CH$_2$CH$_2$CH$_2$, CH$_2$OCH$_2$CH$_2$CH$_2$CH$_2$, CH$_2$CH$_2$OCH$_2$CH$_2$CH$_2$, N(R$^{13}$)CH$_2$CH$_2$, CH$_2$N(R$^{13}$)CH$_2$, N(R$^{13}$)CH$_2$CH$_2$CH$_2$, CH$_2$N(R$^{13}$)CH$_2$CH$_2$, N(R$^{13}$)CH$_2$CH$_2$CH$_2$CH$_2$, CH$_2$N(R$^{13}$)CH$_2$CH$_2$CH$_2$, CH$_2$CH$_2$N(R$^{13}$)CH$_2$CH$_2$, N(R$^{13}$)CH$_2$CH$_2$CH$_2$CH$_2$CH$_2$, CH$_2$N(R$^{13}$)CH$_2$CH$_2$CH$_2$CH$_2$, or CH$_2$CH$_2$N(R$^{13}$)CH$_2$CH$_2$CH$_2$, provided that the two R$^{12}$'s are attached to a common carbon atom;

R$^{13}$ is hydrogen or alkyl;

R$^{14}$ and R$^{15}$ taken together are C$_{3-5}$alkylene; and

Ar$^1$ is

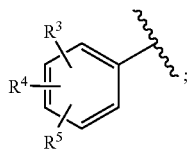

or a pharmaceutically acceptable salt thereof.

For a compound of Formula I, any scope of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, Ar$^1$, Ar$^2$, Ar$^3$, and X-Y-Z can be used independently with any scope of any other substituent. Each instance of a variable is independent of another instance.

Unless specified otherwise, these terms have the following meanings. "Alkyl" means a straight or branched alkyl group composed of 1 to 6 carbons. "Alkenyl" means a straight or branched alkenyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

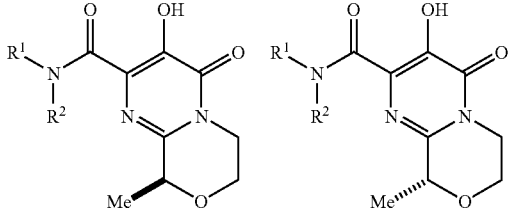

The invention includes all tautomeric forms of the compounds. An example of a tautomeric pair is shown below.

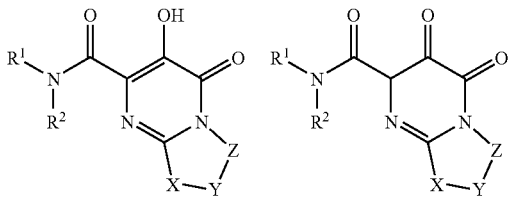

Synthetic Methods

The compounds of this invention can be made by various methods known in the art including those of the following schemes and in the specific embodiments section. The variables shown in the synthetic schemes are distinct from and should not be confused with the variables in the claims or the rest of the specification. The variables in the schemes are meant only to illustrate how to make some of the compounds of this invention.

Some compounds can be synthesized from an appropriately substituted heterocycle I-1 according to Scheme I, where R$_a$ and P can serve as protecting groups (see Greene, T. W. and Wutz, P. G. M. Protective Groups in Organic Synthesis, Second Edition, 1991, John Wiley and Sons, New York). When P is benzyl or substituted benzyl it can be removed by hydrogenolysis (H$_2$—Pd/C) or acid hydrolysis (trifluoroacetic acid) to yield intermediate I-2. I-2 can be transaminated to I-4 by reaction with amine I-3. In a number of cases this reaction can be carried out by heating I-3 and I-2 together in the presence of base. Alternatively, standard amide coupling reagents can be used to effect the formation of the amide bond. When R$_a$ is a lower alkyl group, R$_a$ can be removed under ester hydrolysis conditions, such as treatment with NaOH, LiOH, or KOH to deliver the corresponding carboxylic acid I-5. Alternatively, R$_a$ can be removed by nucleophilic displacement using NaI. When R$_a$ is benzyl and substituted benzyl, R$_a$ can be removed by hydrogenolysis. Intermediate I-5 can be coupled using amide bond forming reagents such as BOP, DCC, EDCI, PyBrop, PyBop or other reagents (see March, J. Advanced Organic Chemistry, Fourth Edition 1992 John Wiley & Sons, New York). The resulting intermediate I-6 can be deprotected as described for intermediate I-1.

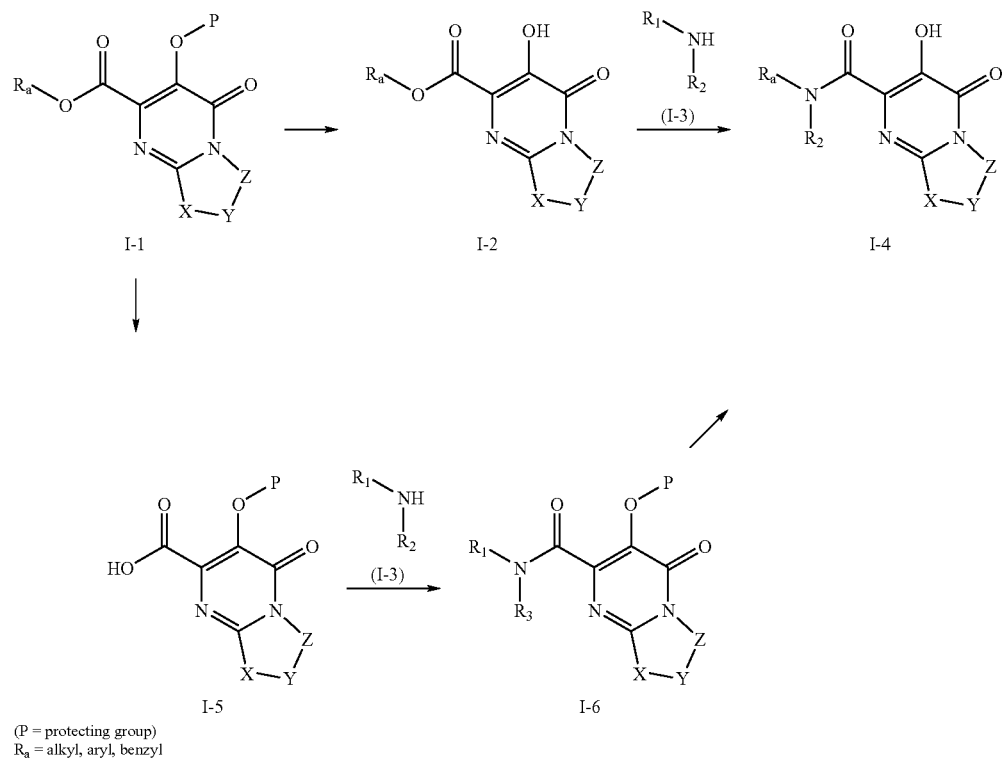

(P = protecting group)
$R_a$ = alkyl, aryl, benzyl

In Scheme II, intermediate II-3 can be prepared using methods similar to those described in Sunderland, J. S.; Botta, M.; Aime, S.; Raymond, K. N. Inorg. Chem. (2001), 40, 6756-6756, where II-1 and II-2 are condensed, to provide intermediate II-3. This reaction is usually conducted in the presence of a base such as sodium hydride (NaH), sodium ethoxide (EtONa) or lithium hexamethyldisilazide (LiHMDS). Using the methods described in the reference, II-3 can be condensed with an appropriately substituted amidine II-4 to form II-5. Substituent B can be a leaving group, such as -halo (Cl, Br or I) or can be converted to a leaving group under appropriate conditions such as by forming the corresponding methylsulfonate ester. When substituent B is a methyl sulphide group it can be treated with iodomethane to form a dimethylsulfonium intermediate which is activated towards nucleophilic attack to effect ring closure.

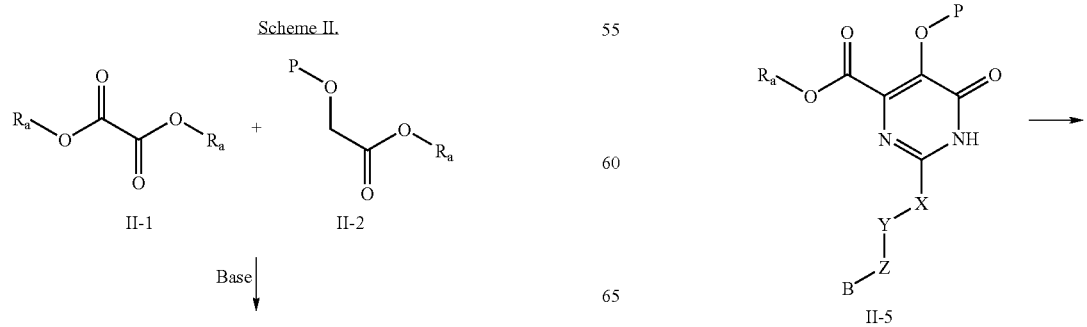

-continued

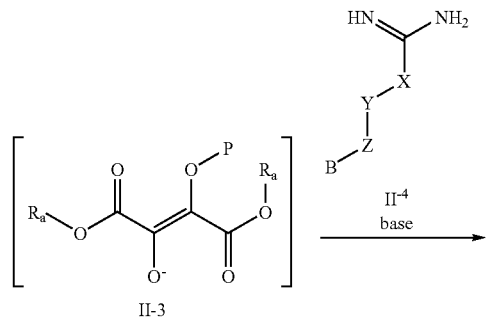

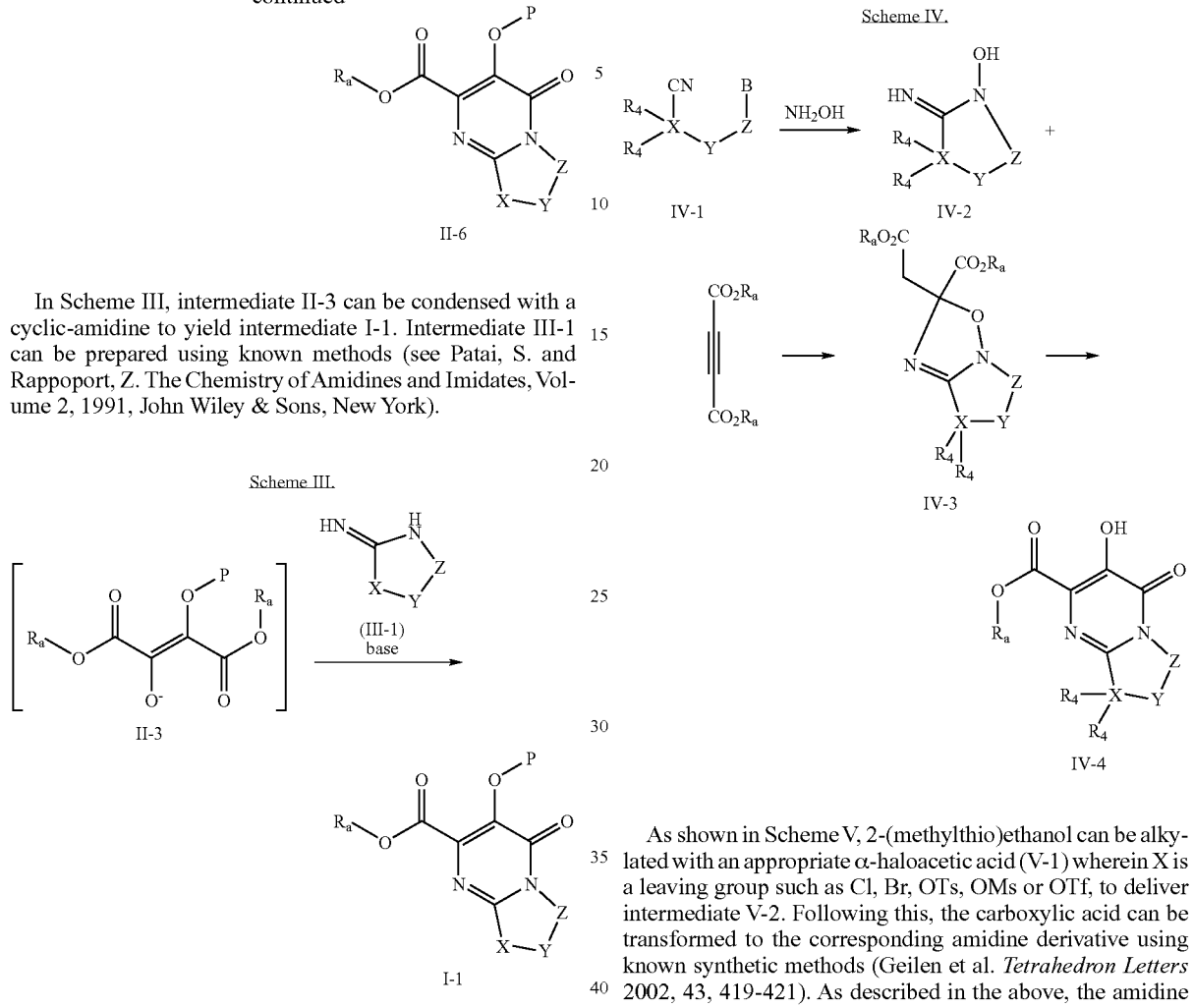

In Scheme III, intermediate II-3 can be condensed with a cyclic-amidine to yield intermediate I-1. Intermediate III-1 can be prepared using known methods (see Patai, S. and Rappoport, Z. The Chemistry of Amidines and Imidates, Volume 2, 1991, John Wiley & Sons, New York).

In Scheme IV, nitrile IV-1, possessing a potential leaving group B, can be reacted with hydroxylamine to form intermediate IV-2. This intermediate can be reacted with a suitably protected alkyne to form IV-3 which can rearrange to from intermediate IV-4 according to literature methods (Culbertson, T. P. *Journal of Heterocyclic Chemistry,* 1979, 16, 1423-1424).

As shown in Scheme V, 2-(methylthio)ethanol can be alkylated with an appropriate α-haloacetic acid (V-1) wherein X is a leaving group such as Cl, Br, OTs, OMs or OTf, to deliver intermediate V-2. Following this, the carboxylic acid can be transformed to the corresponding amidine derivative using known synthetic methods (Geilen et al. *Tetrahedron Letters* 2002, 43, 419-421). As described in the above, the amidine can further be reacted with intermediate V-5, in the presence of a base (for example, sodium ethoxide) affording intermediate V-6. Methylation of the sulphide ether can be accomplished by treating V-6 with iodomethane and the resulting sulfonium derivative (V-7) treated with base to form the bicyclic template V-8. This intermediate can be used in the synthesis of final compounds using methods described in Scheme I.

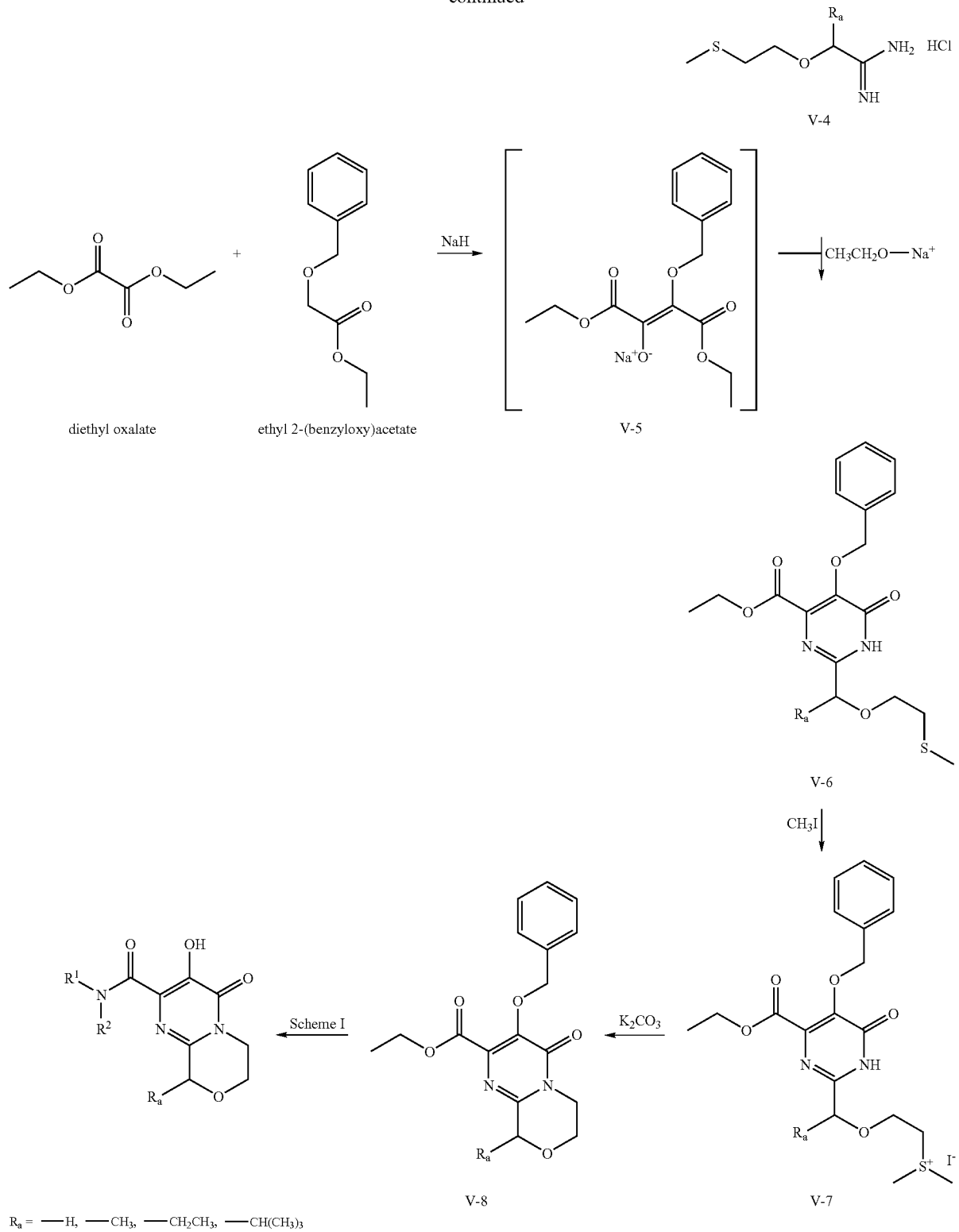

In Scheme VI, 3-methylthiopropanal is converted to dioxolane VI-1 using well known chemistry. Treatment with trimethylsilylcyanide (TMSCN), in the presence of zinc iodide ($ZnI_2$) produces intermediate VI-2. Reaction with ammonia provides amidine VI-3 which is used in the synthesis of pyrimidinone VI-4 according to the methods described in the previous schemes. Subsequent treatment with $CH_3SO_2Cl$ and triethylamine ($Et_3N$) results in the corresponding bicyclic intermediate VI-5. Completion of the synthesis can be carried out as illustrated in Scheme I.

Another method is illustrated in Scheme VII. This synthetic path begins with an appropriately substituted ketone which can be transformed to the corresponding nitrile intermediate VII-1. This in turn can be reacted with 2-chloroethanol to produce compound VII-2, which can be reacted with hydroxylamine and an acetylene dicarboxylate ester to yield intermediate VII-4. Heating of the intermediate can yield intermediate VII-5. Synthesis of the corresponding amide derivatives can be accomplished according to Scheme I.

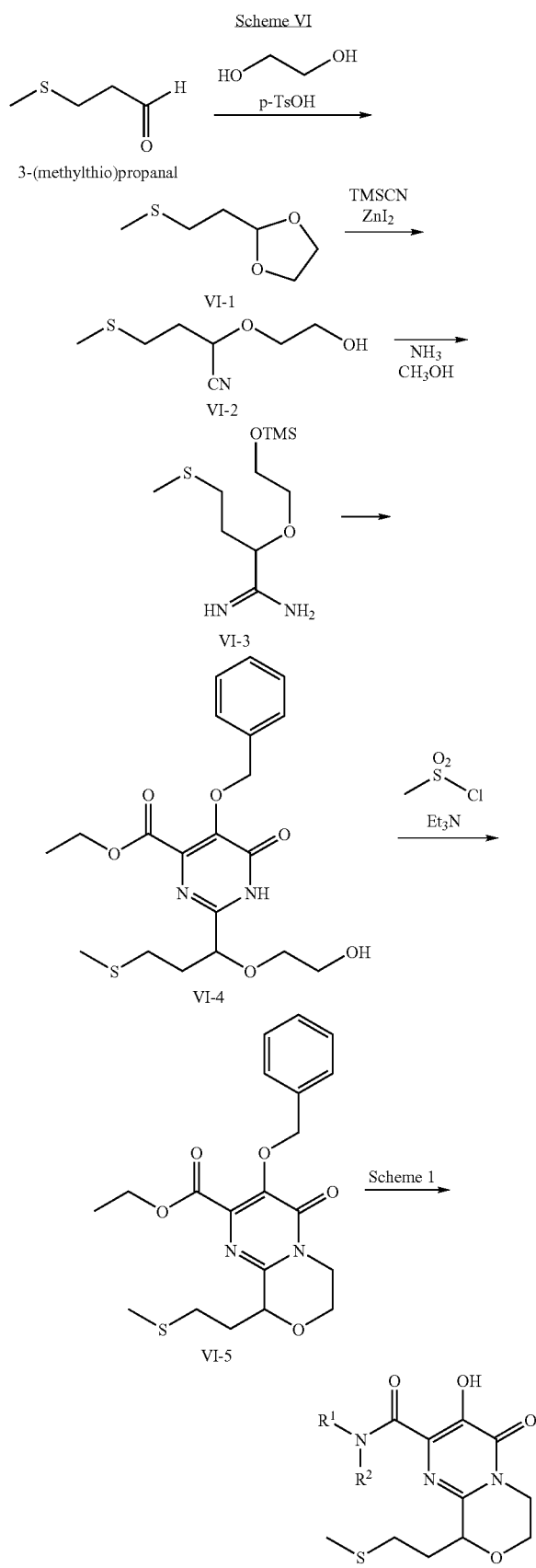

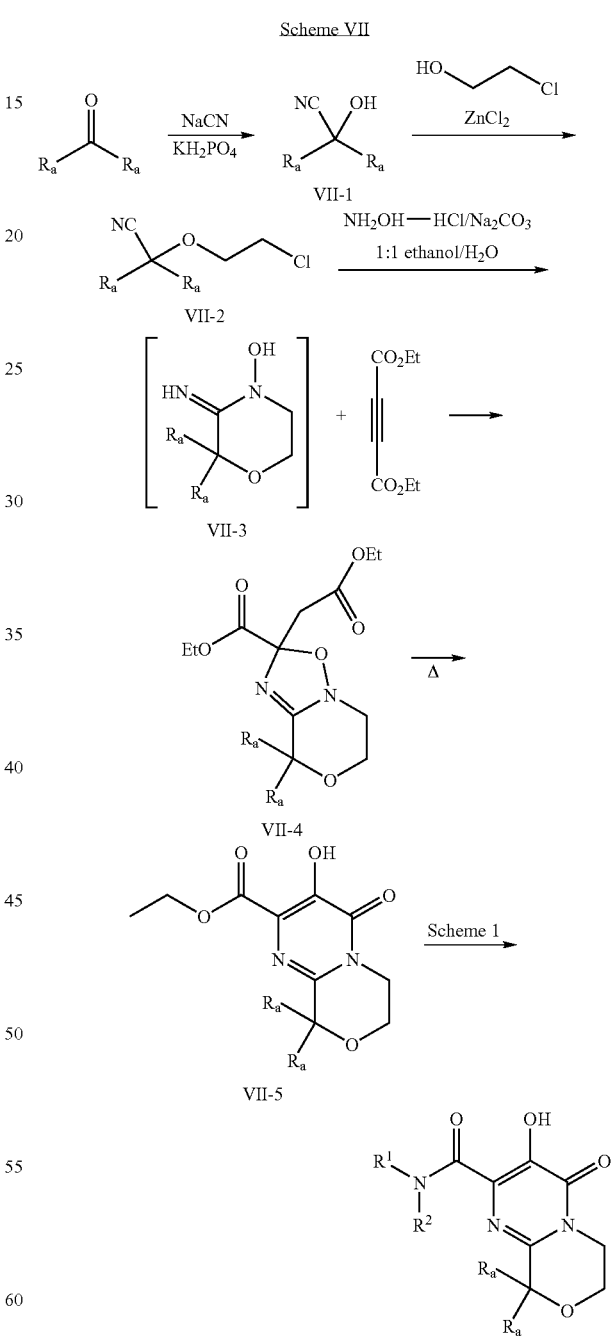

In Scheme VIII, benzylation of the hydroxyl group of VII-5, as a means of functional group protection, can be achieved using benzyl bromide under basic conditions (for example, $K_2CO_3$ or NaH). Saponification of the ester group of VIII-1 can provide VIII-2 which can be coupled with appropriately substituted amines (R¹R²NH) using well known amide bond forming reagents, such as benzotriazole-1-yloxy-tris-pyrrolidino-phosphonium hexafluorophosphate (PyBOP) or O-(7-azabenzotriazol-1-yl)-N,N,N',N'-tetramethyluronium hexafluorophosphate (HATU). Alternatively, the corresponding acid chloride can be formed, by treatment with oxalyl chloride, and reacted with an appropriate amine to form the amide bond. Removal of the benzyl group can be accomplished under a variety of conditions including treatment with $CF_3CO_2H$ or $H_2$ (Pd—C).

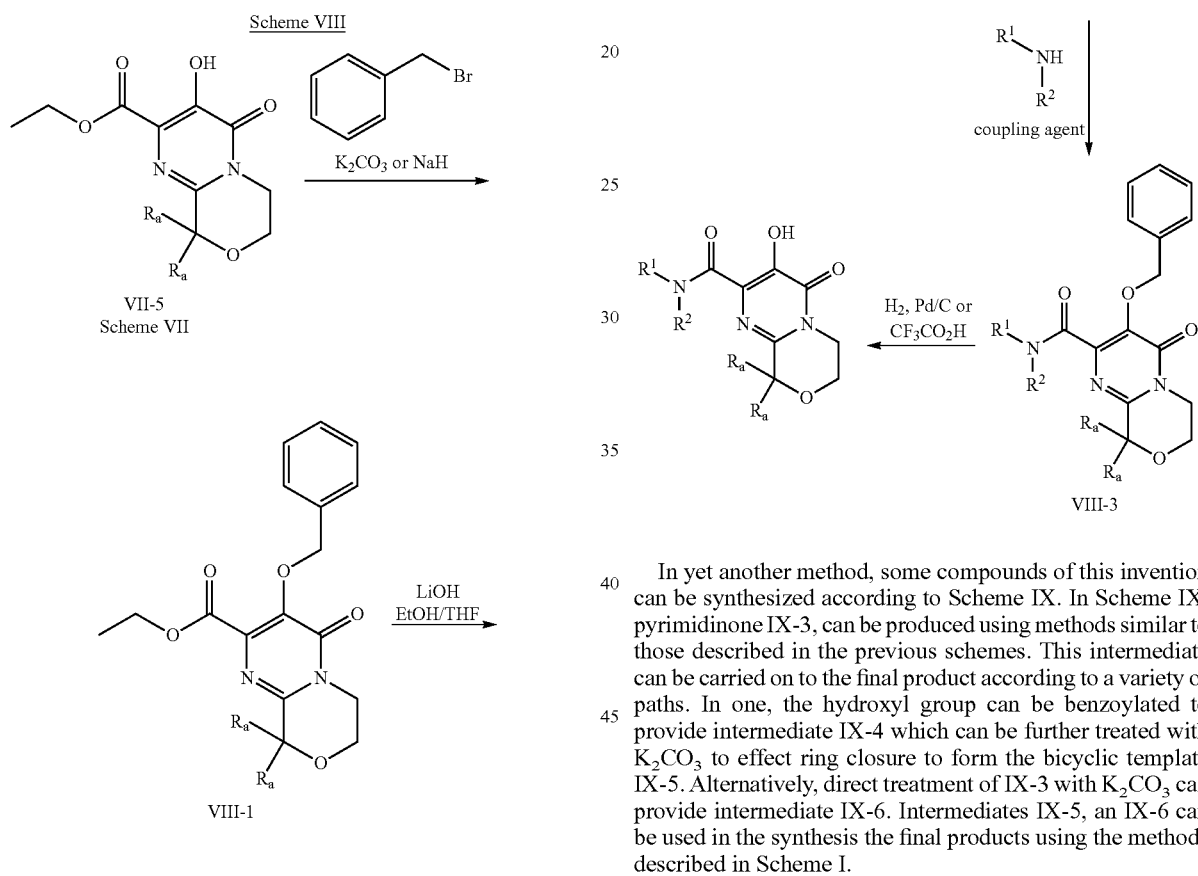

In yet another method, some compounds of this invention can be synthesized according to Scheme IX. In Scheme IX, pyrimidinone IX-3, can be produced using methods similar to those described in the previous schemes. This intermediate can be carried on to the final product according to a variety of paths. In one, the hydroxyl group can be benzoylated to provide intermediate IX-4 which can be further treated with $K_2CO_3$ to effect ring closure to form the bicyclic template IX-5. Alternatively, direct treatment of IX-3 with $K_2CO_3$ can provide intermediate IX-6. Intermediates IX-5, an IX-6 can be used in the synthesis the final products using the methods described in Scheme I.

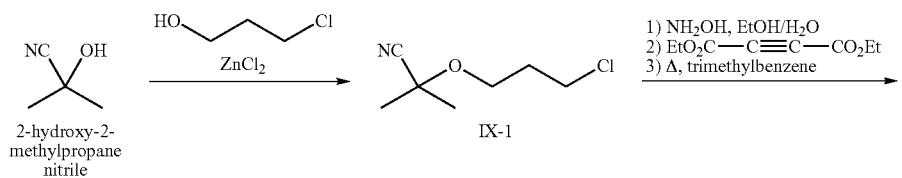

-continued
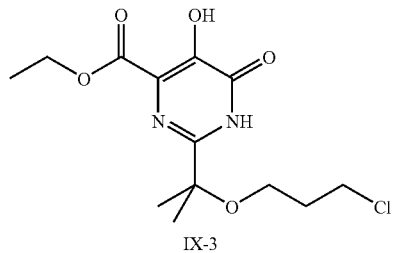
IX-3
benzoic anhydride, pyridine ↙     ↓ K₂CO₃, DMF
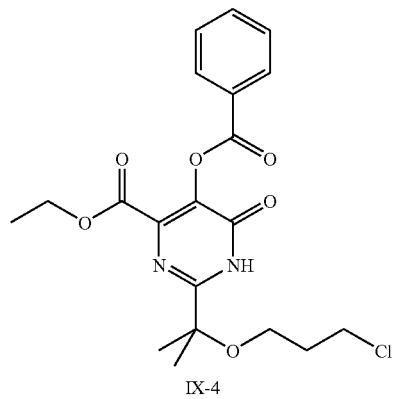
IX-4
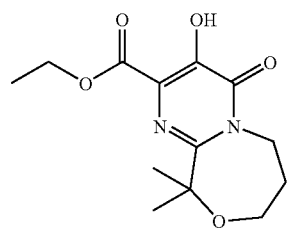
IX-6
K₂CO₃, DMF ↓     Scheme I ↓
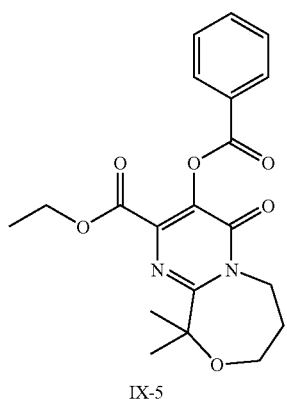
IX-5
Scheme I →
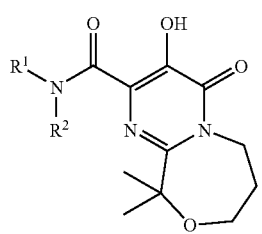

In Scheme X, IX-3 can be used to synthesize the benzylated intermediate X-1. This intermediate can be carried on to final product using methods analogous to those described in Scheme VIII.

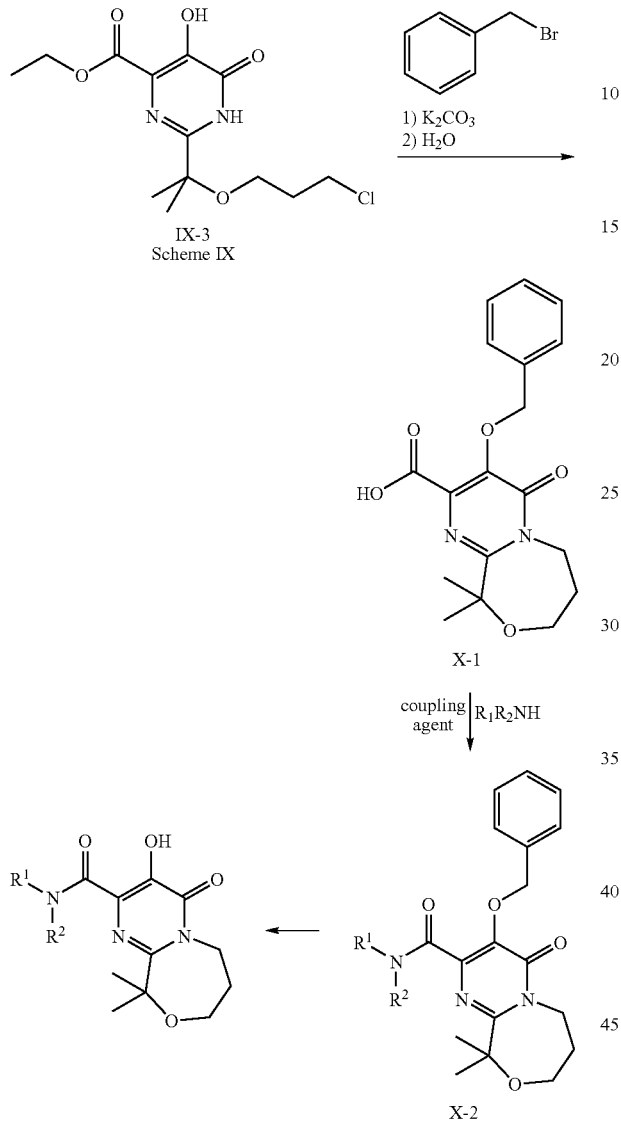

In yet another method, Scheme XI illustrates the synthesis of sulfonamide containing examples, starting from 5-fluoro-2-methylbenzen-1-sulfonlyl chloride.

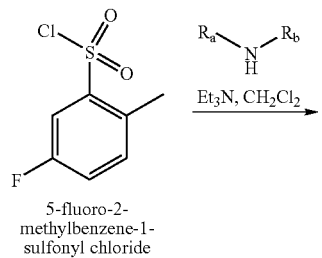

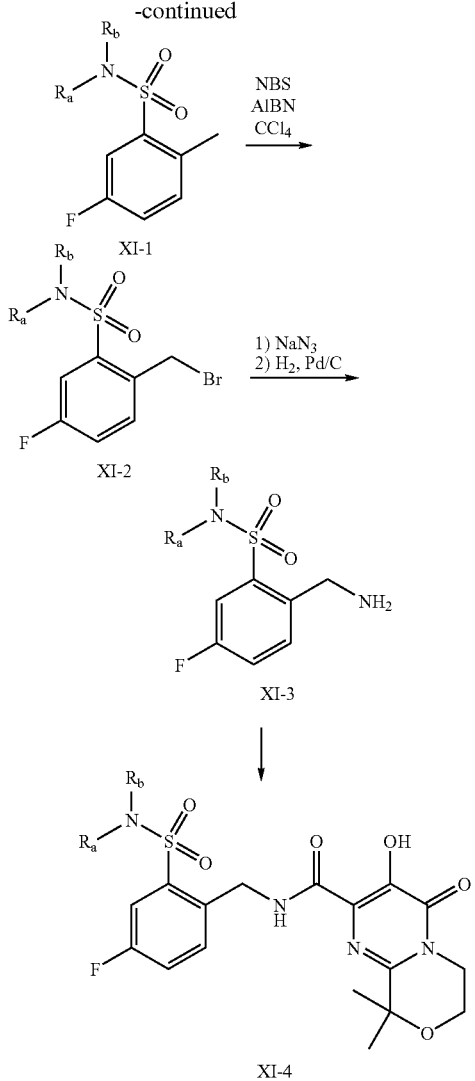

In yet another method, Scheme XII illustrates an alternate route to the synthesis of sulfonamide containing benzylamines starting from 2,4-difluorobenzonitrile.

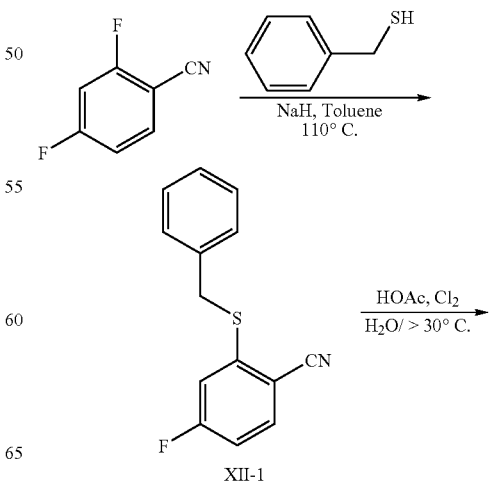

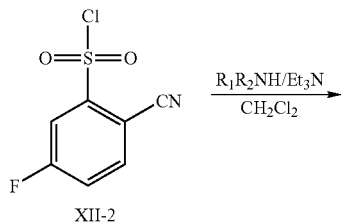
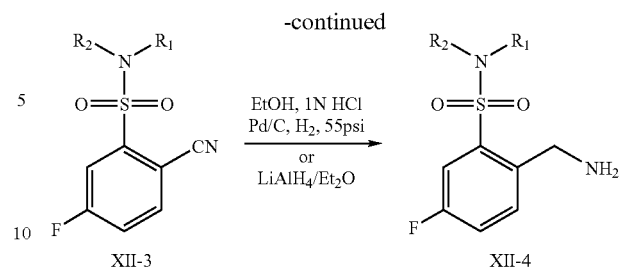
Some examples of the invention can be synthesized according to the methods illustrated in Schemes XIII-XXIX.
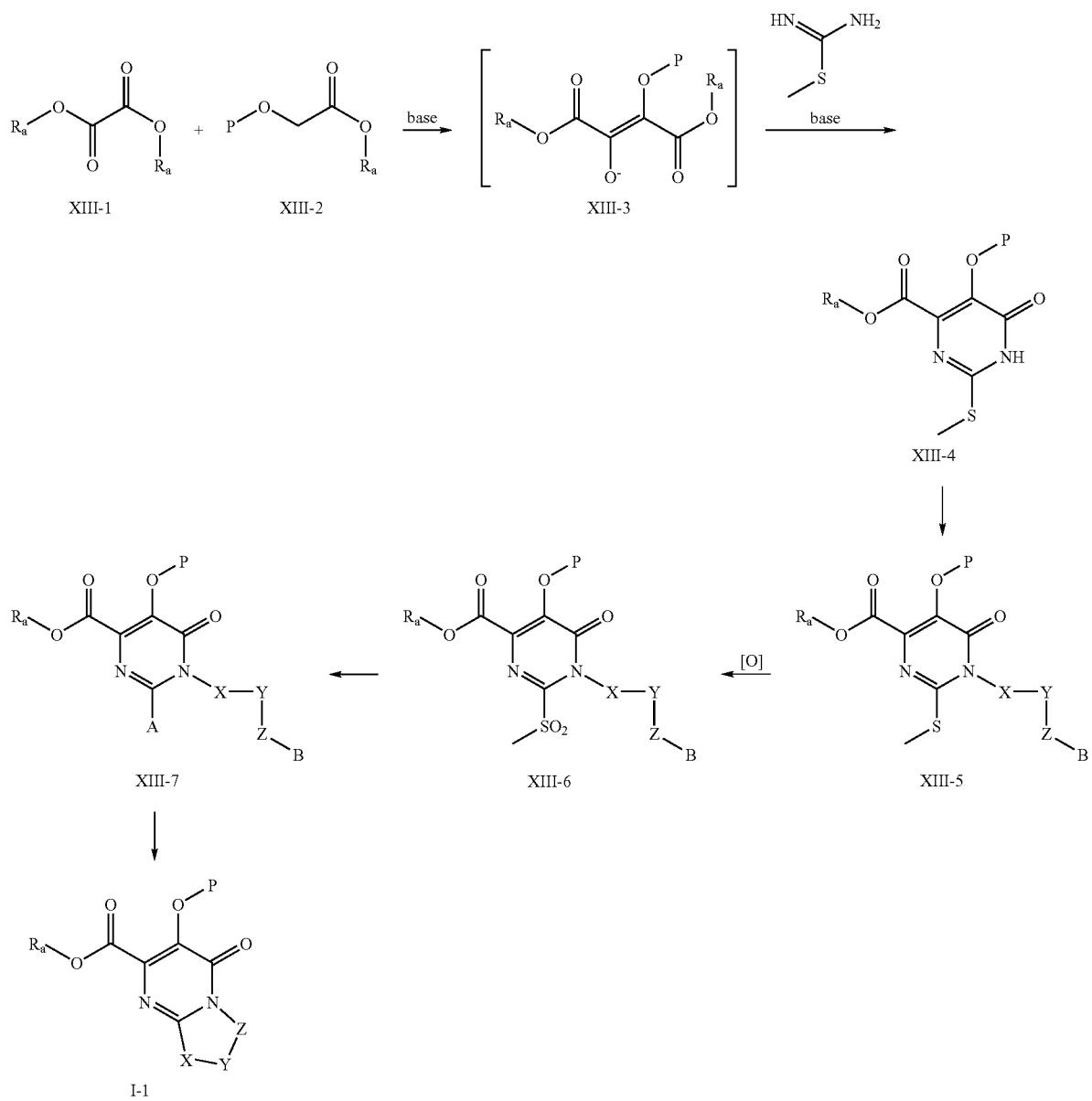

Scheme XIV
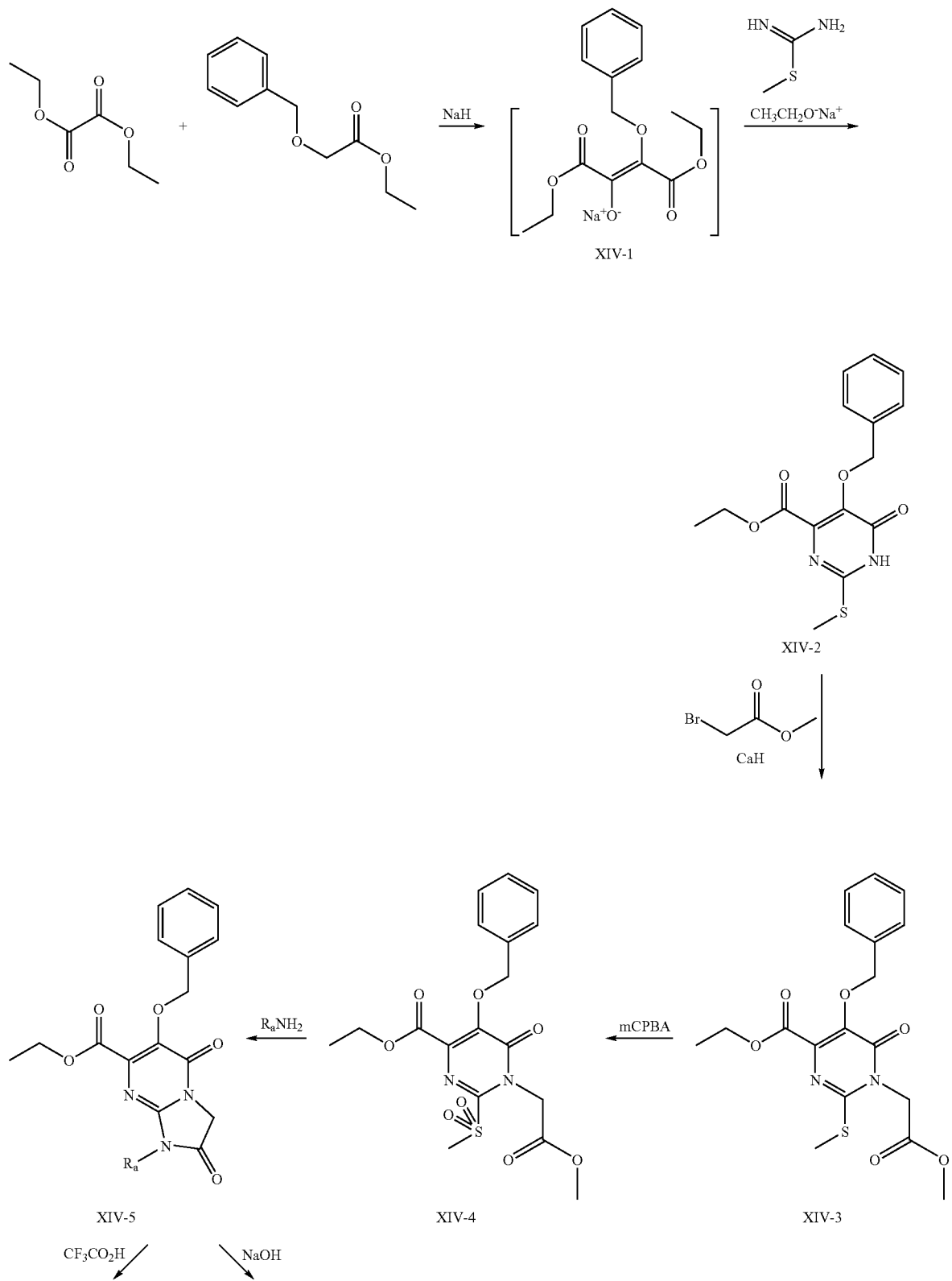

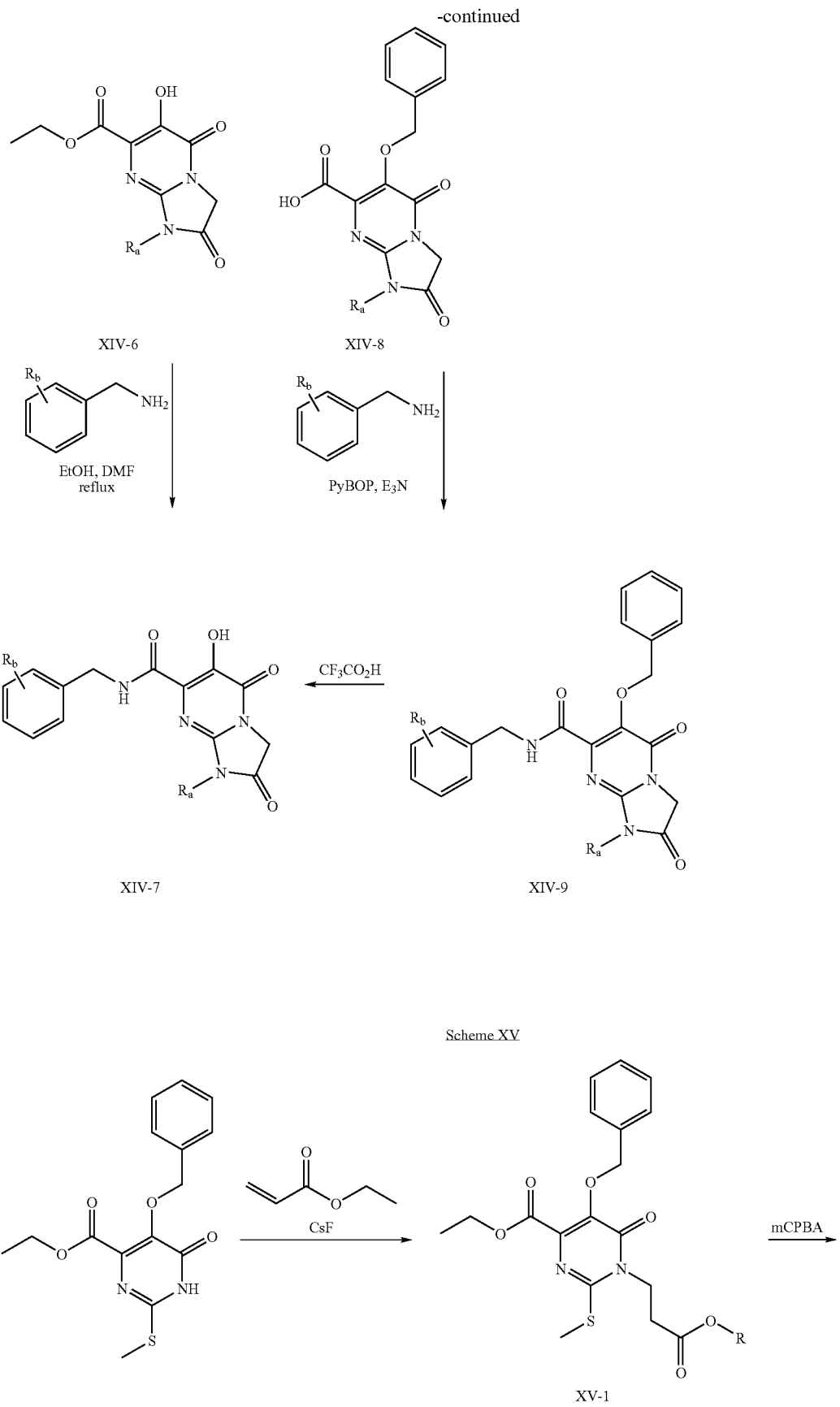

-continued
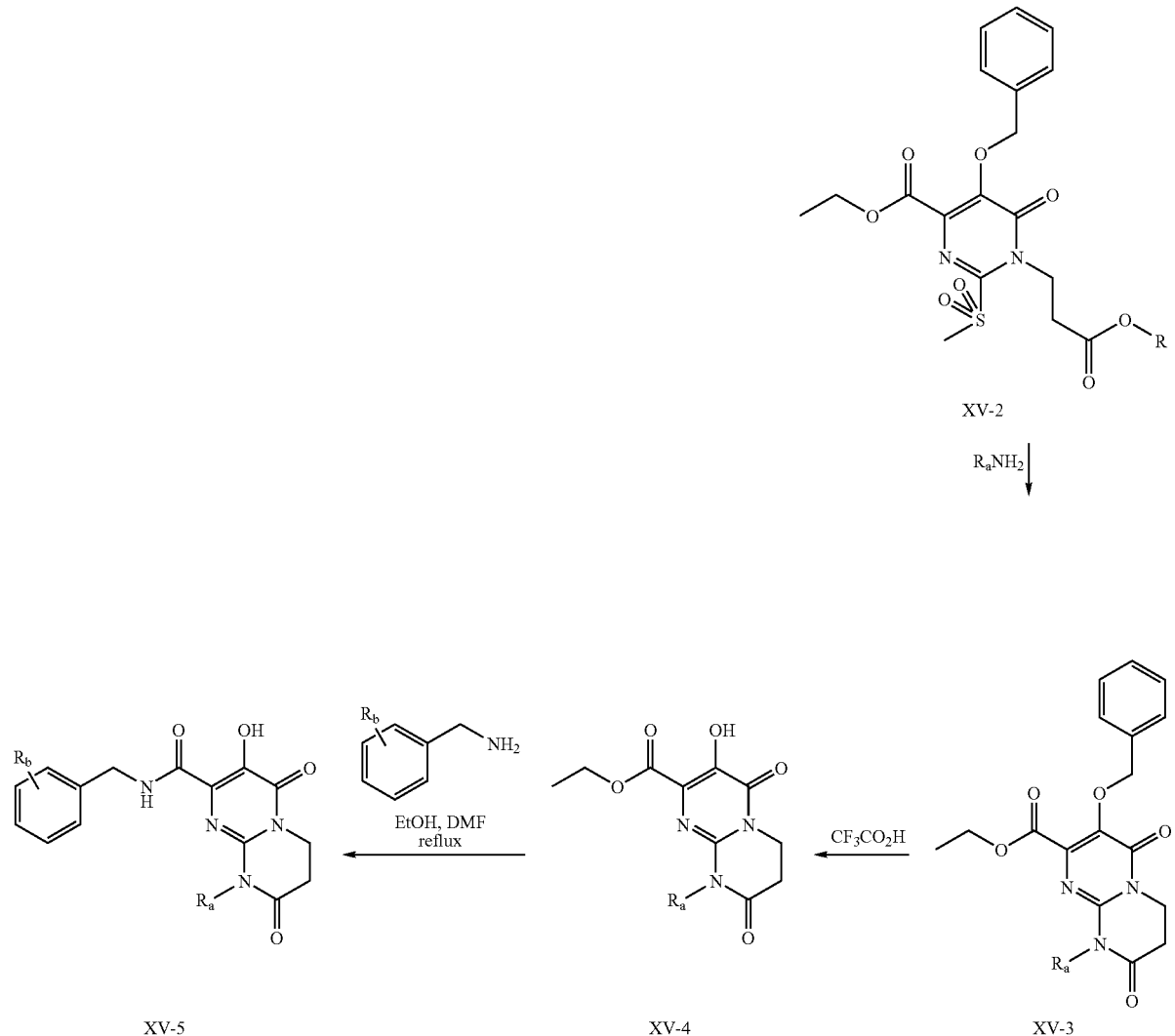
Scheme XVI
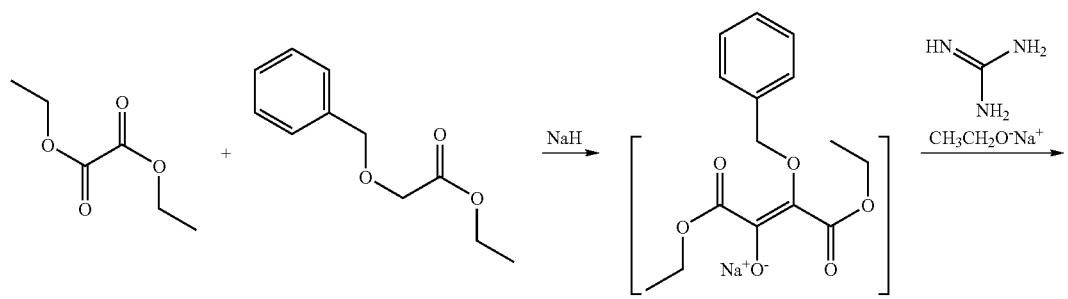

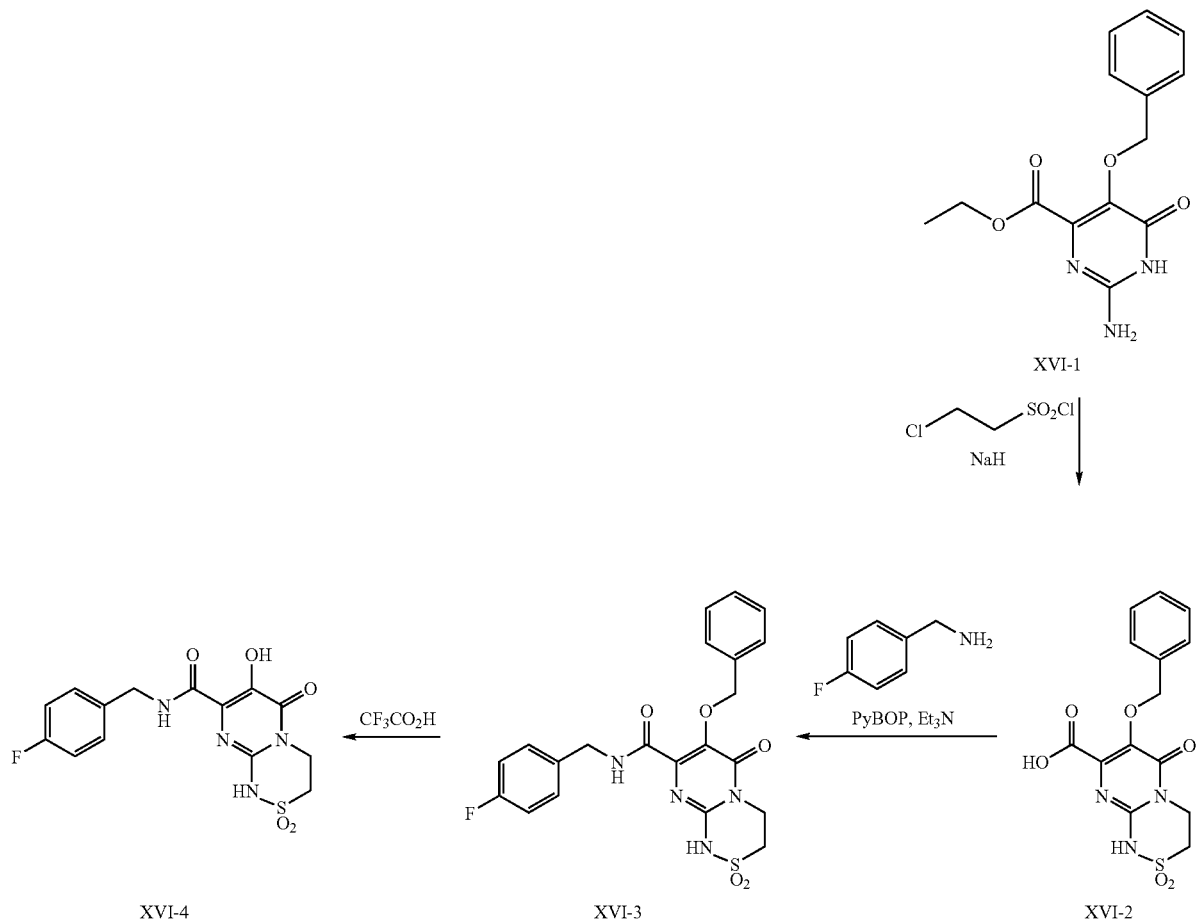
Scheme XVII
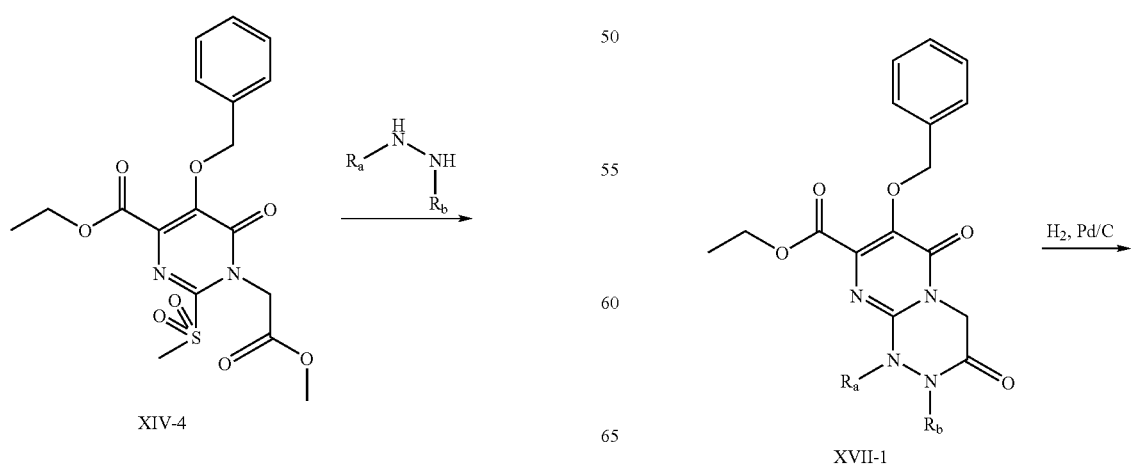

-continued
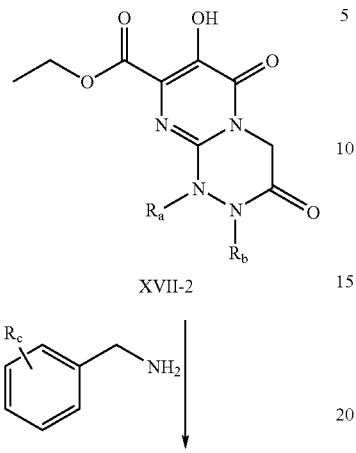
XVII-2
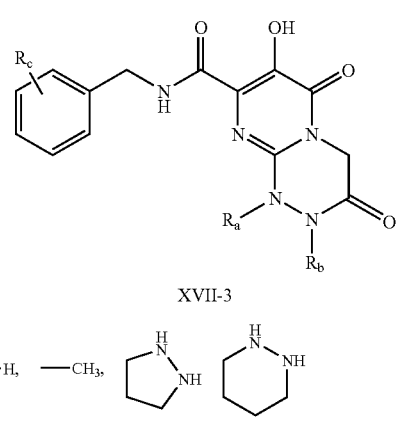
XVII-3
Scheme XVIII
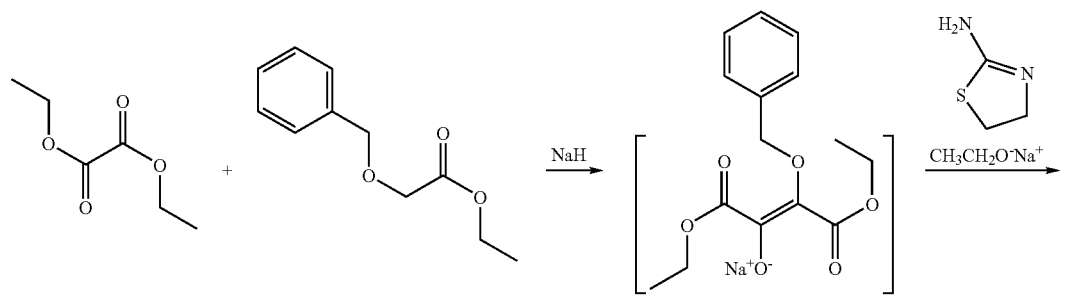
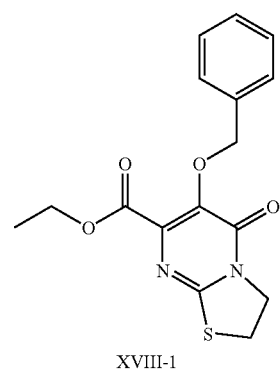
XVIII-1

-continued
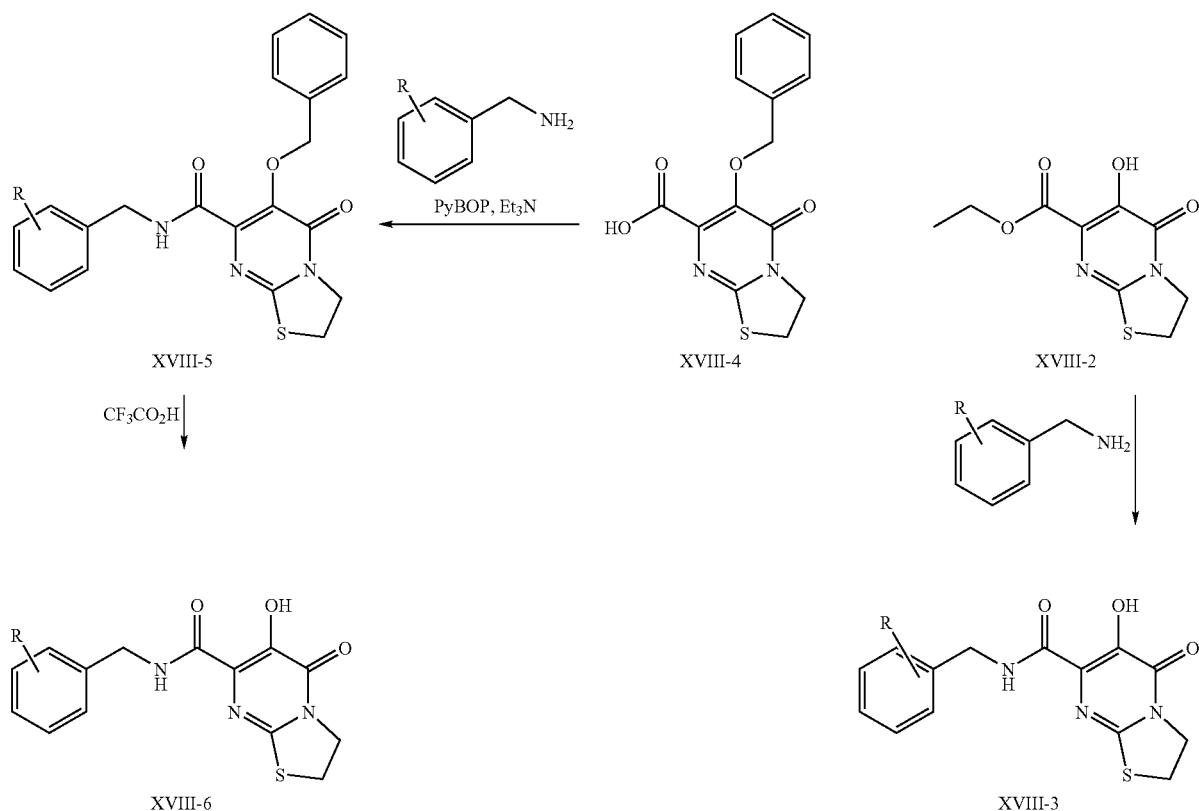
Scheme XIX
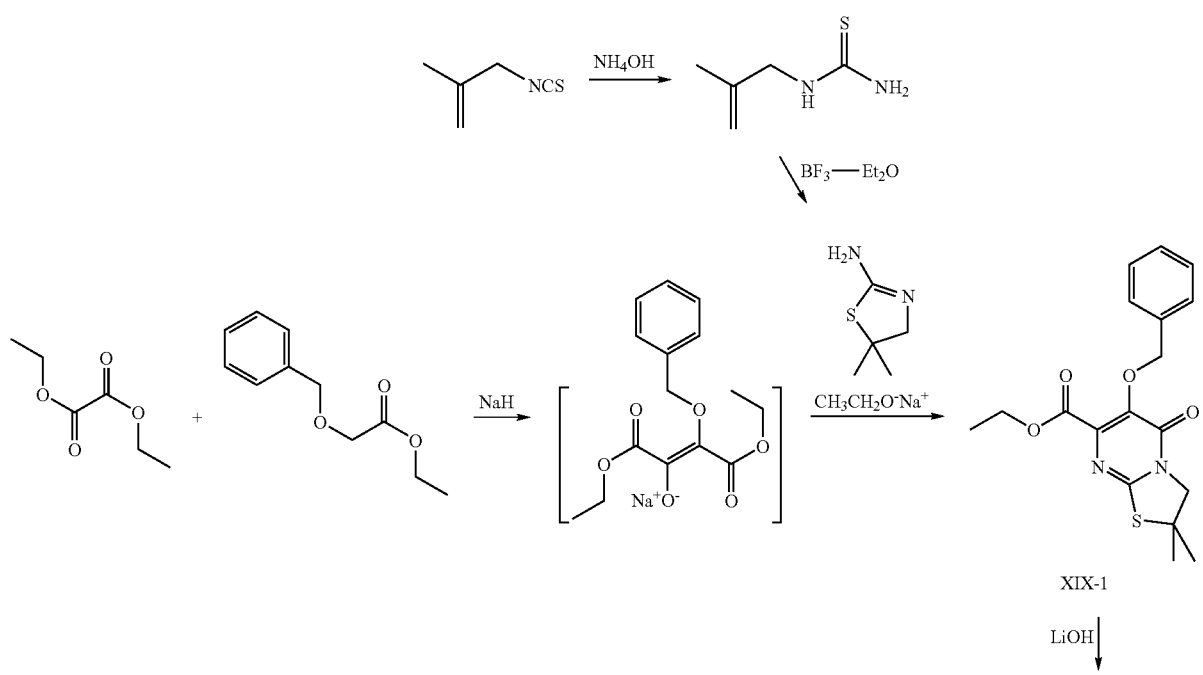

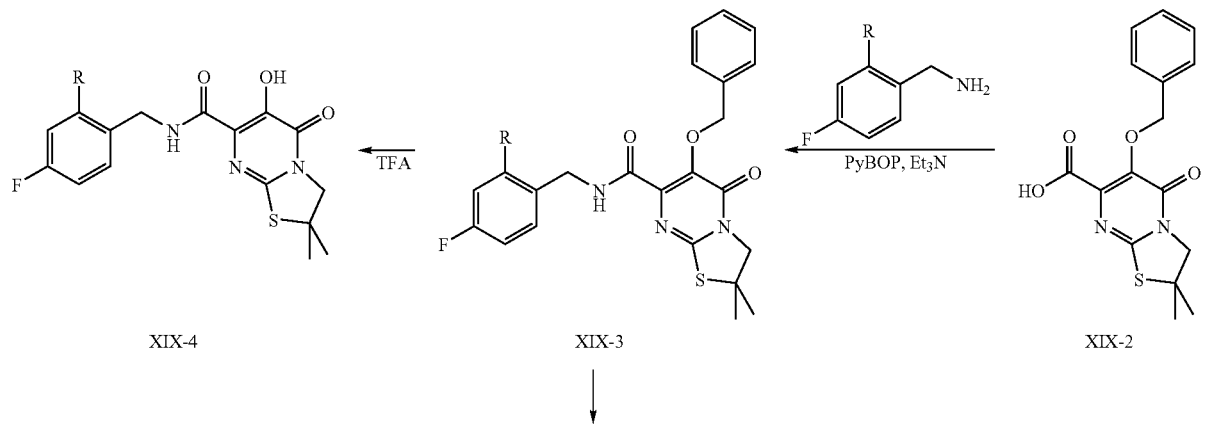
XIX-4     XIX-3     XIX-2
Scheme XX
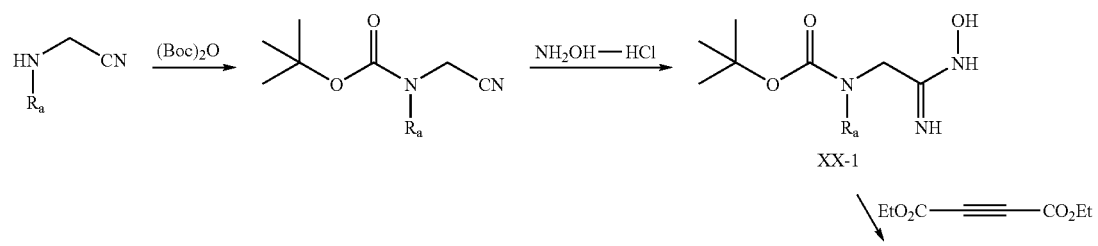
XX-1
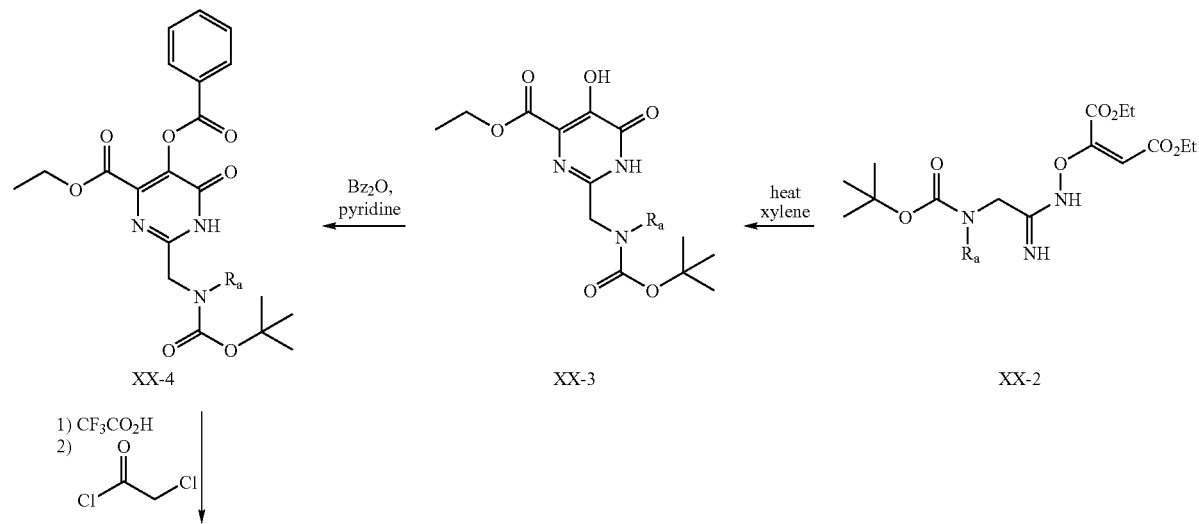
XX-4     XX-3     XX-2

-continued
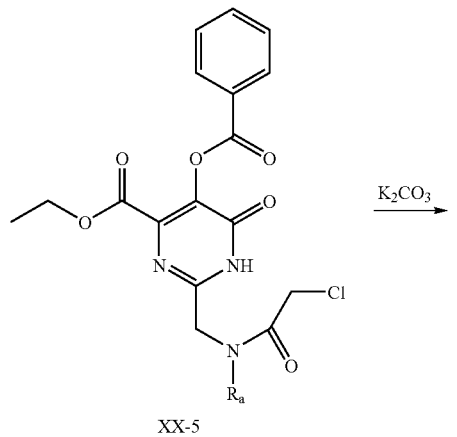
XX-5
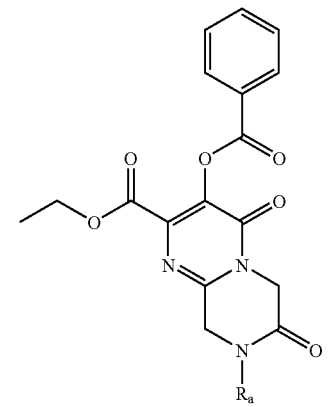
XX-6
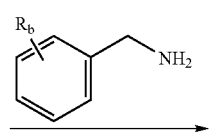
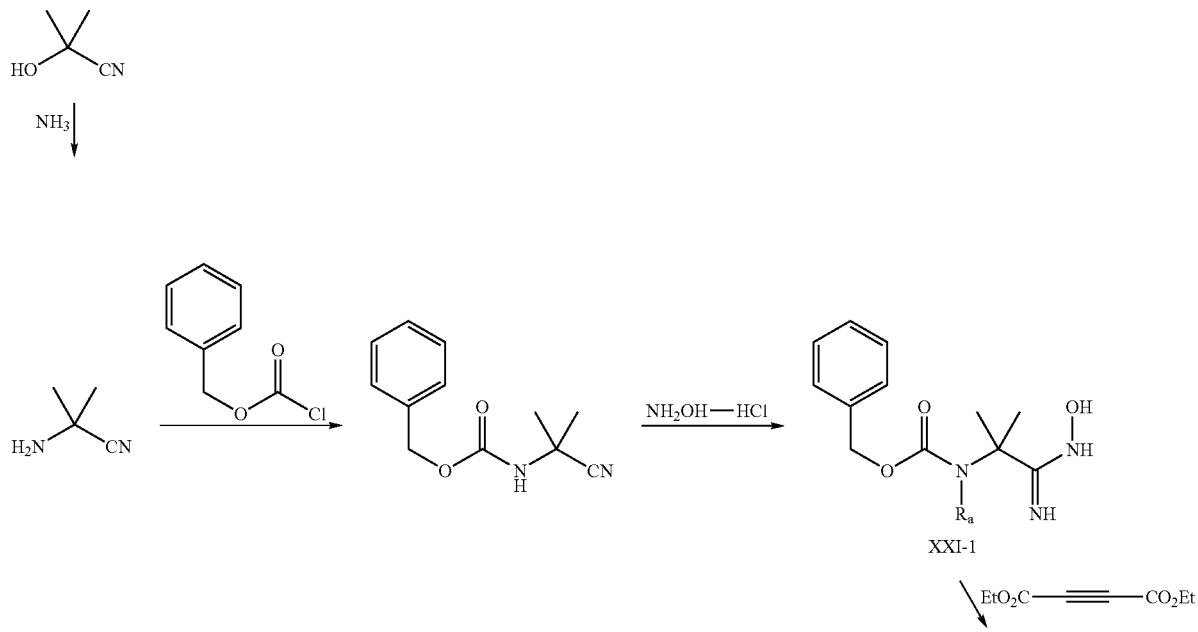
XX-7
$R_a =$ —H, —CH$_3$,
Scheme XXI
XXI-1

-continued
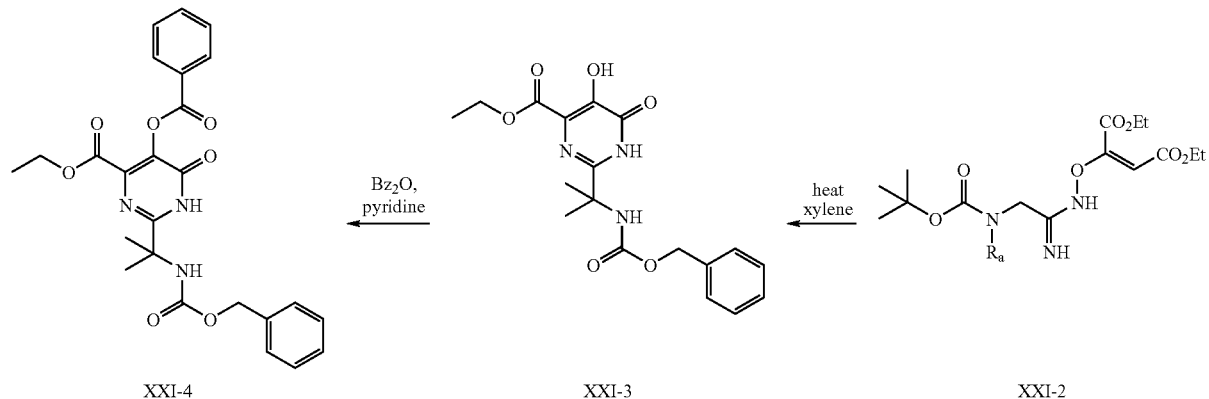
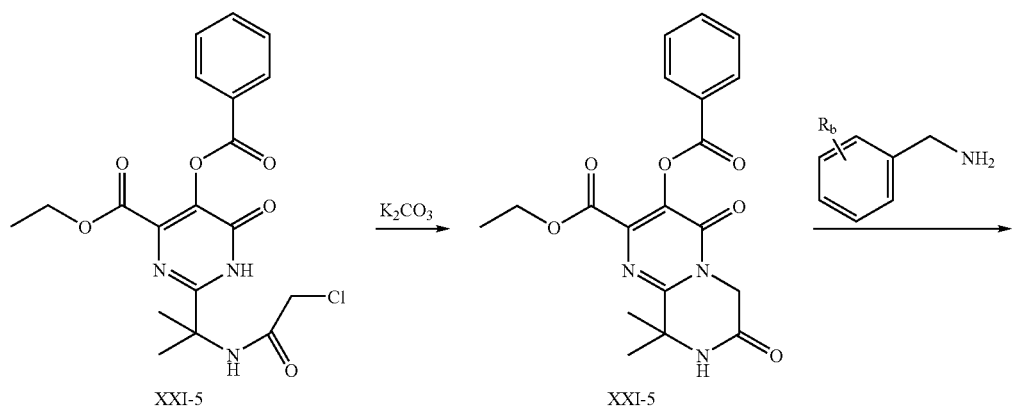
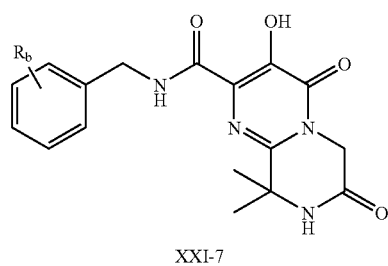

Scheme XXII
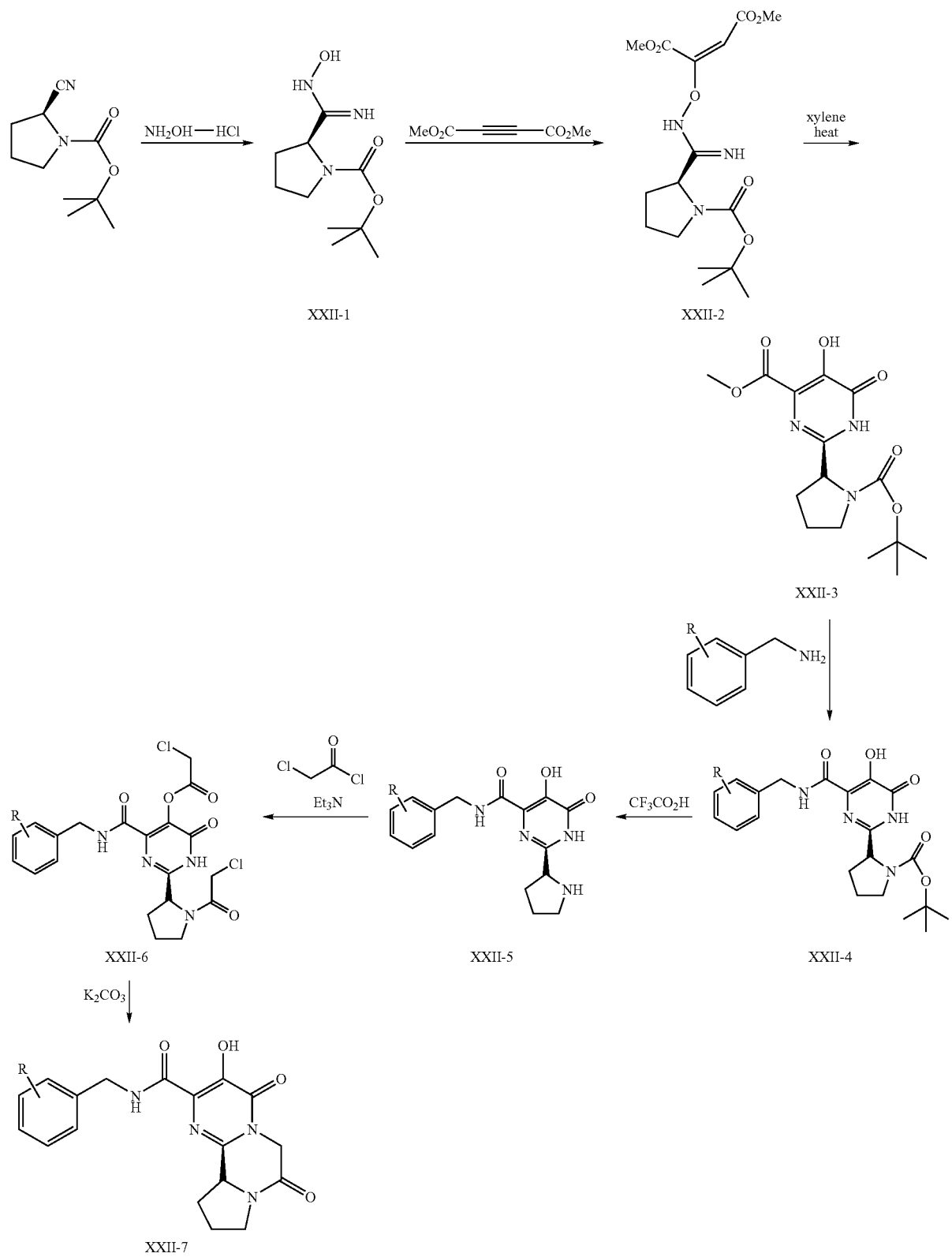

Scheme XXIII
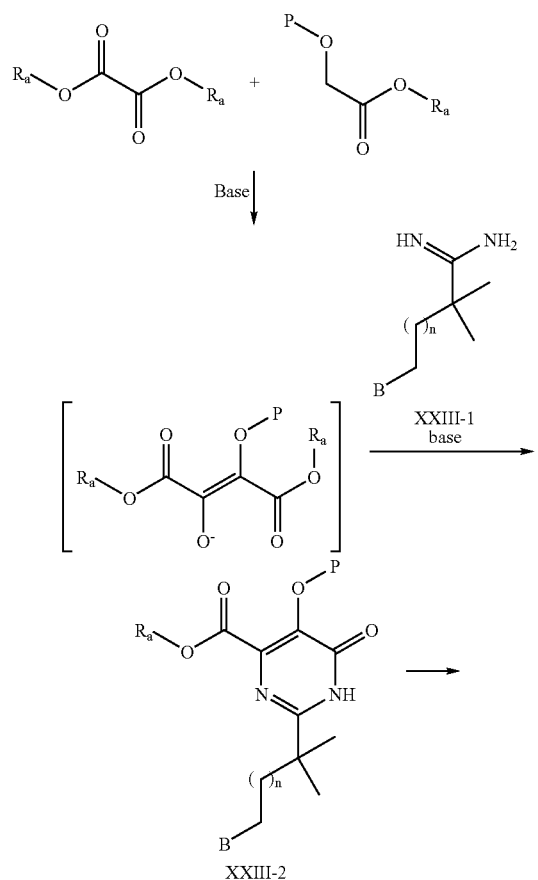
Scheme XXIV
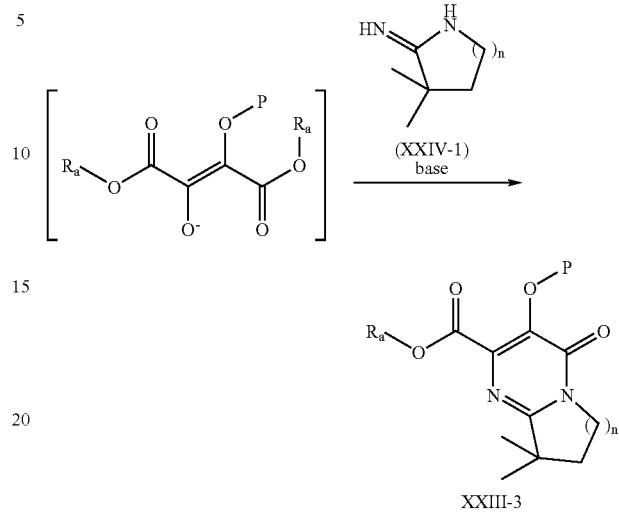
Scheme XXV
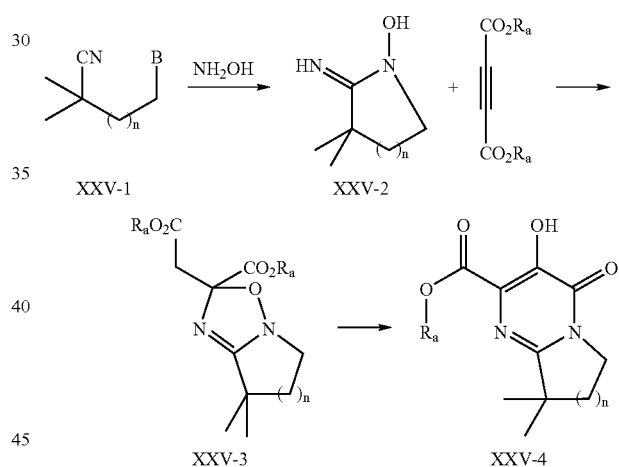
Scheme XXVI
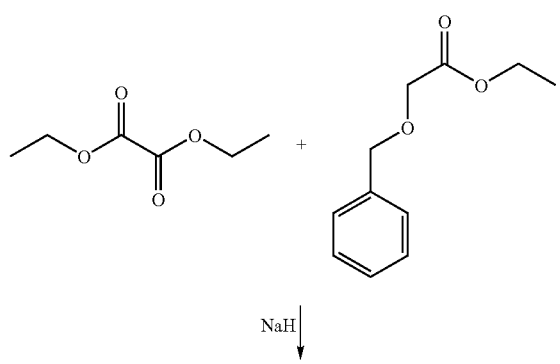

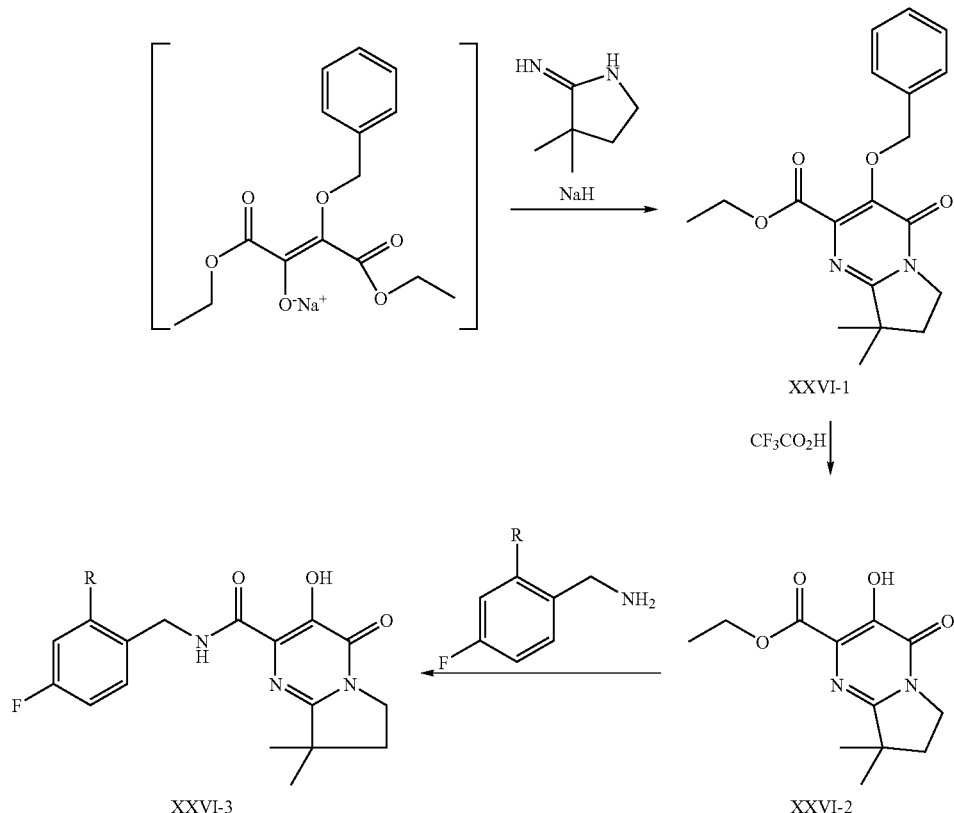
Scheme XXVII
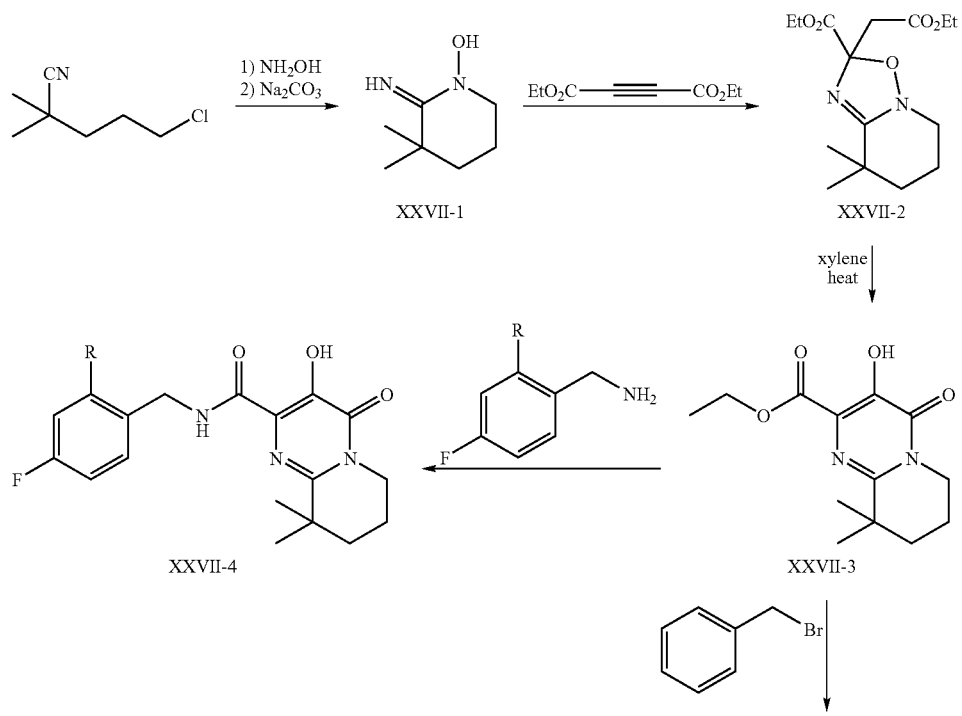

-continued
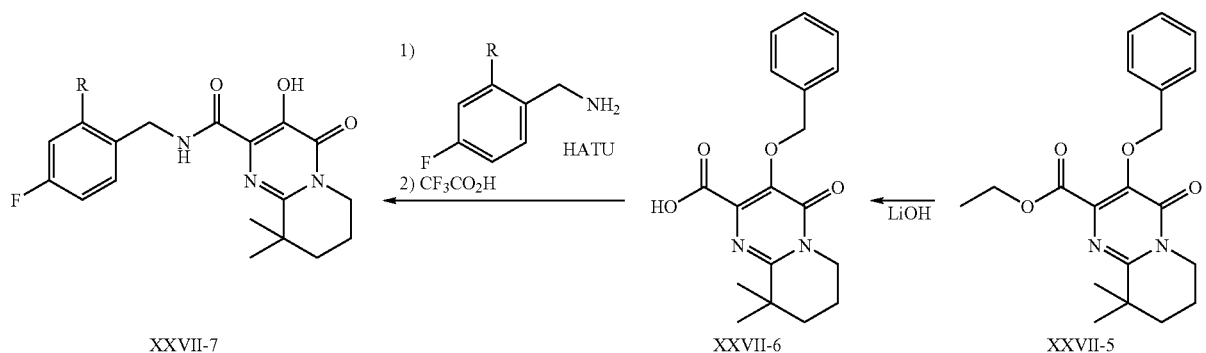
Scheme XXVIII
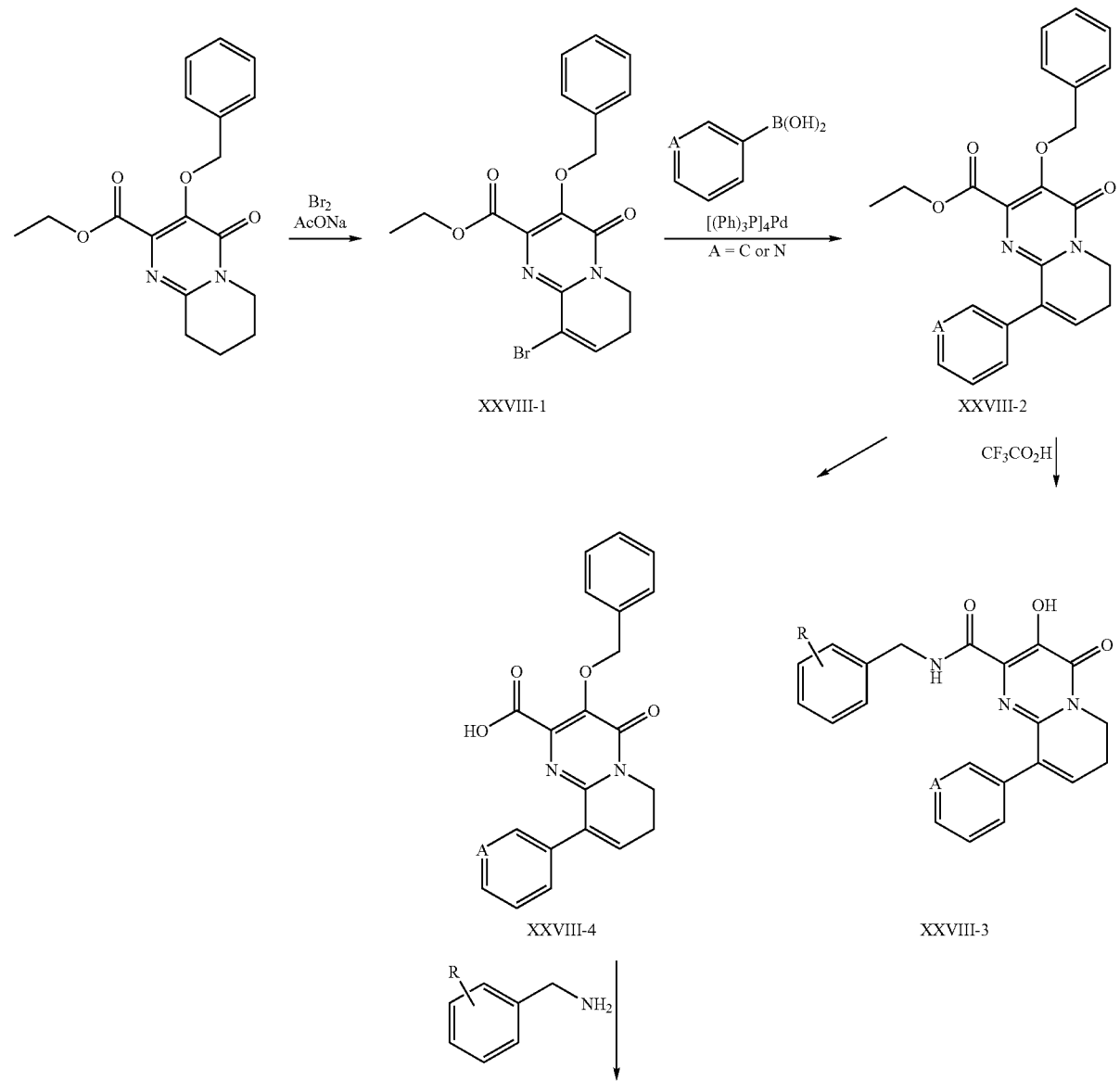

-continued
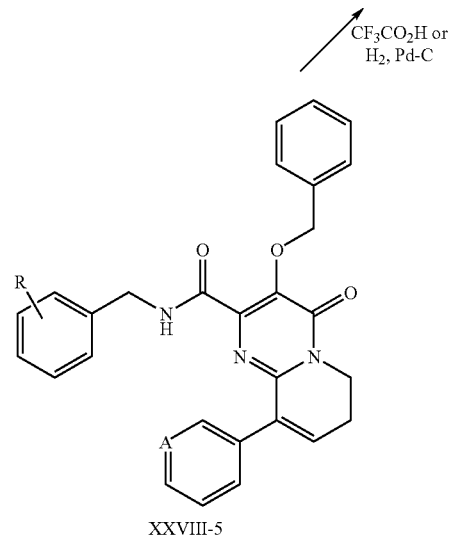
XXVIII-5
Scheme XXIX
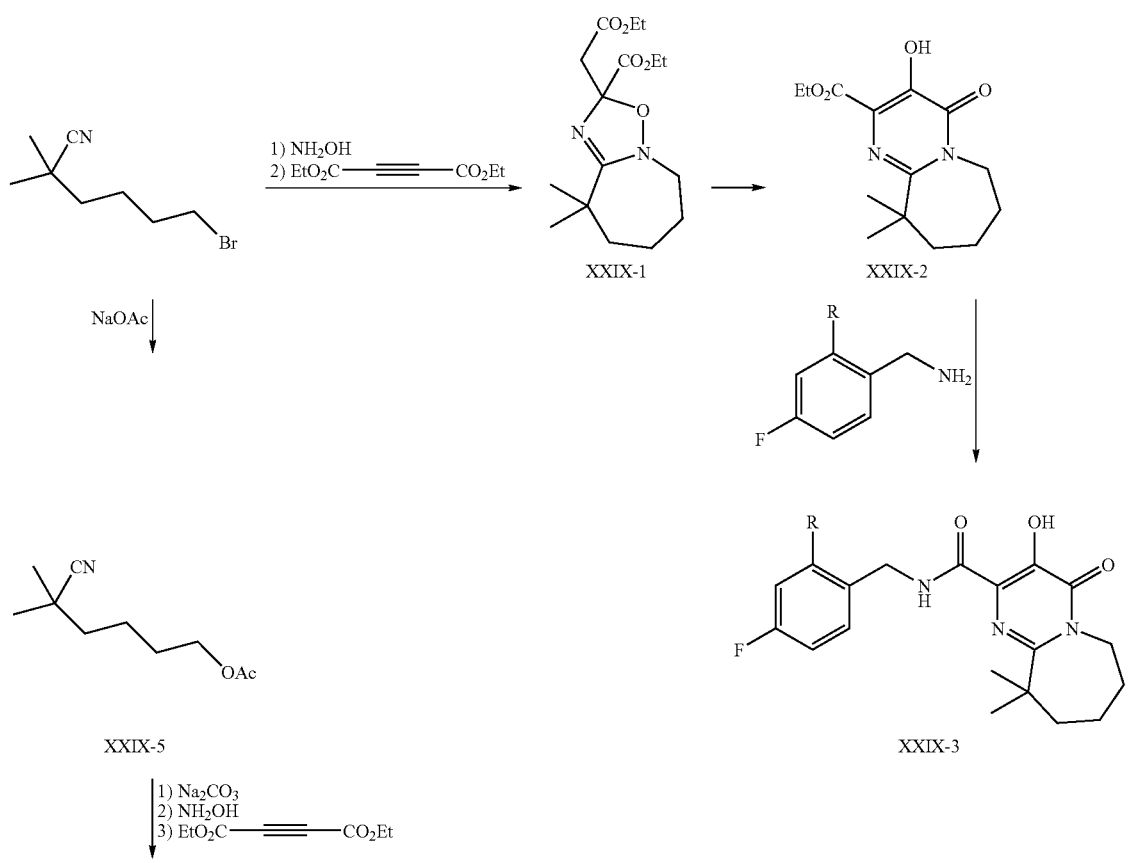

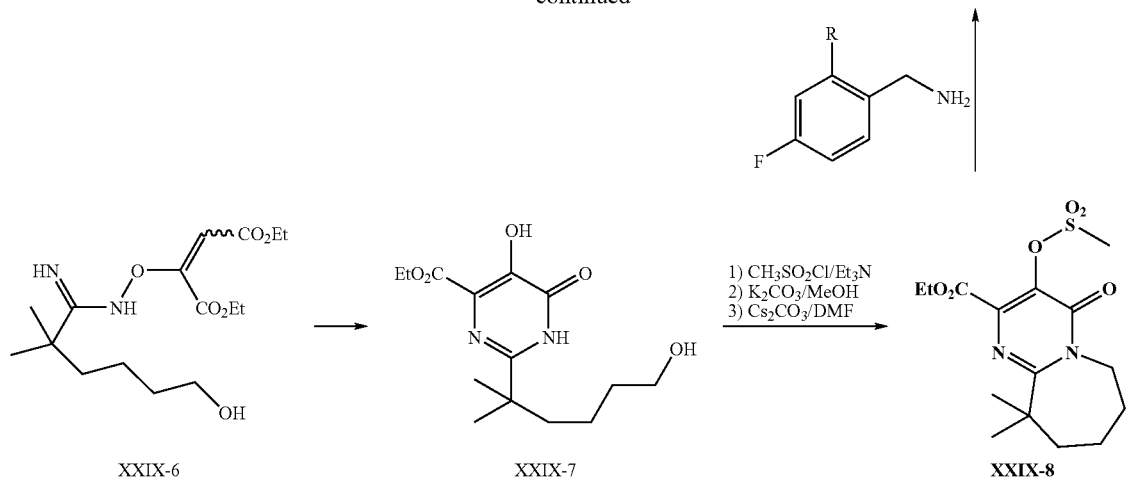

Biological Methods

HIV-Integrase InhibitionActivity. To evaluate in-vitro activity against HIV-integrase, 5 pmole of biotin labeled substrate DNA was bound to 100 µg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908-5911 (1995). The sequences of substrate and target DNA were described in *Nucleic Acid Research* 22, 1121-1122 (1994).

Results are shown in the table 1. Activity equal to A refers to a compound having $IC_{50}=0.002$ to 0.10 µM while B and C denote compounds having $IC_{50}=0.1$ to 1.0 µM and $IC_{50} \geq 1.0$ µM respectively.

TABLE 1

| Example | Activity |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |

TABLE 1-continued

| Example | Activity |
|---|---|
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the pvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assy. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the Table 2. Activity equal to A refers to a compound having $EC_{50}$=0.003 to 0.10 µM while B and C denote compound with $EC_{50}$=0.1 to 1.0 µM and $EC_{50}\geq$1.0 µM respectively.

TABLE 2

| Example | Activity |
|---------|----------|
| 1 | A |
| 2 | A |
| 3 | A |
| 4 | A |
| 5 | A |
| 6 | A |
| 7 | A |
| 8 | A |
| 9 | A |
| 10 | B |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |

Pharmaceutical Composition and Methods of Use

The compound of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

Accordingly, another aspect of the invention is a method for treating HIV infection in a human patient comprising administering a therapeutically effective amount of a compound of Formula I, or a pharmaceutically acceptable salt or solvate thereof, with a pharmaceutically acceptable carrier.

Another aspect of the invention is a method for treating HIV infection in a human patient comprising the administration of a therapeutically effective amount of a compound of Formula I, or a pharmaceutically acceptable salt or solvate thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt or solvate thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdinc, efavirenz, and nevirapine, or a pharmaceutically acceptable salt or solvate thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt or solvate thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt or solvate thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt or solvate thereof.

Another aspect of the invention is a method wherein the agent is a CXCR4 inhibitor.

Another aspect of the invention is a method wherein the CXCR4 inhibitor is AMD-3100, or a pharmaceutically acceptable salt or solvate thereof.

Another aspect of the invention is a method wherein the agent is an HIV budding or maturation inhibitor.

Another aspect of the invention is a method wherein the budding or maturation inhibitor is PA-457, or a pharmaceutically acceptable salt, or solvate thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt or solvate thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt or solvate thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt or solvate thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt or solvate thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt or solvate thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt or solvate thereof.

Another aspect of the invention is a method wherein the agent is a CXCR4 inhibitor.

Another aspect of the invention is a method wherein the CXCR4 inhibitor is AMD-3100 or a pharmaceutically acceptable salt or solvate thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt or solvate thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 3 lists some agents useful in treating AIDS and HIV infection which are suitable for this invention.

TABLE 3

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |

TABLE 3-continued

| DRUG NAME | MANUFACTURER | INDICATION |
|---|---|---|
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, PGL HIV positive, AIDS |
| AL-721 | Ethigen (Los Angeles, CA) | |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche-/Trimeris | HIV infection, AIDS, viral fusion inhibitor |
| Trizivir ® | | HIV infection, AIDS |
| Kaletra ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |

TABLE 3-continued

| DRUG NAME | MANUFACTURER | INDICATION |
|---|---|---|
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide Granulocyte Colony Stimulating Factor | Ciba-Geigy Corp. Amgen | Kaposi's sarcoma AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

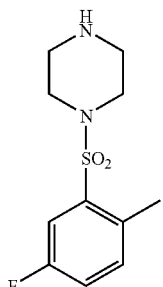

Intermediate 1

1-(5-Fluoro-2-methylphenylsulfonyl) piperazine: 5-Fluoro-2-methylbenzenesulfonyl chloride (35.1 g, 168.5 mmol) in diethyl ether (50 mL) was added drop-wise to a suspension of piperazine (28.8 g, 337.0 mmol) in diethyl ether (500 mL) and triethylamine (47 mL, 337.0 mmol). The white suspension was stirred at room temp for 1.5 h. The mixture was washed with saturated aqueous sodium carbonate. The organic phase was washed with water and brine and dried ($Na_2SO_4$). Concentration gave a white solid that was triturated with diethyl ether to give the title compound as a white solid (30.95 g, 36% yield). $^1H$ NMR (300 MHz, $CDCl_3$) δ: 7.57 (1H, dd, J=8.6, 2.7 Hz), 7.25 (1H, dd, J=8.4, 5.1 Hz), 7.12 (1H, td, J=8.1, 2.8 Hz), 3.13-3.10 (4H, m), 2.98-2.85 (4H, m), 2.55 (3H, s), 1.69 (1H, bs). LCMS (M+H) calcd for $C_{11}H_{16}FN_2O_2S$: 259.09; found: 259.18.

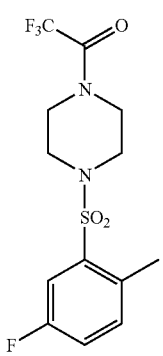

Intermediate 2

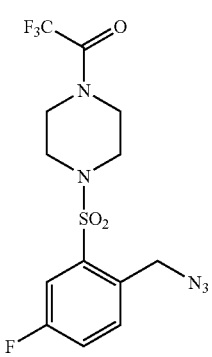

Intermediate 4

2,2,2-Trifluoro-1-(4-(5-fluoro-2-methylphenylsulfonyl)piperazin-1-yl)ethanone: A mixture of Intermediate 1 (30.9 g, 120 mmol), triethylamine (16.8 mL, 120 mmol) and trifluoroethyl acetate (18 mL, 150 mmol) in methanol (60 mL) was stirred at room temp for 18 h. The mixture was concentrated and the residue was partitioned between ethyl acetate and water filtering off the insoluble solids. The organic phase was washed with 1N aqueous HCl, saturated aqueous sodium bicarbonate, water and brine. After drying ($Na_2SO_4$) and concentrating, the title compound was obtained as colorless oil that solidified to a white solid upon standing (37.5 g, 88% yield). $^1$H NMR (300 MHz, $CDCl_3$) δ: 7.58 (1H, dd, J=8.4, 2.9 Hz), 7.29 (1H, dd, J=8.4, 5.1 Hz), 7.18 (1H, td, J=8.0, 2.8 Hz), 3.76-3.73 (2H, m), 3.68-3.65 (2H, m), 3.28-3.23 (4H, m), 2.55 (3H, s). LCMS (M+H) calcd for $C_{13}H_{15}F_4N_2O_3S$: 355.07; found: 355.14.

1-(4-(2-(Azidomethyl)-5-fluorophenylsulfonyl)piperazin-1-yl)-2,2,2-trifluoroethanone: Intermediate 3 (41.0 g, not pure) was dissolved in DMF (100 mL). Sodium azide (6.2 g, 94 mmol) was added and the mixture was stirred at 80° C. for 4 h. The mixture was cooled and concentrated to near dryness. The residue was partitioned between EtOAc and water. The organic phase was washed with water, brine, dried ($Na_2SO_4$) and concentrated. Purification by flash chromatography eluting with 10% EtOAc/hexane gave the title compound as colorless oil (23.8 g, 57% yield over two steps). $^1$H NMR (300 MHz, $CDCl_3$) δ: 7.64-7.56 (2H, m), 7.36-7.27 (1H, m), 4.72 (2H, s), 3.78-3.64 (4H, m), 3.28-3.23 (4H, m).

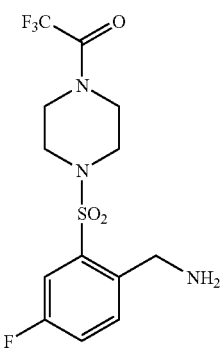

Intermediate 5

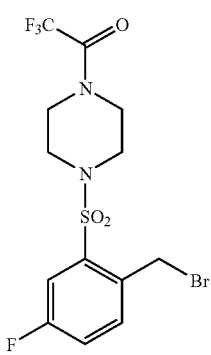

Intermediate 3

1-(4-(2-(Bromomethyl)-5-fluorophenylsulfonyl)piperazin-1-yl)-2,2,2-trifluoroethanone: A mixture of Intermediate 2 (37.5 g, 105.9 mmol), NBS (19.4 g, 105.9 mmol) and AIBN (0.45 g, 2.8 mmol) in carbon tetrachloride (500 mL) was refluxed for 4 h. The mixture was cooled, concentrated and purified over silica gel eluting with EtOAc to give the title compound contaminated with starting material and dibrominated side-product as amber oil (41.0 g). LCMS (M+H) calcd for $C_{13}H_{14}F_4N_2O_3SBr$: 433.97; found: 433.01.

1-(4-(2-(Aminomethyl)-5-fluorophenylsulfonyl)piperazin-1-yl)-2,2,2-trifluoroethanone: A solution of Intermediate 4 (23.8 g, 60.2 mmol) was dissolved in EtOH (100 mL), EtOAc (30 mL) and 1N aqueous HCl (60 mL, 60 mmol) was degassed by bubbling N2 through it. Then 10% Pd/C (1.0 g) was added and the mixture was shaken under $H_2$ at 50 psi for 18 h. The reaction mixture was filtered over celite and the solution was concentrated. The residue was partitioned between EtOAc and water. The aqueous phase was freeze dried to give the title compound as a white solid HCl salt (7.91 g, 32% yield). LCMS (M+H) calcd for $C_{13}H_{16}F_4N_3O_3S$: 370.08; found: 370.17.

Intermediate 6

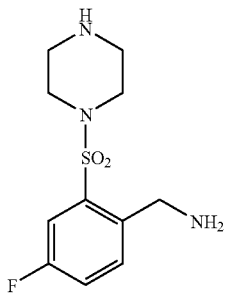

(4-Fluoro-2-(piperazin-1-ylsulfonyl)phenyl)methanamine: A solution of Intermediate 5 (7.9 g, 19.5 mmol) and potassium hydroxide (5.6 g, 98 mmol) in MeOH (50 mL) was stirred at room temp for 30 min. Solids formed during the reaction were removed by filtration and the solution was concentrated. The resulting oil was dissolved in water and made acidic with 1N aqueous HCl. The aqueous solution was washed with EtOAc and freeze dried to give the title compound as a white solid HCl salt (6.7 g, 100% yield). $^1$H NMR (300 MHz, DMSO-$d_6$) δ: 9.47 (1H, bs), 8.66 (2H, bs), 7.92 (1H, dd, J=8.4, 5.1 Hz), 7.80-7.73 (2H, m), 4.32 (2H s), 3.38-3.32 (4H, m), 3.20-3.17 (4H, m). LCMS (M+H) calcd for $C_{11}H_{17}FN_3O_2S$: 274.10; found: 274.20.

Intermediate 7

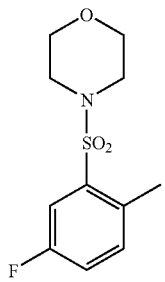

4-(5-Fluoro-2-methylphenylsulfonyl)mortholine: Following the procedure for Intermediate 1 using 5-fluoro-2-methylbenzenesulfonyl chloride (10.0 g, 48 mmol), triethylamine (13.9 mL, 100 mmol) and morpholine (8.37 g, 96 mmol) gave the title compound as a white solid (10.07 g, 81% yield). $^1$H NMR (300 MHz, CDCl$_3$) δ: 7.58 (1H, dd, J=8.6, 2.7 Hz), 7.27 (1H, dd, J=8.4, 5.1 Hz), 7.15 (1H, td, J=8.1, 2.8 Hz), 3.72-3.68 (4H, m), 3.16-3.13 (4H, m), 2.57 (3H, s). LCMS (M+H) calcd for $C_{11}H_{15}FNO_3S$: 260.07; found: 260.15.

Intermediate 8

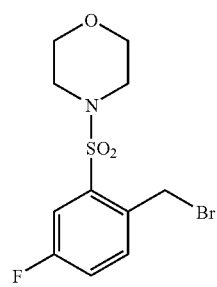

4-(2-(Bromomethyl)-5-fluorophenylsulfonyl)morpholine: Following the procedure for Intermediate 3 using Intermediate 7 (10.0 g, 38.6 mmol) gave the title compound as yellow oil that was carried on without purification.

Intermediate 9

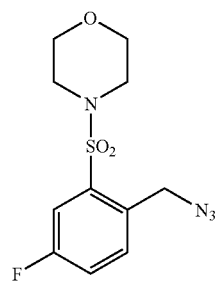

4-(2-(Azidomethyl)-5-fluorophenylsulfonyl)morpholine: Following the procedure for Intermediate 4 using Intermediate 8 (crude) gave the title compound as pale yellow oil (8.21 g, 71% yield over 2 steps).

Intermediate 10

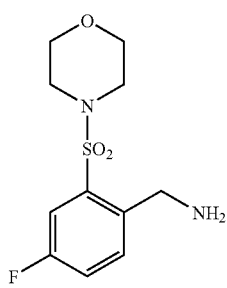

(4-Fluoro-2-(morpholinosulfonyl)phenyl)methanamine: Following the procedure for Intermediate 5 using Intermediate 9 gave the title compound as a brown solid HCl salt (4.29 g, 51% yield). $^1$H NMR (300 MHz, CD$_3$OD) δ: 7.80-7.73 (2H, m), 7.57 (1H, td, J=8.1, 2.8 Hz), 4.43 (2H, s), 3.76-3.73 (4H, m), 3.19-3.15 (4H, m). LCMS (M+H) calcd for $C_{11}H_{16}FN_2O_3S$: 275.08; found: 275.15.

Intermediate 11

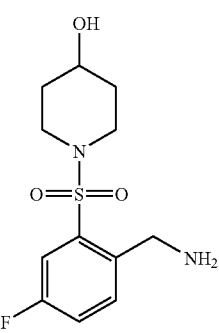

Prepared according to the procedure for Intermediate 10 using 4-hydroxypiperidine. $^1$H NMR (300 MHz, CD$_3$OD) δ: 7.78-7.71 (2H, m), 7.54 (1H, t, J=8.2, 2.9 Hz), 4.43 (2H, s), 3.82-3.74 (1H, m), 3.56-3.49 (2H, m), 3.12-3.04 (2H, m), 1.98-1.89 (2H, m), 1.66-1.55 (2H, m). LCMS (M+H) calcd for $C_{12}H_{18}N_2O_3FS$: 289.10; found: 289.16.

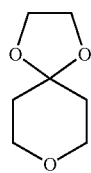

Intermediate 12

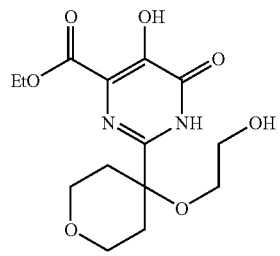

Intermediate 14

1,4,8-Trioxa-spiro[4.5]decane. A mixture of tetrahydro-4-pyranone (10 g, 99.9 mmol), ethylene glycol (20 mL, 150 mmol) and catalytic toluene sulfonic acid was refluxed in benzene (120 mL) for 5 h. After cooling to room temp, the benzene layer was decanted from the dark oil in the bottom of the flask and concentrated. The resulting oil was taken up in methylene chloride and shaken in a separatory funnel. The $CH_2Cl_2$ layer was decanted from the insoluble oil. The $CH_2Cl_2$ layer was concentrated to give the intermediate 16 as pale yellow oil (11.62 g, 81% yield). $^1$H-NMR (300 MHz, $CDCl_3$) δ: 3.91 (4H, s), 3.71 (4H, t, J=5.5 Hz), 1.68 (4H, t, J=5.7 Hz).

5-Hydroxy-2-[4-(2-hydroxyethoxy)tetrahydropyran-4-yl]-6-oxo-1,6-dihydropyrimidine-4-carboxylic acid ethyl ester. A solution of an intermediate 13 (9.3 g, 25 mmol) in xylenes (150 mL) was refluxed for 18 h. After cooling to room temp, the mixture was shaken with 0.2 M $Na_2CO_3$. The aqueous phase was washed with EtOAc, made acidic with conc. HCl and extracted with $CH_2Cl_2$. The organic phase was dried ($Na_2SO_4$) and concentrated. The resulting residue was triturated with ether to give the intermediate 14 as brown solid (0.87 g, 10% yield) and impure product (2.36 g). LCMS [M+H]$^+$ calcd for $C_{14}H_{21}N_2O_7$: 329.13; found: 329.15.

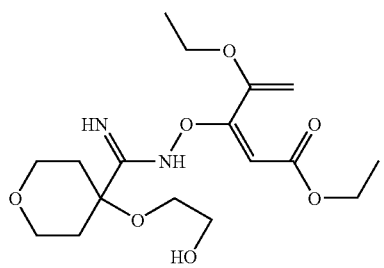

Intermediate 13

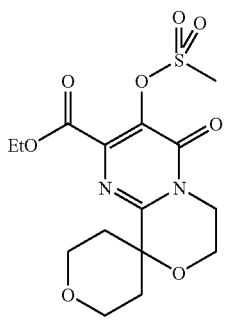

Intermediate 15

(E)-2-{[4-(2-Hydroxyethoxy)tetrahydropyran-4-carboximidoyl]-aminooxy}but-2-enedioic acid diethyl ester. A stirred mixture of intermediate 12 (6.0 g, 41.7 mmol) and $ZnI_2$ (45 mg, catalytic) was placed in water bath and to this was added trimethylsilyl cyanide (5.6 mL, 41.7 mmol) via syringe. After 18 h additional $ZnI_2$ (1.63 g, 13.76 mol %) was added and stirred for 2 h at room temperature. Proton NMR analysis showed 50% completion, so additional trimethyl cyanide (2.8 mL, 20.85 mmol) was added and stirred for 1 h. To this crude reaction mixture was added EtOH (50 mL) followed by 50% aqueous hydroxylamine (2.56 mL, 41.7 mmol) and stirred at 80° C. for 2 h. Then, the reaction mixture was cooled in an ice-water bath and diethyl acetylenedicarboxylate (7.0 mL, 56.25 mmol) was added over 5 min. Then, cold bath was removed, stirred for 15 h at room temperature, concentrated and the residue was purified by flash chromatography on silica gel column using mixtures of hexanes/EtOAc to give intermediate 13 as yellow oil (9.3 g, 60%). $^1$H-NMR (300 MHz, $CDCl_3$) δ: 5.72 (1H, d, J=22.7 Hz), 5.50 (1H, bs), 5.29 (1H, bs), 4.33-4.23 (2H, m), 4.19-4.04 (2H, m), 3.95-3.87 (1H, m), 3.79-3.63 (6H, m), 3.43-3.39 (2H, m), 2.15-1.74 (4H, m), 1.35-1.19 (6H, m). LCMS [M+H]$^+$ calcd for $C_{16}H_{27}N_2O_8$: 375.17; found: 375.19.

To a stirred solution of intermediate 14 (0.86 g, 2.6 mmol) in THF (10 mL) at 0° C. was added methanesulfonyl chloride (0.613 mL, 7.9 mmol) followed by triethylamine (1.07 mL, 7.9 mmol). The mixture stirred for 4 h while gradually warming to room temp. before diluting with EtOAc. The mixture was washed with water, brine and dried ($Na_2SO_4$) and concentrated to give dark oil. This was dissolved in EtOH (20 mL) and THF (10 mL) and added potassium carbonate (0.56 g, 4.04 mmol). The mixture was stirred at room temp for 18 h, diluted with EtOAc (200 mL) and the solids were removed by filtration. The solution was concentrated and the residue was triturated with methanol. Filtration gave the intermediate 15 as a white solid (0.23 g, 23%). $^1$H-NMR (300 MHz, $CDCl_3$) δ: 4.41 (2H, q, J=7.2 Hz), 4.03-3.98 (4H, m), 3.88-3.82 (2H, m), 3.74 (2H, t, J=11.2 Hz), 3.50 (3H, s), 2.44 (2H, dt, J=13.1, 4.9 Hz), 1.76 (2H, d, J=13.9 Hz), 1.38 (3H, t, J=7.1 Hz). LCMS [M+H]$^+$ calcd for $C_{15}H_{21}N_2O_8S_3$: 389.10; found: 389.13.

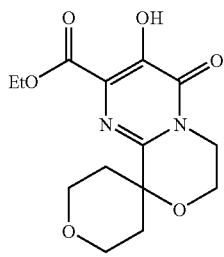

Intermediate 16

To a suspension of Intermediate 15 (1.1 g, 2.8 mmol) in EtOH (20 mL) was added sodium ethoxide (0.25 g, 3.66 mmol) and the resulting mixture was refluxed for 1 hr, cooled and concentrated. The residue was partitioned between EtOAc and water and the aqueous phase was made acidic with 1 N HCl and extracted with EtOAc. All organic phases were combined and washed with brine, dried ($Na_2SO_4$) and concentrated. The residue was triturated with $Et_2O$ and the title compound was collected by filtration as a white solid (0.84 g, 97% yield). $^1$H-NMR (300 MHz, $CDCl_3$) δ: 10.62 (1H, s), 4.42 (2H, q, J=7.2 Hz), 4.00 (4H, s), 3.89-3.84 (2H, m), 3.76 (2H, t, J=11.8, 1.9 Hz), 2.41 (2H, td, J=1.3, 5.5 Hz), 1.75 (2H, dd, J=13.9, 1.8 Hz), 1.41 (3H, t, J=7.1 Hz). LCMS $[M+H]^+$ calcd for $C_{14}H_{19}N_2O_6$: 311.12; found: 311.21.

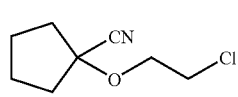

Intermediate 17

1-(2-chloroethoxy)cyclopentanecarbonitrile: To a stirred mixture of cyclopentanone ethylene ketal (128.17 g, 1 mole) and trimethylsilyl cyanide (100 g, 1 mole) at 5° C. was added zinc iodide (1.3 g, 4 mmol) at once. After 1 h, the cold bath was removed was left at room temperature overnight (18 h). To this was added 2N aq. HCl (500 mL) and MeOH (100 mL) and stirred for 1 h at room temperature. Then, the reaction mixture was transferred to separatory funnel and extracted with CH2Cl2 (4×250 mL). The combined CH2Cl2 extracts dried (Na2SO4), filtered and concentrated to give brown liquid.

A solution of above brown liquid in CH2Cl2 (200 mL) was added via cannula to a stirred solution of thionyl chloride (91.2 mL, 1.25 mole) in CH2Cl2 (250 mL) over 1 h. The addition flask was rinsed with CH2Cl2 (50 mL) and added to the reaction mixture. The resulting brown reaction mixture was refluxed for 3 h, cooled and concentrated to give dark liquid. This was diluted with ether (250 mL), washed with water (2×100 mL), sat. NaHCO3 (2×100 mL), dried (Na2SO4), filtered and concentrated to give dark-brown liquid which upon distillation provided title compound as colorless liquid (129.146 g, 74.4%, BP 68-71° C. @ 0.8 mmHg). $^1$HNMR (500 MHz, $CDCl_3$) δ: 3.79 (2H, t, J=5.5 Hz), 3.61 (2H, t, J=5.5 Hz), 2.16-1.99 (4H, m), 1.85-1.71 (4H, m).

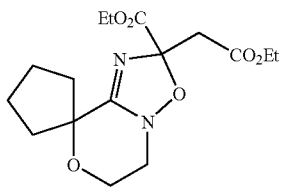

Intermediate 18

A mixture of intermediate 17 (129.14 g, 0.7437 mole), 50% aq. hydroxylamine (54.7 mL, 0.8925 mole) and Na2CO3 (31.532 g, 0.2975 mole) in MeOH/H2O (2:1, 500 mL) was stirred at room temperature for 6 h and 65° C. for 2 h. The resulting clear reaction mixture was cooled and concentrated under reduced pressure. The resulting residue was re-dissolved in EtOH/H2O (1:3, 500 mL), cooled in an ice-water bath and treated with diethyl acetylenedicarboxylate (119.1 mL, 0.7437 mol) over 15 minutes. After stirring 2 h at room temperature, the reaction mixture was diluted with ether (500 mL), aq. layer drained and organic layer washed with water (2×100 mL), brine (100 mL), dried (Na2SO4), filtered and concentrated to give yellow oil. Flash chromatography on silica gel column using mixtures of 10-30% EtOAc/Hex provide pure product as yellow liquid (196 g, 77.43%). $^1$HNMR (500 MHz, $CDCl_3$) δ: 4.36-4.20 (2H, m), 4.18-4.12 (2H, m), 3.99-3.90 (2H, m), 3.59-3.56 (1H, m), 3.51-3.47 (1H, m), 3.30 (1H, d, $J_{AB}$=16.2 Hz), 2.92 (1H, d, $J_{AB}$=16.2 Hz), 2.27-2.21 (1H, m), 2.13-2.07 (1H, m), 2.01-1.91 (2H, m), 1.79-1.68 (2H, m), 1.29 (3H, t, J=7.0 Hz), 1.24 (3H, t, J=7.0 Hz). HRMS (M+H) calcd. for $C_{16}H_{25}N_2O_6$: 341.1713, found: 341.1711.

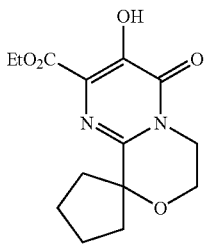

Intermediate 19

A solution of intermediate 18 (196 g, 0.5758 mole) in 1,2,4-trimethylbenzene (1.5 Lit.) was heated at 155° C. for 7 h and the dark reaction mixture was allowed to slowly cool to room temperature. The crystallized product was filtered and washed with hexanes to afford light brown powder (58.622 g). The filtrate was concentrated and the resulting residue was triturated to afford additional 38.484 g of product as light brown powder. The filtrate again concentrated and the resulting dark residue was taken up in ether (500 mL) and extracted with 0.5 M aq. Na2CO3 (2×200 mL). The organic layer discarded and combine aq. layers carefully acidified with conc. HCl (40 mL). The precipitated product was filtered and dried to product as yellow powder (6.1876 g). The combined yield was 103.2936 g (61%). $^1$H NMR (500 MHz, $CDCl_3$) δ: 10.49 (1H, s), 4.44 (2H, q, J=7.0 Hz), 4.03-3.97 (4H, m), 2.28-2.22 (2H, m), 2.06-2.01 (2H, m), 1.93-1.81 (4H, m), 1.42 (3H, t, J=7.0 Hz). HRMS (M+H) calcd for $C_{14}H_{19}N_2O_5$: 295.1294; found: 295.1293.

Intermediate 20

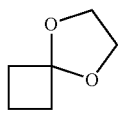

5,8-Dioxa-spiro[3.4]octane. A solution of cyclobutanone (7.7 g, 0.11 mol), ethylene glycol (6.82 g, 0.11 mol) and p-toluenesulfonic acid mono hydrate (200 mg, 1 mmol) in benzene (200 mL) was heated at reflux with a Dean-Stark trap for 14 hrs. After cooling, the mixture was washed with aqueous sodium bicarbonate solution (saturated, 15 mL), then with brine and dried (magnesium sulfate), filtered and concentrated to obtain 9.37 g (82%) of intermediate 24 as a colorless liquid: $^1$H NMR (CDCl$_3$, 500 MHz) δ: 3.87 (4H, s), 2.31 (4H, t, J=8 Hz), 1.67 (2H, qt, J=8 Hz); $^{13}$C NMR (CDCl$_3$, 125.77 Hz) δ: 109.08, 63.87, 35.58, 11.42.

Intermediate 21

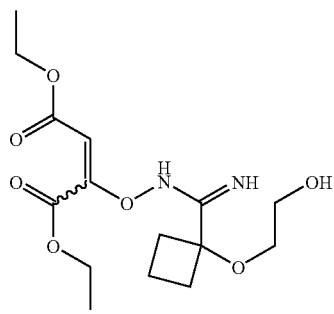

2-{[1-(2-hydroxyethoxy)cyclobutanecarboximidoyl]-aminooxy}but-2-enedioic acid diethyl ester. To a mixture of intermediate 20 (5.70 g, 50 mmol) and trimethylsilyl cyanide (5.05 g, 50 mmol) was added a catalytic amount of ZnI$_2$ (12 mg) in a cool water bath of ~10° C. and the mixture stirred at room temperature for 5 hrs to obtain 10.7 g of 1-(2-trimethylsilanyloxyethoxy)cyclobutanecarbonitrile as a mobile oil: $^1$NMR (CDCl$_3$, 500 MHz) δ: 3.75 (2H, t, J=5 Hz), 3.55 (2H, t, J=5 Hz), 2.51-2.56 (2H, m), 2.30-2.37 (2H, m), 1.91-1.98 (2H, m), 0.124 (9H, s); $^{13}$C NMR (CDCl$_3$, 125.77 Hz) δ: 120.43, 72.05, 67.71, 61.49, 34.02, 12.91, −0.29. LC/MS m/z 142 (M+H—SiMe$_3$).

A solution of 1-(2-trimethylsilanyloxyethoxy)cyclobutanecarbonitrile (3.5 g, 16.4 mmol) and 50% aqueous hydroxylamine (1.08 g, 16.4 mmol) in EtOH (16 mL) was stirred in an oil bath heated at 80° C. for 2.5 hrs and then cooled to room temperature. To a solution was added drop-wise diethyl acetylenedicarboxylate (2.93 g, 17.2 mmol) in an ice-bath and the mixture stirred at room temperature for 5 hrs. This mixture was concentrated under vacuum to obtain 6.16 g of a crude brownish oil containing intermediate 21: $^1$H NMR (500 MHz, CDCl$_3$) δ: 1.19-1.38 (6H, m) 1.72-1.86 (2H, m) 2.06-2.24 (2H, m) 2.29-2.49 (2H, m) 3.26-3.38 (2H, m) 3.63-376 (2H, m) 4.11-4.19 (2H, m) 4.24-4.38 (2H, m) 5.67 (0.25H, s) 5.85 (0.5H, s). HRMS (M+H) calcd for C$_{15}$H$_{25}$N$_2$O$_7$: 345.1662; found: 345.1648.

Intermediate 22

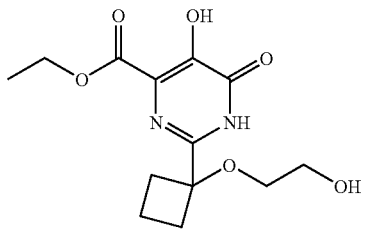

5-hydroxy-2-[1-(2-hydroxy-ethoxy)-cyclobutyl]-6-oxo-1,6-dihydro-pyrimidine-4-carboxylic acid ethyl ester. A solution of a crude intermediate 21 (5.9 g) in xylenes (30 mL) was heated at 150-155° C. for 20 h. The mixture was concentrated in vacuum and the residue re-dissolved in EtOAc (30 mL) was extracted with 1M aq. sodium carbonate solution (3×20 mL). The aqueous extracts were acidified with careful addition of concentrated HCl, and this mixture was extracted with CH$_2$Cl$_2$ (2×20 ml). The combined organic extracts were dried (Na$_2$SO$_4$), filtered and concentrated to obtain 22 (1.19 g, 24% over three steps) as brownish oil: LC/MS m/z 299 (M+H).

Intermediate 23

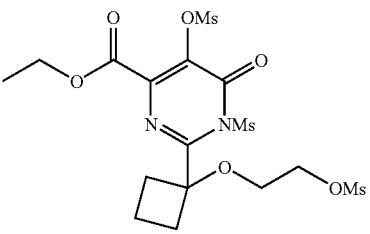

Ethyl 1-(methylsulfonyl)-5-(methylsulfonyloxy)-2-(1-(2-(methylsulfonyloxy)ethoxy)-cyclobutyl)-6-oxo-1,6-dihydropyrimidine-4-carboxylate: A cold (0° C.) solution of 22 (7.23 g, 25 mmol) in anhydrous tetrahydrofuran was treated with methanesulfonylchloride (Aldrich) by dropwise addition. The solution was warmed to room temperature and stirred for 4 hrs. The reaction was concentrated in-vacuum, and the crude product was dissolved in ethyl acetate (75 mL) and washed with saturated sodium bicarbonate solution. The organic solution was dried (sodium sulfate), filtered to remove solids, and concentrated in vacuum to give 23 as brown oil. This was used in the subsequent reaction without further purification. $^1$H NMR (500 MHz, CDCl$_3$) δ: 4.49 (2H, q, J=7.0 Hz), 4.35-4.38 (2H, m), 3.93-4.00 (1H, m), 3.66-3.67 (3H, s), 3.62-3.65 (2H, m), 3.44-3.46 (3H, s), 3.05-3.07 (3H, s), 2.74-2.82 (1H, m), 2.60-2.67 (2H, m), 2.41-2.49 (2H, m), 1.43 (3H, t, J=7.0 Hz). LCMS (M+H): 532.94.

Intermediate 24

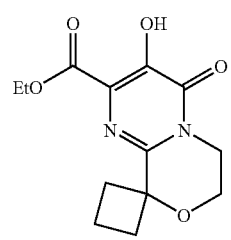

To a solution of 23 obtained above in absolute ethanol (50 mL) and anhydrous tetrahydrofuran (75 mL) was added anhydrous potassium carbonate (3.46 g, 25 mmol), and the reaction was stirred with heating (65° C.) for 20 hrs. Solvent was removed in-vacuum and the crude product was dissolved in water (150 mL) and extracted with ethyl acetate (2×100 mL). The aqueous layer was made acidic (pH ~1-2) using 6.0 N hydrochloric acid, and the resulting solid was extracted with ethyl acetate (2×75 mL). The combined extract was dried (sodium sulfate), filtered to remove solids, and concentrated to give 24 (4.30 g, 61%) as a light brown solid. $^1$H NMR (500 MHz, CDCl$_3$) δ: 10.57 (1H, s), 4.46 (2H, q, J=7.2 Hz), 3.97 (4H, s), 2.67-2.73 (2H, m), 2.27-2.33 (2H, m), 2.10-2.18 (1H, m), 1.98-2.06 (1H, m), 1.44 (3H, t, J=7.2 Hz). $^{13}$C NMR (126 MHz, CDCl$_3$) □: 169.56, 157.68, 150.41, 148.19, 125.24, 79.09, 62.63, 58.52, 42.66, 34.72, 14.18, 13.87; LC/MS (M+H): 281.13.

Intermediate 25

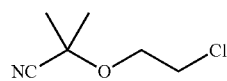

2-(2-Chloroethoxy)-2-methylpropanenitrile. (Navalokina, R. Et al J. Org. Chem. USSR (Engl. Trans.), 1980, 16, 1382-1386. 2) Ramalingam, K. U.S. Pat. No. 4,864,051, 1989). A 250 mL round bottom flask was charged with ZnCl$_2$ (68.14 g, 0.5 mole) which was then fused by heating under vacuum. After returning to room temperature the material was placed under an atmosphere of N$_2$. To this was added acetone cyanohydrin (45.66 mL, 0.5 mole) followed by 2-chloroethanol (50.24 mL, 0.75 mole) and the mixture placed in a preheated oil bath (60° C.). After stirring for 18-20 h at 60° C., the reaction mixture was cooled, diluted with water (300 mL) and washed with CH$_2$Cl$_2$ (5×100 mL). The combined CH$_2$Cl$_2$ extracts were dried (Na$_2$SO$_4$), filtered and concentrated under vacuum to afford the crude product as a yellow liquid. Purification was accomplished by vacuum distillation (10 mm Hg) using a vigreux column. The fraction boiling between 65-75° C. was collected to afford the desired product as colorless oil (47.1 g, 63.8% yield). $^1$H NMR (500 MHz, CDCl$_3$) δ: 3.85 (2H, t, J=5.8 Hz), 3.64 (2H, t, J=5.8 Hz), 1.60 (6H, s).

Intermediate 26

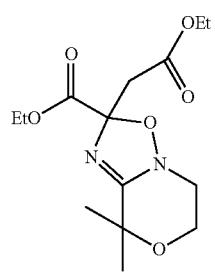

Ethyl 2-(2-ethoxy-2-oxoethyl)-8,8-dimethyl-2,5,6,8-tetrahydro-[1,2,4]oxadiazolo[3,2-c][1,4]oxazine-2-carboxylate. To a stirred solution of intermediate 25 (14.7 g, 0.10 mole) and NaI (1.5 g, 10 mmol) in ethanol (50 mL) was added an aqueous solution (50%) of hydroxylamine (18.4 g, 0.30 mole) resulting in an exothermic reaction. Following this the reaction mixture was heated at 80° C. for 2 h. Upon cooling to room temperature the solvent was removed. The resulting residue was dissolved in 1:1 ethanol/H$_2$O (100 mL) and cooled in an ice bath. To this was added diethyl acetylenedicarboxylate (17.6 mL, 0.110 mole) over 10 min. The reaction mixture was allowed to warm to room temperature and stirred for 1 h. Following this, it was diluted with ethyl acetate (250 mL), washed with H$_2$O (2×100 mL), brine (50 mL), dried over Na$_2$SO$_4$, filtered and concentrated to give the crude product as yellow oil. Flash chromatography on a silica gel column, eluting with 20-40% ethyl acetate/Hexanes, provided the title compound as viscous pale yellow oil (15.29 g, 48.6% yield). $^1$H NMR (500 MHz, CDCl$_3$) δ: 4.35-4.28 (2H, m), 4.18-4.12 (2H, m), 3.60-3.56 (1H, m), 3.51-3.47 (1H, m), 3.30 (1H, d, J=16.2 Hz), 2.94 (1H, d, J=16.2 Hz), 1.52 (3H, s), 1.51 (3H, s), 1.29 (3H, t, J=7.0 Hz), 1.24 (3H, t, J=7.0 Hz). LCMS (M+H) calcd for C$_{14}$H$_{23}$N$_2$O$_7$: 315.16; found: 315.33.

Intermediate 27

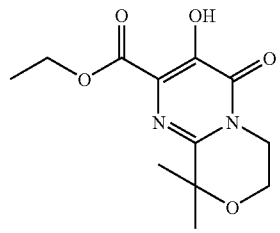

Ethyl 3-hydroxy-9,9-dimethyl-4-oxo-4,6,7,9-tetrahydropyrimido[2,1-c][1,4]oxazine-2-carboxylate. A solution of intermediate 26 (31.16 g) in 1,2,4-trimethylbenzene (200 mL) was heated at 180° C. for 5 h. The resulting dark reaction solution was cooled then concentrated to give a dark brown paste which was taken up into ethyl acetate (250 mL) and extracted with 0.5 M aq Na$_2$CO$_3$ (4×50 mL). The organic layer was discarded and the aqueous layer acidified by carefully adding conc. HCl (20 mL) before being extracted with CH$_2$Cl$_2$ (4×50 mL). The combined CH$_2$Cl$_2$ layers were dried (Na$_2$SO$_4$), filtered and concentrated to give a dark paste which was dissolved in ether (100 mL) and allowed to stand at room temperature in a open flask. The brown/light yellow solid that formed was filtered to afford the title compound. The mother liquor that contained product was re-processed to afford additional material (combined yield ~18-20% over two steps). $^1$H NMR (500 MHz, CDCl$_3$) δ: 10.55 (1H, s), 4.45 (2H, q, J=7.0 Hz), 4.02 (4H, s), 1.61 (6H, s), 1.43 (3H, t, J=7.0 Hz). HRMS (M+H) calcd for C$_{12}$H$_{17}$N$_2$O$_5$: 269.1138; found: 269.1149. Anal calcd for C$_{12}$H$_{16}$N$_2$O$_5$: C, 53.72; H, 6.01; N, 10.44. Found: C, 53.71; H, 6.04; N, 10.30.

Intermediate 28

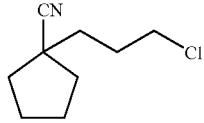

1-(3-chloropropyl)cyclopentanecarbonitrile. To a stirred solution of cyclopentanecarbonitrile (1.04 mL, 10 mmol) in THF (20 mL) at −78° C. was added LiHMDS (1M in THF, 11 mL) via syringe. After 30 min, 1-chloro-3-iodopropane (1.6 mL, 15 mmol) was added at once and slowly warmed to room temperature. After 20 h, the reaction mixture was quenched with saturated ammonium chloride (1 mL), diluted with EtOAc (100 mL), dried (MgSO$_4$), filtered and concentrated to give intermediate 28 as yellow oil which was used in the next step without further purification.

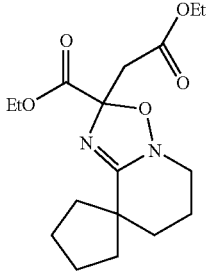

Intermediate 29

To a stirred mixture of intermediate 28 from previous experiment and hydroxylamine hydrochloride (1.39 g, 20 mmol) in 1:1 EtOH/water (30 mL) was added sodium carbonate (1.6 g, 15 mmol) over 5 min. Then, the reaction mixture was stirred to 80° C. for 15 h and concentrated to dryness. The resulting white residue was re-dissolved into 1:1 EtOH/water (30 mL) and diethyl acetylenedicarboxylate (2.4 mL, 15 mmol) was added. After 1 h, the reaction mixture was diluted with water (50 mL) and extracted with EtOAc (3×50 mL). The combined EtOAc extracts dried (Na$_2$SO$_4$), filtered and concentrated to give brown oil. Flash chromatography using 9:1, 4:1 and 7:1 Hexanes/EtOAc mixtures afforded intermediate 29 as pale yellow oil (1.03 g, 30%). $^1$H NMR (500 MHz, CDCl$_3$) δ: 4.34-4.11 (4H, m), 3.50-3.46 (1H, m), 3.38-3.34 (1H, m), 3.31 (1H, d, J=16.2 Hz), 2.91 (1H, d, J=16.2 Hz), 2.23-2.13 (2H, m), 1.95-1.89 (2H, m), 1.74-1.69 (2H, m), 1.62 (2H, t, J=5.9 Hz), 1.54-1.48 (2H, m), 1.34-1.23 (8H, m). HRMS (M+H) calcd for C$_{17}$H$_{27}$N$_2$O$_5$: 339.1920; found: 339.1923.

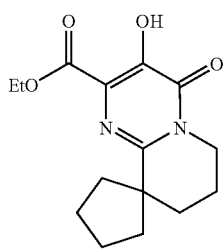

Intermediate 30

A solution of intermediate 29 (1.0 g, 2.955 mmol) in 3,4-dichlorotoluene (10 mL) was heated at 210° C. for 15 h. Then, the reaction mixture was concentrated under vacuum and the residue was purified by preparative HPLC using MeOH/water containing 0.1% TFA (gradient elution). The fractions containing the product were combined and concentrated to afford intermediate 30 as a dark paste (0.8639 g, 28.6%). $^1$H NMR (500 MHz, CDCl$_3$) δ: 10.75 (1H, br s), 4.43 (2H, q, J=7.0 Hz), 4.03 (2H, t, J=5.8 Hz), 2.25-2.20 (2H, m), 1.99-1.93 (4H, m), 1.79-1.64 (6H, m), 1.42 (3H, t, J=7.0 Hz), HRMS (M+H) calcd for C$_{15}$H$_{21}$N$_2$O$_4$: 293.1501; found: 293.1513.

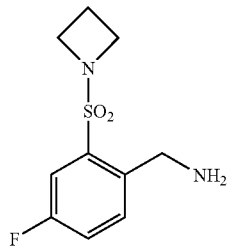

Intermediate 31

Prepared according to the procedure for Intermediate 10 using azatidine. $^1$H NMR (500 MHz, DMSO-d$_6$) δ: 1.81-2.26 (m, 2H) 3.82 (t, J=7.63 Hz, 4H) 4.30 (s, 2H) 7.66-7.82 (m, 2H) 7.90 (dd, J=8.55, 5.19 Hz, 1H) 8.52 (s, 3H); LC/MS m/z 245 (M+H).

Intermediate 32

To a solution of phenylmethanethiol (4.2 mL, 36 mmol) in toluene (40 mL) was added sodium hydride (0.96 g, 36 mmol, 90 wt %) and the mixture was stirred at room temp for 1 h. To this reaction mixture was added 2,4-difluorobenzonitrile (5.0 g, 36 mmol) and stirred at 110° C. for 3 h. The mixture was cooled to room temp, diluted with EtOAc and washed with water, sat. aq. NaHCO$_3$, dried (Na$_2$SO$_4$) and filtered. The filterate was concentrated until the product crashed out of solution. The solid was collected by filtration and washed with hexane/EtOAc (2:1) to give the title compound as white crystals (6.25 g, 71% yield). $^1$H NMR (500 MHz, CDCl$_3$) δ: 7.59 (1H, dd, J=8.5, 5.8 Hz), 7.35-7.26 (5H, m), 7.04 (1H, dd, J=8.8, 2.4 Hz), 6.92 (1H, td, J=8.1, 2.3 Hz), 4.23 (2H, s). LC/MS m/z 244 (M+H).

Intermediate 33

Chlorine was bubbled through a stirred suspension of Intermediate 32 (3.98 g, 16.4 mmol) in glacial acetic acid (20 mL) maintained above 30° C. over 30 minutes. The resulting yellow solution was diluted with water and the product was extracted with EtOAc. The combined organic phases were washed with sat., aq NaHCO$_3$ (2 X), dried (Na$_2$SO$_4$) and filtered. Concentration of filtrate gave the title compound as a sticky white solid that was used without purification. $^1$H NMR (300 MHz, CDCl$_3$) δ: 7.99 (1H, dd, J=8.4, 4.7 Hz), 7.90 (1H, dd, J=7.3, 2.6 Hz), 7.57-7.51 (1H, m).

Intermediate 34

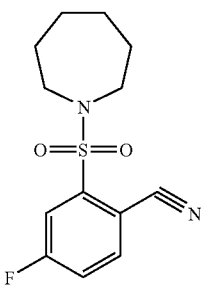

Following the procedure for Intermediate 1 using Intermediate 33 (4.00 mmol) and hexamethyleneimine (0.68 mL, 6 mmol) followed by purification by flash chromatography (10%-50% EtOAc/hexane) gave the title compound as a yellow oil (0.68 g, 61% yield). $^1$H NMR (300 MHz, CDCl$_3$) δ: 7.83 (1H, dd, J=8.6, 4.9 Hz), 7.77 (1H, dd, J=8.0, 2.6 Hz), 7.34-7.28 (1H, m), 3.43-3.39 (4H, m), 1.77-1.71 (4H, m), 1.63-1.59 (4H, m). LC/MS m/z 283 (M+H).

Intermediate 35

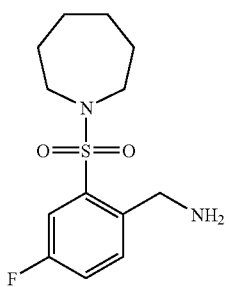

To a stirred solution mixture of LAH (2.6 mL, 2.6 mmol, 1M in THF) in THF (3 mL), was added dropwise a solution of Intermediate 34 (0.68 g, 2.4 mmol) in THF (2 mL). The resulting mixture was stirred at room temp for 1.5 h then quenched with NaOH (2 mL, 0.5 M). The solids were removed by filtration and the remaining solution was washed with water and concentrated. The residue was taken up in Et$_2$O and stirred with ethereal HCl (1N). The resulting product was dissolved in water and freeze dried to give the title compound as a sticky orange solid HCl salt (0.35 g, 45% yield). LC/MS m/z 287 (M+H).

Intermediate 36

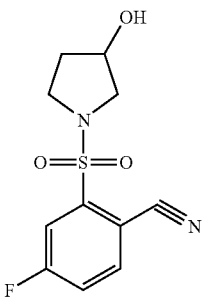

Following the procedure for Intermediate 1 using Intermediate 33 (17 mmol) and 3-pyrrolidinol (1.7 mL, 20.4 mmol) followed by flash chromatography (10%-100% EtOAc/hexane) gave the title compound as a white solid (1.08 g, 24% yield). $^1$H NMR (300 MHz, CDCl$_3$) δ: 7.85 (1H, dd, J=8.4, 5.1 Hz), 7.79 (1H, dd, J=8.0, 2.6 Hz), 7.37-7.31 (1H, m), 4.49 (1H, s), 3.61-3.45 (4H, m), 2.11-1.92 (2H, m), 1.75-1.74 (1H, m). LC/MS m/z 271 (M+H).

Intermediate 37

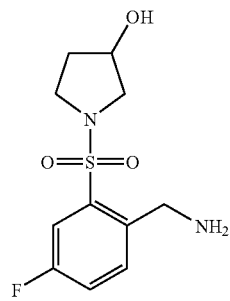

Following the procedure for Intermediate 35 using Intermediate 36 gave the title compound as a yellow solid HCl salt (0.43 g, 35% yield). LC/MS m/z 275 (M+H).

Intermediate 38

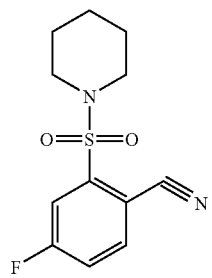

Following the procedure for Intermediate 1 using Intermediate 33 (3.8 mmol) and piperidine (0.99 mL, 10 mmol) followed by flash chromatography (10%-80% EtOAc/hexane) gave the title compound as a pale yellow solid (0.835 g, 81% yield). 1H NMR (300 MHz, CDCl$_3$) δ: 7.85 (1H, dd, J=8.6, 4.9 Hz), 7.71 (1H, dd, J=8.0, 2.6 Hz), 7.37-7.31 (1H, m), 3.25-3.21 (4H, m), 1.68-1.60 (4H, m), 1.53-1.46 (2H, m). LC/MS m/z 269 (M+H).

Intermediate 39

Following the procedure for Intermediate 35 using Intermediate 38 gave the title compound as a pale brown solid HCl salt (0.61 g, 65% yield). $^1$H NMR (300 MHz, D$_2$O) δ: 7.76-7.68 (2H, m), 7.51 (1H, td, J=8.2, 2.6 Hz), 4.44 (2H, s), 3.19-3.16 (4H, m), 1.64-1.57 (4H, m), 1.52-1.47 (2H, m). LC/MS m/z 273 (M+H).

Intermediate 40

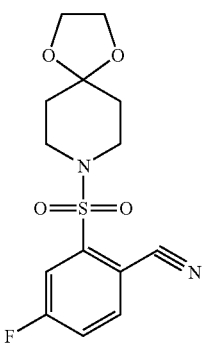

Following the procedure for Intermediate 1 using Intermediate 33 (3.8 mmol) and 1,4-dioxa-8-azaspiro[4,5]decane (1.43 g, 10 mmol) followed by flash chromatography (10%-100% EtOAc/hexane) gave the title compound as a pale yellow solid (0.877 g, 71% yield). $^1$H NMR (300 MHz, CDCl$_3$) δ: 7.85 (1H, dd, J=8.6, 4.9 Hz), 7.71 (1H, dd, J=8.0, 2.6 Hz), 7.38-7.32 (1H, m), 3.90 (4H, s), 3.41-3.47 (4H, m), 1.79-1.76 (4H, m). LC/MS m/z 327 (M+H).

Intermediate 41

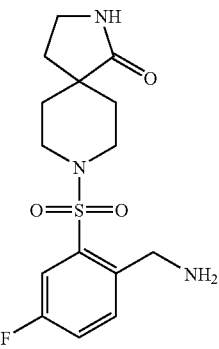

Following the procedure for Intermediate 35 using Intermediate 40 gave the title compound as a white powder HCl salt (0.88 g, 89% yield). $^1$H NMR (300 MHz, D$_2$O) δ: 7.79-7.69 (2H, m), 7.52 (1H, td, J=8.1, 2.7 Hz), 4.44 (2H, s), 3.99 (4H, s), 3.36-3.32 (4H, m), 1.86-1.82 (4H, m). LC/MS m/z 331 (M+H).

Intermediate 42

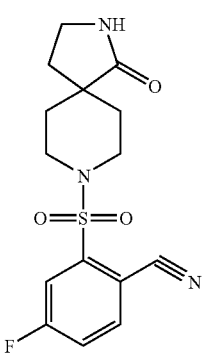

Following the procedure for Intermediate 1 using Intermediate 33 (3.8 mmol) and 4-spiro[3-(2-pyrrolidinone)]piperidine HCl (0.41 g, 2.1 mmol) followed by flash chromatography (5% MeOH/CH$_2$Cl$_2$) gave the title compound as a yellow foam (0.264 g, 37% yield). $^1$H NMR (300 MHz, CDCl$_3$) δ: 7.85 (1H, dd, J=8.6, 4.9 Hz), 7.72 (1H, dd, J=8.0, 2.6 Hz), 7.37-7.31 (1H, m), 5.71 (1H, s), 3.71-3.63 (2H, m), 3.33-3.21 (4H, m), 1.98-1.90 (4H, m), 1.63-1.55 (2H, m). LC/MS m/z 338 (M+H).

Intermediate 43

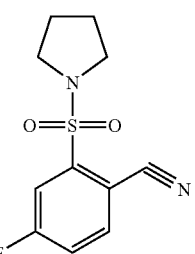

Following the procedure for Intermediate 35 using Intermediate 42 gave the title compound as a white powder HCl salt (0.265 g, 90% yield). $^1$H NMR (300 MHz, D$_2$O) δ: 7.79-7.69 (2H, m), 7.52 (1H, td, J=8.2, 2.6 Hz), 4.45 (2H, s), 3.76-3.69 (2H, m), 3.35-3.31 (2H, m), 2.90-2.81 (2H, m), 2.04-1.99 (2H, m), 1.83-1.73 (2H, m), 1.64-1.60 (2H, m). LC/MS m/z 342 (M+H).

Intermediate 44

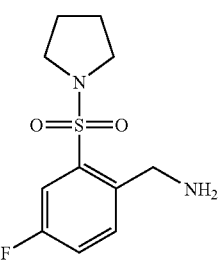

Following the procedure for Intermediate 1 using Intermediate 33 (3.8 mmol) and pyrrolidine (0.83 mL, 10 mmol) followed by flash chromatography (10%-100% EtOAc/hexane) gave the title compound as a white solid (0.57 g, 58% yield). $^1$H NMR (300 MHz, CDCl$_3$) δ: 7.85 (1H, dd, J=8.6, 4.9 Hz), 7.77 (1H, dd, J=8.0, 2.6 Hz), 7.36-7.30 (1H, m), 3.44-3.40 (4H, m), 1.2-1.88 (4H, m). LC/MS m/z 255 (M+H).

Intermediate 45

Following the procedure for Intermediate 35 using Intermediate 44 gave the title compound as a white solid HCl salt (0.265 g, 90% yield). $^1$H NMR (300 MHz, D$_2$O) δ: 7.76-7.68 (2H, m), 7.50 (1H, td, J=8.2, 2.9 Hz), 4.46 (2H, s), 3.35-3.30 (4H, s), 1.91-1.86 (4H, s). LC/MS m/z 259 (M+H).

Intermediate 46

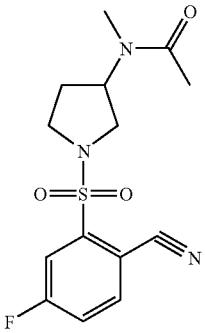

Following the procedure for Intermediate 1 using Intermediate 33 (7.7 mmol) and 3-(N-acetyl-N-methylamino)pyrrolidine (1.42 g, 10 mmol) followed by flash chromatography (30%-100% EtOAc/hexane-10% MeOH/CH$_2$Cl$_2$) gave the title compound as a yellow foam (0.887 g, 35% yield). $^1$H NMR (300 MHz, CDCl$_3$) δ: 7.87 (1H, dd, J=8.6, 4.9 Hz), 7.75 (1H, dd, J=7.7, 2.6 Hz), 7.40-7.34 (1H, m) 5.23-5.13 (1H, m), 3.76-3.69 (1H, m), 3.48-3.42 (1H, m), 3.35-3.26 (2H, m), 2.90 (3H, s), 2.11-1.98 (2H, m), 2.05 (3H, s). LC/MS m/z 326 (M+H).

Intermediate 47

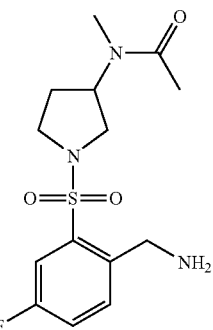

Following the procedure for Intermediate 35 using Intermediate 46 gave the title compound as a white foam HCl salt (0.947 g, >100% yield). $^1$H NMR (300 MHz, D$_2$O) δ: 7.79-7.69 (2H, m), 7.55-7.48 (1H, m), 5.00-4.89 (1H, m), 4.44 (2H, s), 3.64-3.39 (2H, m), 3.31-3.20 (2H, m), 2.89 (2H, s), 2.73 (1H, s), 2.22-2.00 (2H, m), 2.10 (1H, s), 2.05 (2H, s). LC/MS m/z 330 (M+H).

Intermediate 48

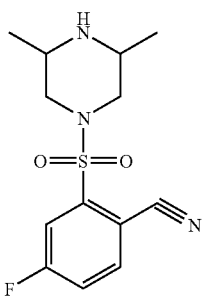

Following the procedure for Intermediate 1 using Intermediate 33 (5.5 mmol) and 2,6-dimethylpiperazine (0.81 g, 7.1 mmol) followed by flash chromatography (0%-10% MeOH/CH$_2$Cl$_2$) gave the title compound as a tan solid (1.258 g, 77% yield). $^1$H NMR (300 MHz, CDCl$_3$) δ: 7.85 (1H, dd, J=8.4, 5.1 Hz), 7.70 (1H, dd, J=8.0, 2.6 Hz), 7.38-7.32 (1H, m), 3.74-3.73 (1H, m), 3.71-3.69 (1H, m), 2.98-2.87 (2H, m), 2.18 (2H, dd, J=11.5, 10.8 Hz), 1.40 (1H, bs), 1.04 (3H, s), 1.02 (3H, s). LC/MS m/z 298 (M+H).

Intermediate 49

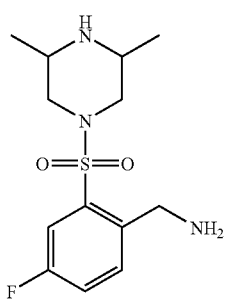

Following the procedure for Intermediate 35 using Intermediate 48 gave the title compound as a white solid HCl salt (0.711 g, 100% yield). $^1$H NMR (300 MHz, D$_2$O) δ: 7.80 (1H, dd, J=8.4, 2.9 Hz), 7.72 (1H, dd, J=8.8, 5.1 Hz), 7.56 (1H, td, J=8.2, 2.6 Hz), 4.44 (2H, s), 4.00 (2H, dd, J=13.3, 2.0 Hz), 3.59-3.48 (2H, m) 2.77 (2H, dd, J=13.2, 11.7 Hz), 1.31 (3H, s), 1.29 (3H, s). LC/MS m/z 302 (M+H).

Intermediate 50

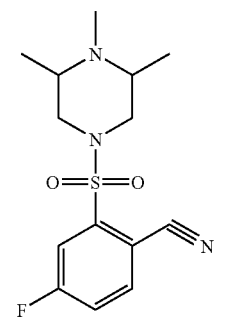

A mixture of Intermediate 48 (0.625 g, 2.1 mmol) in acetone (10 mL) and potassium carbonate (2.4 g, 15.0 mmol) was refluxed for 5 min. To this mixture was added a solution of iodomethane (0.6 g, 3 mmol) in acetone (5 mL) in 2 batches 2 h apart at reflux. After 4 h, the mixture was cooled, filtered and concentrated. The resulting residue was taken up in CH$_2$Cl$_2$, filtered and purified by flash chromatography (2% MeOH/CH$_2$Cl$_2$) to give the title compound as colorless oil (0.318 g, 49% yield). $^1$H NMR (300 MHz, CDCl$_3$) δ: 7.85 (1H, dd, J=8.6, 4.9 Hz), 7.69 (1H, dd, J=7.7, 2.6 Hz), 7.39-7.32 (1H, m), 3.66 (2H, d, J=11.7 Hz), 2.48-2.40 (2H, m), 2.34-2.28 (2H, m__, 2.21 (3H, s), 1.08 (3H, s), 1.06 (3H, s). LC/MS m/z 312 (M+H).

Intermediate 51

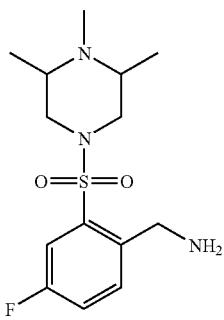

Following the procedure for Intermediate 35 using Intermediate 50 gave the title compound as a white powder HCl salt (0.381 g, 100% yield). $^1$H NMR (300 MHz, D$_2$O) δ: 7.80 (1H, dd, J=8.4, 2.9 Hz), 7.74 (1H, dd, J=8.6, 5.3 Hz), 7.56 (1H, td, J=8.5, 2.6 Hz), 4.43 (2H, s), 4.01-3.96 (2H, m), 3.55-3.47 (2H, m), 2.92 (3H, s), 3.93-2.85 2H, m), 1.38 (3H, s), 1.36 (3H, s). LC/MS m/z 316 (M+H).

Intermediate 52

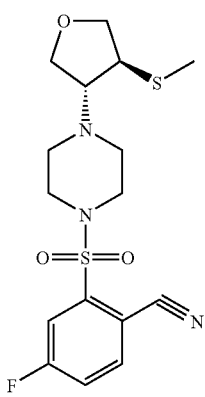

Following the procedure for Intermediate 1 using Intermediate 33 (6 mmol) and (R)-1-N-Boc-2-methylpiperazine (1.0 g, 5 mmol) followed by flash chromatography (0%-100% EtOAc/Hexane) gave the title compound as a tan solid (1.461 g, 76% yield). $^1$H NMR (300 MHz, CDCl$_3$) δ: 7.86 (1H, dd, J=8.4, 5.1 Hz), 7.70 (1H, dd, J=8.0, 2.6 Hz), 7.40-7.33 (1H, m), 4.36-4.31 (1H, m), 3.93 (1H, d, J=13.5 Hz), 3.82 (1H, dt, J=11.8, 1.6 Hz), 3.59 (1H, d, J=12.4 Hz), 3.21-3.12 (1H, m), 2.80 (1H, dd, J=12.1, 3.7 Hz), 2.59 (1H, td, J=12.0, 3.4 Hz), 1.40 (9H, s), 1.19 (3H, d, J=6.9 Hz). LC/MS m/z 284 (M+H).

Intermediate 53

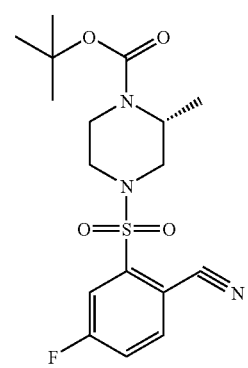

Following the procedure for Intermediate 35 using Intermediate 52 gave the title compound as a white foam HCl salt (1.27 g, 79% yield). $^1$H NMR (300 MHz, CD$_3$OD) δ: 7.80-7.71 (2H, m), 7.56 (1H, td, J=8.1, 4.0 Hz), 4.44 (2H, s), 4.40-4.36 (1H, m), 3.99-3.94 (1H, m), 3.79-3.74 (1H, m), 3.62 (1H, td, J=12.2, 1.8 Hz), 3.18 (1H, td, J=12.9, 3.4 Hz), 2.84 (1H, dd, J=12.1, 3.7 Hz), 2.65 (1H, td, J=1f2.1, 3.7 Hz), 1.45 (9H, s), 1.23 (3H, d, J=6.6 Hz). LC/MS m/z 388 (M+H).

Intermediate 54

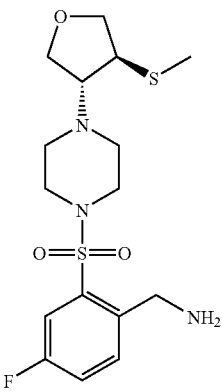

Following the procedure for Intermediate 1 using Intermediate 33 (5 mmol) and 1-((3R,4S)-4-(methylthio)tetrahydrofuran-3-yl)piperazine (0.5 g, 2.5 mmol) followed by flash chromatography (0%-100% EtOAc/Hexane) gave the title compound as a yellow solid (0.741 g, 77% yield). $^1$H NMR (300 MHz, CDCl$_3$) δ: 7.86 (1H, dd, J=8.4, 4.7 Hz), 7.71 (1H, dd, J=7.7, 2.6 Hz), 7.40-7.34 (1H, m), 4.15 (1H, t, J=8.4 Hz), 3.88-3.83 (1H, m), 3.73 (1H, bs), 3.60 (1H, dd, J=9.5, 5.8 Hz), 3.28 (4H, bs), 3.12 (1H, bs), 2.99 (1H, bs), 2.75-2.69 (2H, m), 2.58-2.53 (2H, m), 2.10 (3H, s). LC/MS m/z 386 (M+H).

Intermediate 55

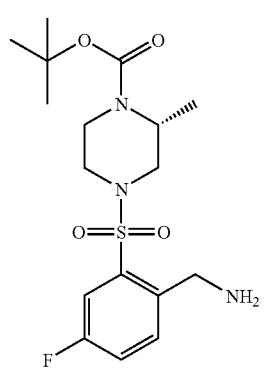

Following the procedure for Intermediate 35 using Intermediate 54 gave the title compound as a brown foam HCl salt (0.518 g, 59% yield). LC/MS m/z 390 (M+H).

Intermediate 56

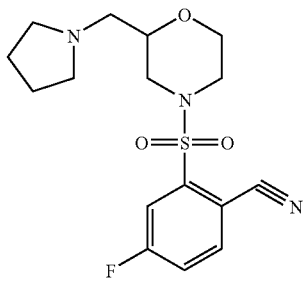

Following the procedure for Intermediate 1 using Intermediate 33 (5 mmol) and 2-(pyrrolidin-1-ylmethyl)morpholine (0.5 g, 2.9 mmol) followed by flash chromatography (5% MeOH/CH$_2$Cl$_2$) gave the title compound as a yellow oil (0.419 g, 41% yield). $^1$H NMR (300 MHz, CDCl$_3$) δ: 7.87 (1H, dd, J=8.6, 4.9 Hz), 7.72 (1H, dd, J=8.0, 2.6 Hz), 7.41-7.34 (1H, m), 3.98-3.92 (1H, m), 3.74-3.60 (4H, m), 2.86-2.77 (1H, m), 2.63-2.39 (7H, m), 1.77-1.73 (4H, m). LC/MS m/z 354 (M+H).

Intermediate 57

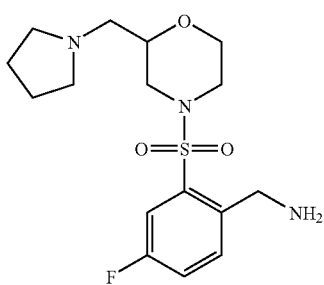

Following the procedure for Intermediate 35 using Intermediate 56 gave the title compound as a white foam HCl salt (0.450 g, 87% yield). $^1$H NMR (300 MHz, D$_2$O) δ: 7.78-7.71 (2H, m), 7.54 (1H, td, J=8.1, 2.7), 4.44-3.97 (2H, m), 3.77-3.59 (5H, m), 3.33-3.25 (2H, m), 3.15-3.06 (2H, m), 2.85 (1H, td, J=11.7, 3.3 Hz), 2.59 (1H, td, J=11.7, 10.2 Hz), 2.16-2.08 (2H, m), 2.00-1.96 (2H, m). LC/MS m/z 358 (M+H).

Intermediate 58

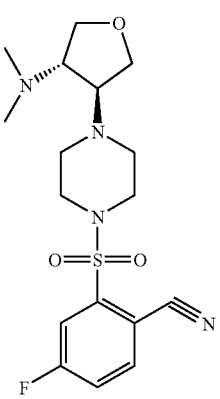

Following the procedure for Intermediate 1 using Intermediate 33 (5 mmol) and (3S,4S)-N,N-dimethyl-4-piperazin-1-yl)tetrahydrofuran-3-amine (0.5 g, 2.5 mmol) followed by flash chromatography (5% MeOH/CH$_2$Cl$_2$) gave the title compound as a yellow oil (0.363 g, 14% yield). $^1$H NMR (500 MHz, CDCl$_3$) δ: 7.88 (1H, dd, J=8.5, 4.9 Hz), 7.73 (1H, dd, J=7.8, 2.6 Hz), 7.40-7.37 (1H, m), 3.82-3.70 (4H, m), 3.30-3.28 (4H, m), 3.11 (1H, bs), 2.98 (1H, bs), 2.71-2.67 (2H, m), 2.60-2.55 (2H, m), 2.27 (6H, s). LC/MS m/z 383 (M+H).

Intermediate 59

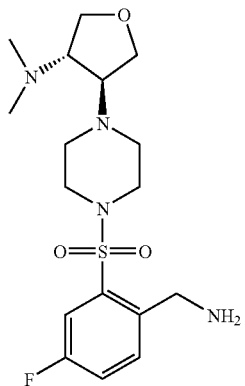

Following the procedure for Intermediate 35 using Intermediate 58 and EtOH as solvent gave the title compound as a yellow foam HCl salt (0.419 g, 89% yield). $^1$H NMR (300 MHz, D$_2$O) δ: 7.78 (1H, dd, J=8.2, 2.7 Hz), 7.72 (1H, dd, J=8.5, 5.2 Hz), 7.54 (1H, td, J=8.2, 2.6 Hz), 4.42 (2H, s), 4.41-4.39 (1H, m), 4.28-4.15 (4H, m), 4.11-4.08 (1H, m), 3.51 (4H, bs), 3.43-3.39 (2H, m), 2.94 (6H, s). LC/MS m/z 387 (M+H).

EXAMPLE 1

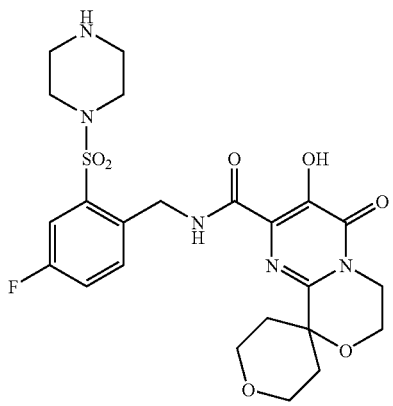

A mixture of Intermediate 20 (0.84 g, 2.7 mmol), Intermediate 6 (2.8 g, 8.1 mmol) and triethylamine (2.9 mL, 20 mmol) in EtOH/DMF (20 mL, 1:1) was stirred at 90° C. for 24 h. The mixture was concentrated and purified by chromatography (YMC Combiprep ODS-A, 30 mm×50 mm, MeOH/H2O/ 0.1% TFA) to yield the title compound as a white solid (0.63 g, 36% yield). $^1$H NMR (300 MHz, CDCl$_3$) δ: 8.50 (1H, t, J=6.6 Hz), 7.26 (1H, dd, J=8.6, 5.3 Hz), 7.53 (1H, dd, J=8.4, 2.9 Hz), 7.25 (1H, td, J=8.0, 2.6 Hz), 4.80 (2H, d, J=6.9 Hz), 3.98 (4H, s), 3.85-3.70 (4H, m) 3.31-3.28 (4H, m), 3.03-3.00

(4H, m), 2.31 (2H, td, J=13.0, 5.2 Hz), 1.74 (2H, d, J=13.2 Hz). HRMS (M+H) calcd for $C_{23}H_{29}FN_5O_7S$: 538.17718; found: 538.1751.

EXAMPLE 2

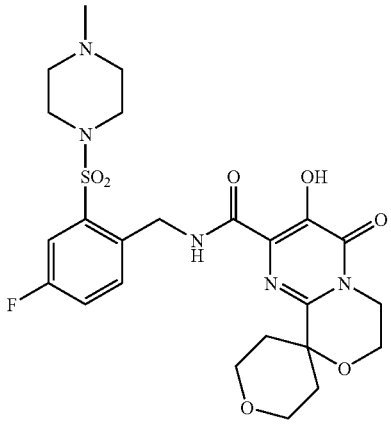

Compound 1 (0.07 g, 0.107 mmol), triethylamine (0.06 mL, 0.428 mmol) and formaldehyde (0.080 mL 37 wt % in water, 1.07 mmol) were stirred together in DCE (4 mL). To this was added solid sodium triacetoxyborohydride (0.091 g, 0.428 mmol) and the resulting mixture was stirred at room temp for 24 h. The reaction was quenched with saturated aqueous sodium bicarbonate. The aqueous phase was washed with $CH_2Cl_2$. The organic phases were combined and washed with water and dried ($Na_2SO_4$). Concentration gave the title compound as a white solid (0.054 g, 92% yield). $^1$H NMR (300 MHz, $CDCl_3$) δ: 11.90 (1H, bs), 8.52 (1H, t, J=6.8 Hz), 7.62 (1H, dd, J=8.4, 5.1 Hz), 7.51 (1H, dd, J=8.4, 2.6 Hz), 7.24 (1H, td, J=8.2, 3.0 Hz), 4.79 (2H, d, J=6.6 Hz), 3.98 (3H, s), 3.85-3.70 (4H, m), 3.34 (4H, bs), 2.58 (4H, bs), 2.36-2.26 (4H, m), 1.73 (2H, d, J=13.2 Hz), 1.56 (2H, bs). HRMS (M+H) calcd for $C_{24}H_{31}FN_5O_7S$: 552.19283; found: 552.1928. Anal calcd for $C_{24}H_{30}FN_5O_7S$: C, 52.26; H, 5.48; N, 12.70; F, 3.44; S, 5.81; found: C, 52.35; H 5.41; N, 12.44; F, 3.24; S, 5.99.

EXAMPLE 3

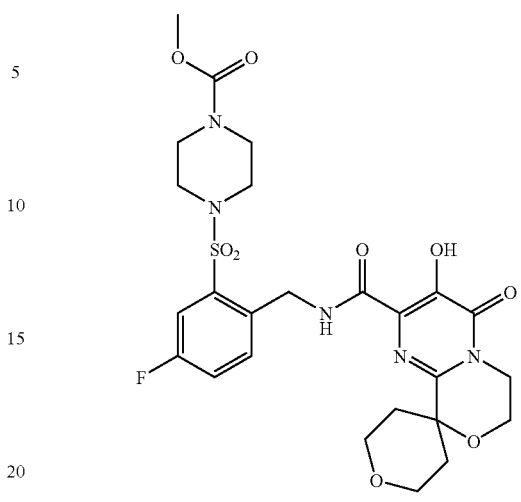

To a mixture of Compound 1 (0.07 g, 0.1 mmol) and triethylamine (0.03 mL, 0.214 mmol) in THF (3 mL) was added methyl chloroformate (0.008 mL, 0.11 mmol) and the resulting mixture was stirred at room temp for 2 h. The mixture was partitioned between EtOAc and water. The organic phase was dried ($Na_2SO_4$) and concentrated to give the title compound as a white solid (0.058 g, 98% yield). $^1$H NMR (300 MHz, $CDCl_3$) δ: 11.81 (1H, d, J=17.2 Hz), 8.49 (1H, t, J=6.9 Hz), 7.63 (1H, dd, J=8.4, 5.1 Hz), 7.50 (1H, dd, J=8.2, 2.7 Hz), 7.26 (1H, td, J=7.9, 2.8 Hz), 4.79 (2H, d, J=6.9 Hz), 3.99 (4H, s), 3.85-3.70 (4H, m), 3.67 (3H, s), 3.60-3.57 (4H, m), 3.37-3.21 (4H, m), 2.30 (2H, td, J=13.1, 5.5 Hz), 1.74 (2H, d, J=12.8 Hz). HRMS (M+H) calcd for $C_{25}H_{31}FN_5O_9S$: 596.1827; found: 596.1848.

The following examples are prepared according to the procedure outlined above using appropriate combination of intermediates and reagents

| Example | Structure | Data |
|---|---|---|
| 4 | 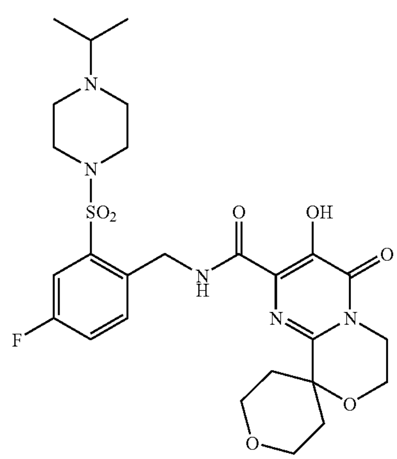 | White solid (0.0385 g, 65% yield). $^1$H NMR (300 MHz, $CDCl_3$) δ 8.52 (1H, t, J = 7.3 Hz), 7.62 (1H, dd, J = 8.4, 5.5 Hz), 7.52 (1H, dd, J = 8.2, 2.7 Hz), 7.25 (1H, td, J = 8.4, 2.2 Hz), 4.79 (2H, d, J = 7.0 Hz), 3.98 (4H, s), 3.85-3.70 (6H, m), 3.35-3.27 (2H, m), 2.66-2.62 (4H, m), 2.31 (2H, td, J = 12.8 5.2 Hz), 1.74 (2H, d, J=14.3 Hz), 1.56-1.55 (2H, m), 0.90-0.79 (1H, m), 0.56-0.51 (2H, m), 0.14-0.09 (2H, m). HRMS (M + H) calcd for $C_{27}H_{35}FN_5O_7S$: 592.2241; found: 592.2258. |

-continued

| Example | Structure | Data |
|---|---|---|
| 5 | 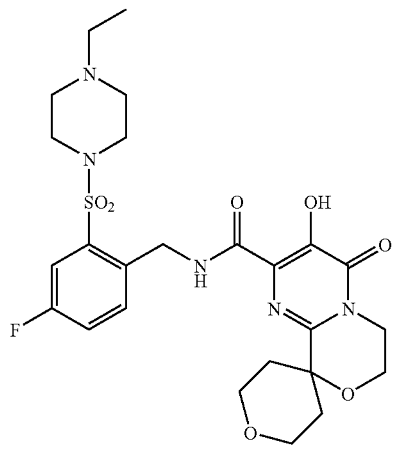 | White solid (0.0371 g, 66% yield). $^1$H NMR (300 MHz, CDCl$_3$) δ: 8.52 (1H, t, J= 6.8 Hz), 7.62 (1H, dd, J=8.6, 5.3 Hz), 7.51 (1H, dd, J = 8.2, 2.9), 7.25 (1H, td, J= 8.4, 2.6 Hz), 4.78 (2H, d, J = 6.6 Hz), 3.98 (4H, s), 3.85-3.70 (6H, m), 3.38-3.26 (2H, m), 2.64-2.48 (4H, m), 2.31 (2H, td, J=13.0, 5.4 Hz), 1.74 (2H, d, J=13.5 Hz), 1.55-1.51 (3H, m). HRMS (M + H) calcd for C$_{25}$H$_{33}$FN$_5$O$_7$S: 566.2085; found: 566.2075. Anal calcd for C$_{25}$H$_{32}$FN$_5$O$_7$S•0.75 H$_2$O: C, 51.85; H, 5.83; N, 12.09; found: C, 51.88; H, 5.89; N, 11.78. |
| 6 | 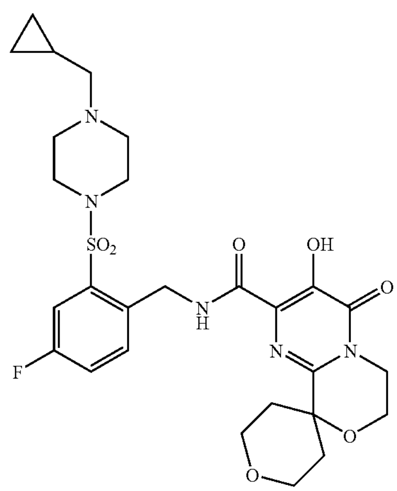 | White solid (0.0195 g, 71% yield). $^1$H NMR (300 MHz, CDCl$_3$) δ: 8.54 (1H, t, J= 5.5 Hz), 7.62 (1H, dd, J=7.9, 5.3 Hz), 7.51 (1H, dd, J=8.0, 1.5 Hz), 7.26-7.18 (1H, m), 4.78 (2H, d, J=6.6 Hz), 3.98 (4H, s), 3.81-3.70 (6H, m), 3.49-3.42 (1H, m), 3.34-3.24 (2H, m), 2.68-2.61 (2H, m), 1.73 (2H, d, J=12.8 Hz), 1.62-1.53 (2H, m), 1.08-1.02 (6H, m). HRMS (M + H) calcd for C$_{26}$H$_{35}$FN$_5$O$_7$S: 580.2241; found: 580.2227. |
| 7 | 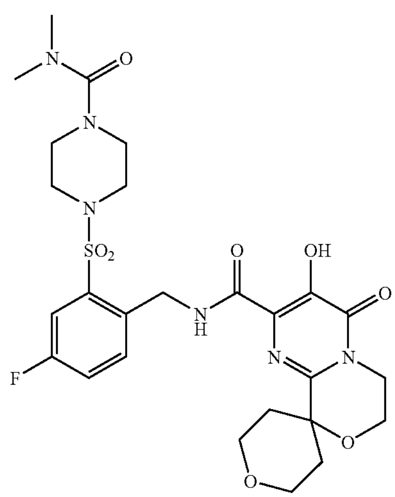 | Pale yellow solid (0.0398 g, 65% yield). $^1$H NMR (300 MHz, CDCl$_3$) δ: 11.86 (1H, bs), 8.51 (1H, t, J=6.4 Hz), 7.62 (1H, dd, J=8.6, 5.3 Hz), 7.50 (1H, dd, J= 8.4, 2.6 Hz), 7.25 (1H, td, J=8.4, 2.9 Hz), 4.78 (2H, d, J=6.6 Hz), 3.98 (4H, s), 3.86-3.70 (4H, m), 3.35-3.32 (4H, m), 3.25-3.22 (4H, m), 2.97 (6H, s), 2.31 (2H, td, J=12.9, 4.9 Hz), 1.74 (2H, d, J=13.5 Hz). HRMS (M + H) calcd for C$_{26}$H$_{34}$FN$_6$O$_8$S: 609.2143; found: 609.2146. |

| Example | Structure | Data |
|---------|-----------|------|
| 8 | 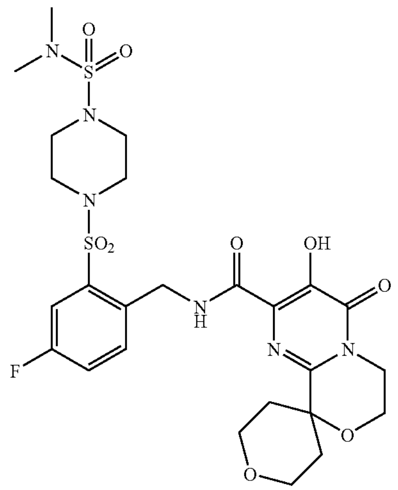 | White solid (0.0452 g, 70% yield). $^1$H NMR (300 MHz, CDCl$_3$) δ: 11.84 (1H, s), 8.47 (1H, t, J=6.6 Hz), 7.63 (1H, dd, J= 8.4, 5.5 Hz), 7.51 (1H, dd, J = 8.2, 2.7 Hz), 7.27 (1H, td, J=7.9, 2.6 Hz), 4.78 (2H, d, J=6.6 Hz), 3.99 (4H, s), 3.85-3.70 (4H, m), 3.36-3.34 (8H, m), 2.80 (6H, s), 2.30 (2H, td, J=12.9, 5.4 Hz), 1.74 (2H, d, J=13.2 Hz). HRMS (M + H) calcd for C$_{25}$H$_{34}$FN$_6$O$_9$S$_2$: 645.1813; found: 645.1837. Anal calcd for C$_{25}$H$_{33}$FN$_6$O$_9$S$_2$: C, 46.57; H, 5.15; N, 13.03; F, 2.94; S, 9.94; found: C, 46.23; H, 4.88; N, 12.76; F, 3.26; S, 10.04. |
| 9 | 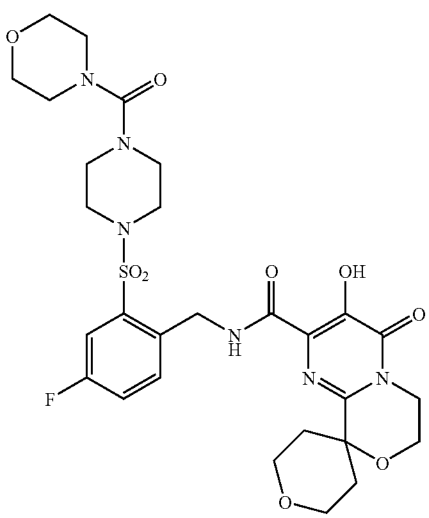 | White solid (0.0511 g, 79% yield). $^1$H NMR (300 MHz, CDCl$_3$) δ: 11.84 (1H, s), 8.50 (1H, t, J=6.8 Hz), 7.63 (1H, dd, J= 8.6, 5.3 Hz), 7.50 (1H, dd, J=8.1, 2.7 Hz), 7.06 (1H, td, J=7.7, 2.6 Hz), 4.78 (2H, d, J=6.6 Hz), 3.99 (4H, s), 3.86-3.70 (4H, m), 3.65-3.62 (4H, m), 3.39-3.36 (4H, m), 3.25-3.22 (8H, m), 2.31 (2H, td, J=13.0, 5.4 Hz), 1.74 (2H, d, J= 13.2 Hz). HRMS (M + H) calcd for C$_{28}$H$_{36}$FN$_6$O$_9$S: 651.2249; found: 651.2253. |
| 10 | 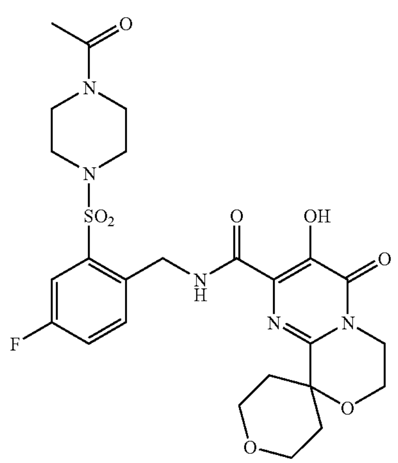 | White solid (0.0530 g, 85% yield). $^1$H NMR (300 MHz, CDCl$_3$) δ: 11.83 (1H, s), 8.47 (1H, t, J=5.5 Hz), 7.63 (1H, dd, J= 8.4, 5.5 Hz), 7.51 (1H, dd, J=8.2, 2,1 Hz), 7.27 (1H, td, J=8.0, 2.6 Hz), 4.79 (2H, d, J=6.6 Hz), 3.99 (4H, s), 3.86-3.71 (6H, m), 3.59-3.56 (2H, m), 3.29-3.21 (4H, m), 2.30 (2H, td, J=13.0, 5.4Hz), 2.07 (3H, s), 1.74 (2H, d, J=13.2 Hz). HRMS (M + H) calcd for C$_{25}$H$_{31}$FN$_5$O$_8$S: 580.1877; found: 580.1893. |

| Example | Structure | Data |
| --- | --- | --- |
| 11 | 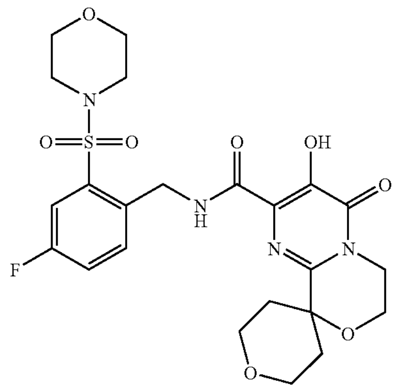 | Brown solid (0.0133 g, 19% yield). $^1$H NMR (300 MHz, CDCl$_3$) δ:11.89 (1H, s), 8.5 (1H, bs), 7.68-7.66 (1H, m), 7.56 (1H, dd, J=8.2, 2.4 Hz), 7.31-7.27 (1H, m), 4.83 (2H, d, J=6.1 Hz), 4.01 (4H, s), 3.85 (2H, dd, J=11.4, 4.1 Hz), 3.80-3.75 (6H, m), 3.25 (4H, t, J=4.4 Hz), 2.36-2.30 (2H, m), 1.76 (2H, d, J=13.1 Hz). LCMS (M + H) calcd for C$_{25}$H$_{28}$FN$_4$O$_8$S: 539.16; found: 539.27. |
| 12 | 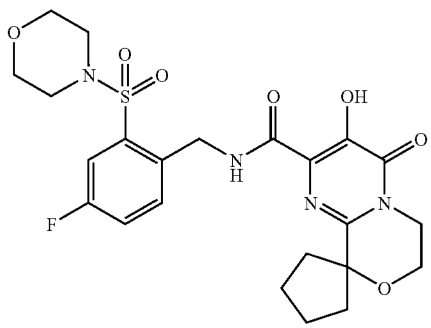 | Yield: 75%; purple solid. $^1$H NMR (500 MHz, CDCl$_3$) δ: 11.75 (1H, s), 8.54 (1H, br s), 7.69 (1H, dd, J=8.1, 5.3 Hz), 7.55 (1H, dd, J=8.1, 2.3 Hz), 7.31-7.27 (1H, m), 4.80 (2H, d, J=6.4 Hz), 4.00-3.94 (4H, m), 3.80-3.75 (4H, br s), 3.24-3.20 (4H, br s), 2.23-2.17 (2H, m), 2.06-2.00 (2H, m), 1.94-1.81 (4H, m). HRMS (M + H) calcd for C$_{23}$H$_{28}$FN$_4$O$_7$S: 523.1663; found: 523.1646. Anal calcd for C$_{23}$H$_{27}$FN$_4$O$_7$S •0.35 CH$_2$Cl$_2$: C, 50.89; H, 5.06; N, 10.18; found: C, 50.89; H, 5.12; N, 9.92. |
| 13 | 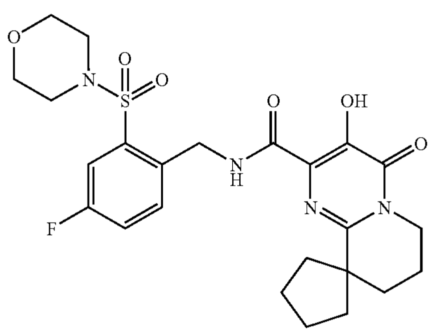 | Yield: 62%; off-white solid. $^1$H NMR (500 MHz, CDCl$_3$) δ: 11.59 (1H, s), 8.56 (1H, t, J=6.7 Hz), 7.70 (1H, dd, J =8.5, 5.2 Hz), 7.55 (1H, dd, J=8.2, 2.8 Hz), 7.29 (1H, td, J=8.2, 2.8 Hz), 4.80 (2H, d, J=6.7 Hz), 3.97 (2H, t, J=6.4 Hz), 3.77 (4H, t, J = 4.7 Hz), 3.21 (4H, t, J=4.7 Hz), 2.21-2.16 (2H, m), 1.96-1.89 (4H, m), 1.76-1.61 (6H, m). HRMS (M + H) calcd for C$_{24}$H$_{30}$FN$_4$O$_6$S: 521.1870; found: 521.1872. Anal calcd for C$_{24}$H$_{29}$FN$_4$O$_6$S•0.35 CH$_2$Cl$_2$: C, 53.15; H, 5.44; N, 10.18; found: C, 53.08; H, 5.84; N, 10.02. |
| 14 | 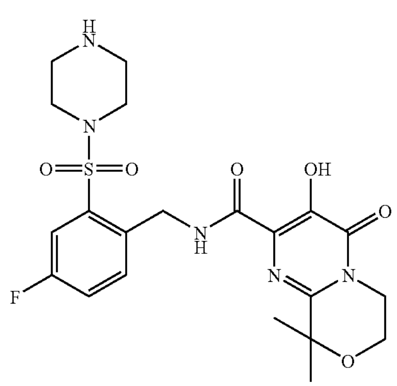 | Yellow foam TFA salt (0.70 g, 60% yield). $^1$H NMR (300 MHz, CD$_3$OD) δ: 9.24 (1H, t, J=6.4 Hz), 7.77 (1H, dd, J= 8.4, 2.6 Hz), 7.68 (1H, dd, J=8.6, 5.3 Hz), 7.49 (1H, td, J=6.2, 3.3 Hz), 4.10-4.07 (2H, m), 4.01-3.98 (2H, m), 3.59-3.55 (4H, m), 3.41-3.37 (4H, m), 1.66 (6H, s). HRMS (M + H) calcd for C$_{21}$H$_{27}$N$_5$O$_6$FS: 496.1666; found: 496.1651. |

-continued

| Example | Structure | Data |
|---|---|---|
| 15 | 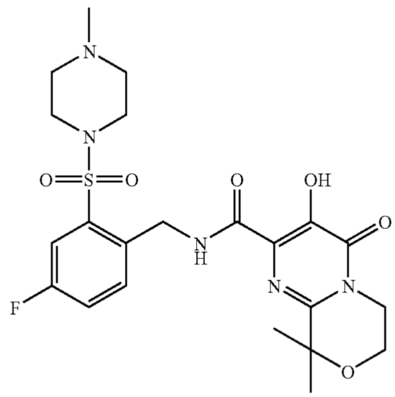 | White solid (0.032 g, 77% yield). $^1$H NMR (300 MHz, CDCl$_3$) δ: 11.78 (1H, bs), 8.61 (1H, t, J=4.6 Hz), 7.64 (1H, dd, J=8.4, 5.5 Hz), 7.53 (1H, dd, J=8.4, 2.9 Hz), 7.24 (1H, td, J=8.2, 3.1 Hz), 4.76 (2H, d, J=6.9 Hz), 3.97 (4H, s), 3.24 (4H, bs), 2.47 (4H, bs), 2.29 (3H, bs), 1.56 (6H, s). HRMS (M + H) calcd for C$_{22}$H$_{29}$N$_5$O$_6$FS: 510.1823; found: 510.1815. |
| 16 | 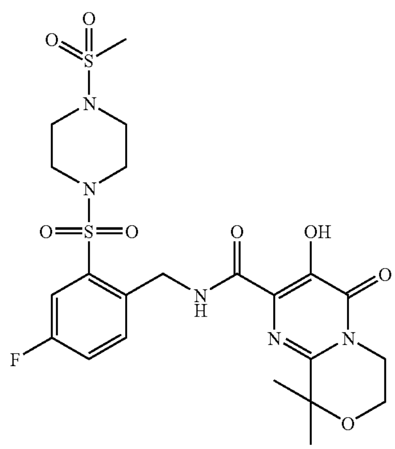 | White solid (0.418 g, 89% yield). $^1$H NMR (300 MHz, CDCl$_3$) δ: 11.72 (1H, s), 8.51 (1H, t, J=6.2 Hz), 7.67 (1H, dd, J= 8.4, 5.5 Hz), 7.54 (1H, dd, J=8.0, 2.6 Hz), 7.29 (1H, td, J=8.0, 2.7 Hz), 4.75 (2H, d, J=7.0 Hz), 3.97 (4H, s), 3.36 (8H, s), 2.80 (3H, s), 1.56 (6H, s). HRMS (M + H) calcd for C$_{22}$H$_{29}$N$_5$O$_8$FS$_2$: 574.1442; found: 574.1431. |
| 17 | 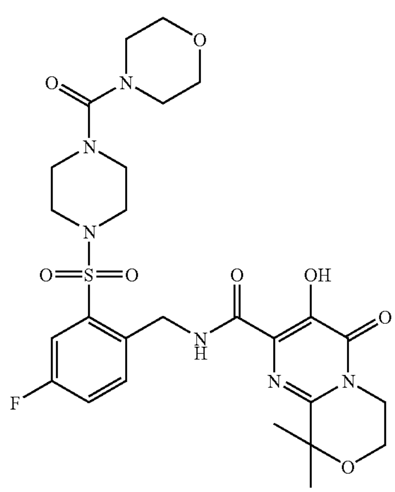 | White solid (0.026 g, 53% yield). $^1$H NMR (300 MHz, CDCl$_3$) δ: 11.74 (1H, s), 8.56 (1H, t, J=7.5 Hz), 7.65 (1H, dd, J= 8.4, 5.1 Hz), 7.51 (1H, dd, J=8.4, 2.6 Hz), 7.27 (1H, td, J=7.9, 2.6 Hz), 4.75 (2H, d, J=6.9 Hz), 3.97 (4H, s), 3.65-3.61 (4H, m), 3.38-3.34 (4H, m), 3.25-3.20 (8H, m), 1.56 (6H, s). HRMS (M + H) calcd for C$_{26}$H$_{34}$N$_6$O$_8$FS: 609.2143; found: 609.2123. |

| Example | Structure | Data |
| --- | --- | --- |
| 18 | 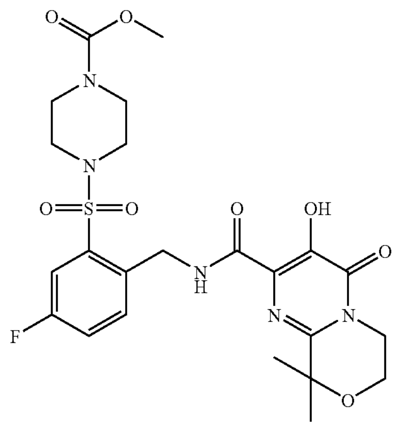 | White solid (0.031 g, 68% yield). $^1$H NMR (300 MHz, CDCl$_3$) δ:11.74 (1H, s), 8.56 (1H, t, J=6.8 Hz), 7.66 (1H, dd, J=8.6, 5.3 Hz), 7.52 (1H, dd, J=8.4, 2.6 Hz), 7.27 (1H, td, J=7.9, 2.6 Hz), 4.75 (2H, d, J=6.6 Hz), 3.97 (4H, s), 3.67 (3H, s), 3.59-3.56 (4H, m), 3.21-3.18 (4H, m), 1.56 (6H, s). HRMS (M + H) calcd for C$_{23}$H$_{29}$N$_5$O$_8$FS: 554.1721; found: 554.1713. |
| 19 | 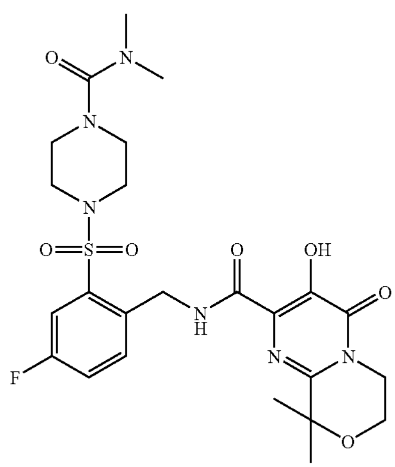 | White solid (0.0277 g, 60% yield). $^1$H NMR (300 MHz, CDCl$_3$) δ: 11.76 (1H, s), 8.58 (1H, t, J=6.6 Hz), 7.65 (1H, dd, J = 8.4, 5.5 Hz), 7.51 (1H, dd, J=8.2, 2.7 Hz), 7.26 (1H, td, J=8.2, 2.6 Hz), 4.75 (2H, d, J=6.9 Hz), 3.97 (4H, s), 3.34-3.31 (4H, m), 3.23-3.19 (4H, m), 2.79 (6H, s), 1.56 (6H, s). HRMS (M + H) calcd for C$_{24}$H$_{32}$N$_6$O$_7$FS: 567.2037; found: 567.2055. |
| 20 | 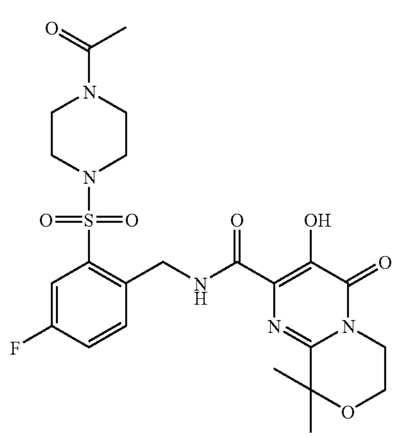 | White solid (0.021 g, 48% yield). $^1$H NMR (300 MHz, CDCl$_3$) δ: 11.73 (1H, s), 8.55 (1H, t, J=6.8 Hz), 7.66 (1H, dd, J=8.4, 5.1 Hz), 7.52 (1H, dd, J=8.2, 2.7 Hz), 7.27 (1H, td, J=8.0, 2.7 Hz), 4.76 (2H, d, J=6.9 Hz), 3.97 (4H, s), 3.73-3.70 (2H, m), 2.58-3.55 (2H, m), 3.26-3.18 (4H, m), 2.07 (3H, s), 1.56 (6H, s). HRMS (M + H) calcd for C$_{23}$H$_{29}$N$_5$O$_7$FS: 538.1772; found: 538.1778. |

| Example | Structure | Data |
|---|---|---|
| 21 | 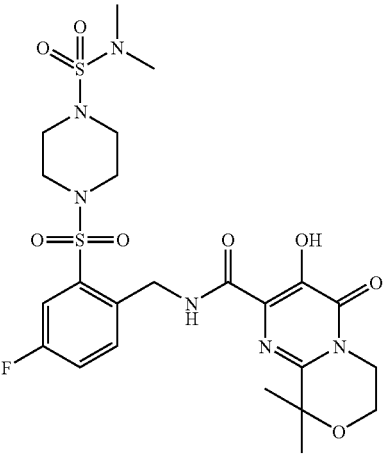 | White solid (0.014 g, 29% yield). $^1$H NMR (300 MHz, CDCl$_3$) δ: 11.75 (1H, s), 8.55-8.53 (1H, m), 7.70-7.66 (1H, m), 7.56-7.54 (1H, m), 7.31-7.29 (1H, m), 4.78 (2H, d, J=6.7 Hz), 3.99 (4H, s), 3.37 (4H, s), 3.33 (4H, s), 2.81 (6H, s), 1.58 (6H, s). HRMS (M + H) calcd for C$_{23}$H$_{32}$N$_6$O$_8$FS$_2$: 603.1707; found: 603.1716. |
| 22 | 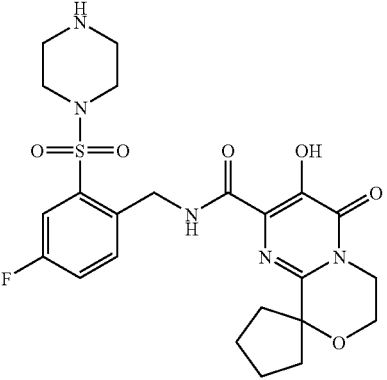 | Brown foam (79% yield). LCMS (M + H) calcd for C$_{23}$H$_{29}$N$_5$O$_6$FS: 522.18; found: 522.16. |
| 23 | 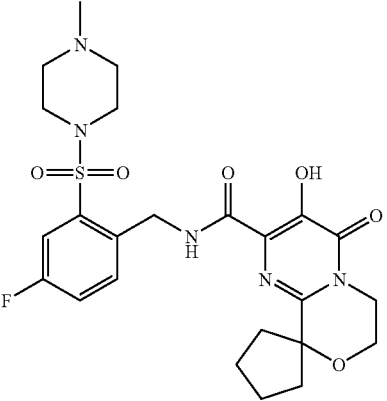 | Yellow foam (0.0.1133g, 54% yield). $^1$H NMR (300 MHz, CDCl$_3$) δ: 8.38 (1H, t, J= 6.8 Hz), 7.64 (1H, dd, J=8.4, 5.1 Hz), 7.56 (1H, dd, J=8.0, 2.6 Hz), 7.31 (1H, td, J=8.0, 2.7 Hz), 4.72 (2H, d, J=6.9 Hz), 3.99-3.89 (6H, m), 3.66-3.62 (2H, m), 3.52-3.43 (2H, m), 3.10-3.02 (2H, m), 2.87 (3H, s), 2.21-2.11 (2H, m), 2.06-1.98 (2H, m), 1.86-1.79 (4H, m). HRMS (M + H) calcd for C$_{24}$H$_{31}$N$_5$O$_6$FS: 536.1979; found: 536.1987. |

| Example | Structure | Data |
|---|---|---|
| 24 | 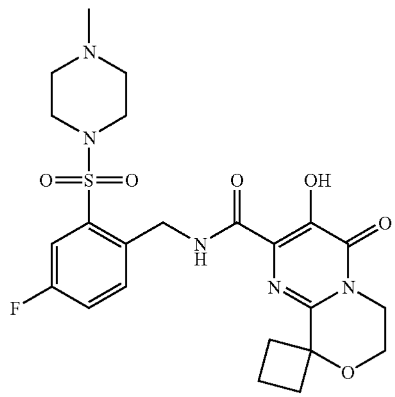 | Pale yellow foam (0.0590 g, 61% yield). $^1$H NMR (300 MHz, CDCl$_3$) δ: 8.51 (1H, t, J=6.6 Hz), 7.70 (1H, dd, J=8.6, 5.3 Hz), 7.57 (1H, dd, J=8.1, 2.9 Hz), 7.32 (1H, t, J=8.0, 2.8 Hz), 4.75 (2H, d, J=6.6 Hz), 3.93-3.90 (6H, m), 3.64-3.51 (4H, m), 3.11-3.02 (2H, m), 2.87 (3H, s), 2.68-2.59 (2H, m), 2.36-2.26 (2H, m), 2.09-1.97 (2H, m). HRMS (M + H) calcd for C$_{23}$H$_{29}$N$_5$O$_6$FS: 522.1823; found: 522.1823. |
| 25 | 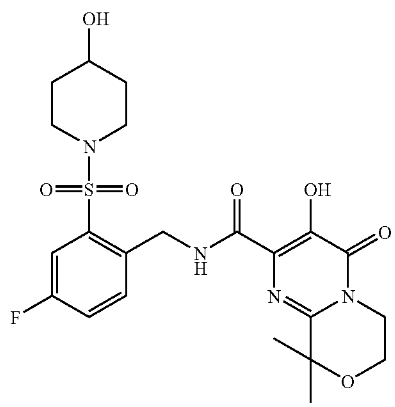 | White solid (0.0651 g, 37% yield). $^1$H NMR (300 MHz, CDCl$_3$) δ: 11.80 (1H, bs), 8.62 (1H, t, J=6.9 Hz), 7.64 (1H, dd, J=8.6, 5.3 Hz), 7.52 (1H, dd, J=8.2, 2.7 Hz), 7.23 (1H, td, J=8.0, 2.6 Hz), 4.76 (2H, d, J=6.6 Hz), 3.96 (4H, s), 3.94-3.89 (1H, m), 3.52-3.44 (2H, m), 3.18-3.10 (2H, m), 2.00-1.91 (2H, m), 1.72-1.62 (2H, m), 1.56 (6H, s). HRMS (M + H) calcd for C$_{22}$H$_{28}$N$_4$O$_7$FS: 511.1663; found: 511.1674. |
| 26 | 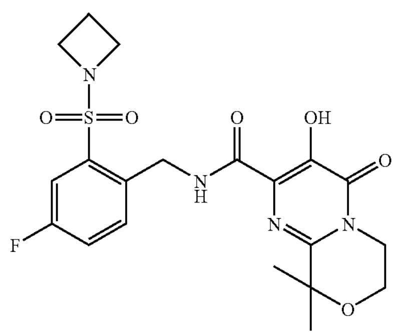 | $^1$H NMR (500 MHz, CDCl$_3$) δ: 1.49 (s, 6H) 2.14-2.39 (m, 2H) 3.83-4.10 (m, 8H) 4.82 (d, J=6.71 Hz, 2H) 7.19-7.40 (m, 2H) 7.58-7.77 (m, 1H) 8.42-8.66 (m, 1H) 11.86 (s, 1H); HRMS (M + H) calcd for C$_{20}$H$_{23}$FN$_4$O$_6$S: 467.1401; found: 467.1398. |
| 27 | 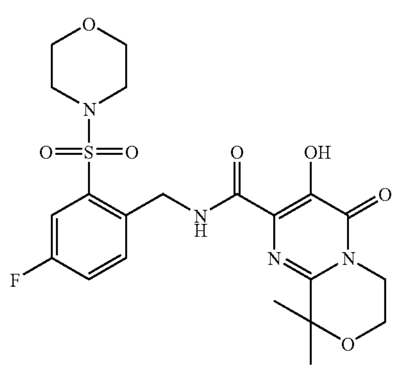 | White crystals (27% yield). $^1$H NMR (500 MHz, CDCl$_3$) δ: 11.78 (1H, s), 8.59 (1H, t, J=9.0 Hz), 7.67 (J=8.4, 5.4 Hz), 7.54 (1H, dd, J=8.4, 2.7 Hz), 7.28-7.23 (1H, m), 4.77 (2H, d, J=6.9 Hz), 3.97 (4H, s), 3.77-3.74 (4H, m), 3.22-3.18 (4H, m), 1.56 (6H, s). HRMS (M + H) calcd for C$_{21}$H$_{26}$FN$_4$O$_7$S: 497.1506; found: 497.1525. Anal calcd for C$_{21}$H$_{25}$FN$_4$O$_7$S: C, 50.80; H, 5.07; N, 11.28; found: C, 50.53; H, 4.94; N, 10.91. |

| Example | Structure | Data |
|---|---|---|
| 28 | 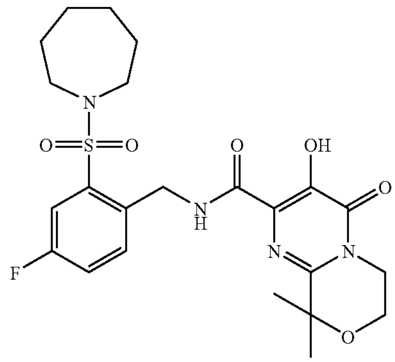 | White solid (7% yield). $^1$H NMR (300 MHz, CDCl$_3$) δ: 8.75 (1H, t, J=6.6 Hz), 7.62 (1H, dd, J=8.4, 5.1 Hz), 7.30 (1H, dd, J=8.4, 2.9 Hz), 7.20 (1H, td, J=8.2, 2.7 Hz), 4.79 (2H, d, J=6.9 Hz), 3.98 (4H, s), 3.44-3.44 (4H, m), 1.78-1.76 (4H m), 1.68-1.65 (4H, m), 1.56 (6H, s). HRMS (M + H) calcd for C$_{23}$H$_{30}$FN$_4$O$_6$S: 509.1870; found: 509.1891. |
| 29 | 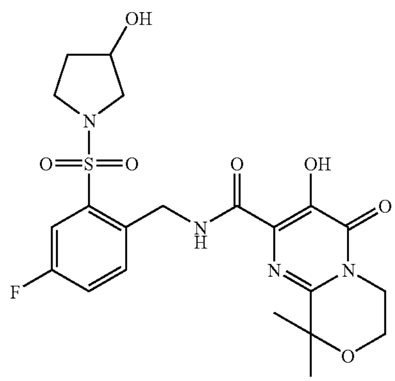 | White solid (6% yield). $^1$H NMR (300 MHz, CDCl$_3$) δ: 11.8 (1H, bs), 8.66 (1H, t, J=6.6 Hz), 7.66-7.60 (2H, m), 7.21 (1H, td, J=8.2, 2.8 Hz), 4.82 (2H, d, J= 6.9 Hz), 4.58-4.56 (1H, m), 3.96 (4H, s), 3.58-3.41 (4H, m), 2.18-1.98 (2H, m), 1.56 (6H, s). HRMS (M + H) calcd for C$_{21}$H$_{26}$FN$_4$O$_7$S: 497.1506; found: 497.1519. |
| 30 | 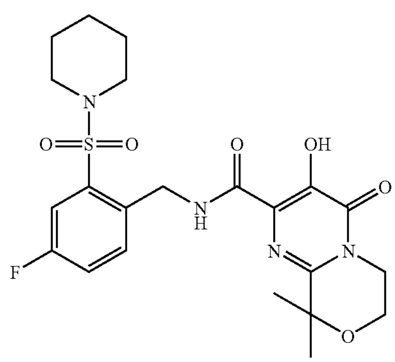 | Purple solid (8% yield). $^1$H NMR (500 MHz, CDCl$_3$) δ: 11.83 (1H, s), 8.66 (1H, bs), 7.66 (1H, dd, J=7.9, 5.2 Hz), 7.54 (1H, dd, J=8.2, 2.1 Hz), 7.27-7.22 (1H, m), 4.79 (2H, d, J=6.7 Hz), 3.99 (4H, m), 3.24-3.22 (4H, m), 1.70-1.66 (4H, m), 1.59 (6H, s), 1.59-1.56 (2H, m). HRMS (M + H) calcd for C$_{22}$H$_{28}$FN$_4$O$_6$S: 495.1714; found: 495.1714. Anal calcd for C$_{22}$H$_{27}$FN$_4$O$_6$S: C, 53.43; H, 5.50; N, 11.34; F, 3.84. found: C, 53.24; H, 5.33; N, 11.19; F, 3.81. |
| 31 | 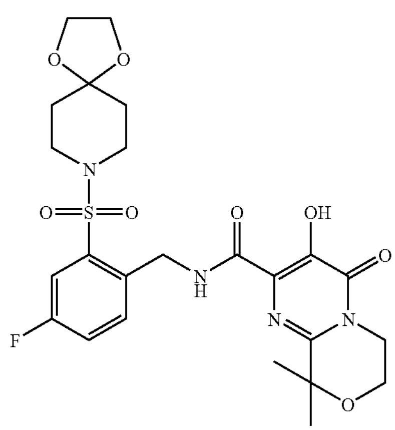 | Purple solid (6% yield). $^1$H NMR (300 MHz, CDCl$_3$) δ: 8.62 (1H, t, J=6.9 Hz), 7.64 (1H, dd, J=8.2, 5.3 Hz), 7.50 (1H, dd, J=8.2, 2.4 Hz), 7.27-7.19 (1H, m), 4.76 (2H, d, J=6.9 Hz), 3.97 (4H, s), 3.93 (4H, s), 3.38-3.35 (4H, m), 1.81-1.78 (4H, m), 1.56 (6H, s). HRMS (M + H) calcd for C$_{24}$H$_{30}$FN$_4$O$_8$S: 553.1768; found: 553.1752. Anal calcd for C$_{24}$H$_{29}$FN$_4$O$_8$S: C, 52.16; H, 5.29; N, 10.14; F, 3.43; S, 5.80. found: C, 51.92; H, 5.27; N, 9.82; F, 5.74; S, 5.74. |

| Example | Structure | Data |
|---|---|---|
| 32 | 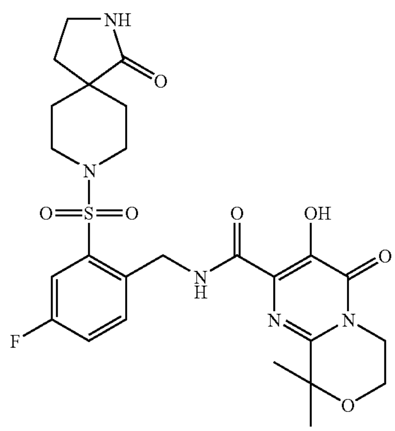 | Purple solid (20% yield). $^1$H NMR (500 MHz, CDCl$_3$) δ: 11.83 (1H, s), 8.64 (1H, bs), 7.67 (1H, bs), 7.58-7.57 (1H, m), 7.30-7.25 (1H, m), 5.63 (1H, bs), 4.79 (2H, s), 3.99 (4H, s), 3.72-3.66 (2H, m), 3.39-3.34 (2H, m), 3.22-3.20 (2H, m), 2.04-1.97 (4H, m), 1.67-1.63 (2H, m), 1.59 (6H, s). HRMS (M + H) calcd for C$_{25}$H$_{31}$FN$_5$O$_7$S: 564.1928; found: 564.1945. Anal calcd for C$_{24}$H$_{29}$FN$_4$O$_7$S•05TFA•0.6H$_2$O: C, 51.97; H, 5.43; N, 12.07; F, 3.77. found: C, 51.72; H, 5.06; N, 11.92; F, 3.87. |
| 33 | 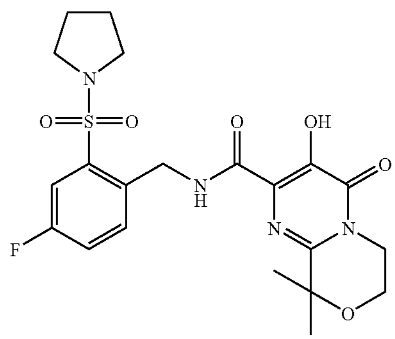 | Pale yellow solid (56% yield). $^1$H NMR (500 MHz, CDCl$_3$) δ: 11.85 (1H, s), 8.68 (1H, t, J=6.2 Hz), 7.66 (1H, dd, J=8.5, 5.2 Hz), 7.53 (1H, dd, J = 8.4, 2.6 Hz), 7.26-7.23 (1H, m), 4.82 (2H, d, J=7.0 Hz), 3.99 (4H, s), 3.40-3.38 (4H, m), 1.99-1.96(4H,m), 1.58 (6H, s). HRMS (M + H) calcd for C$_{21}$H$_{26}$FN$_4$O$_6$S: 481.1517; found: 481.1565. Anal calcd for C$_{21}$H$_{25}$FN$_4$O$_6$S: C, 52.49; H, 5.24; N, 11.66; F, 3.95. found: C, 52.23; H, 5.10; N, 11.55; F, 3.65. |
| 34 | 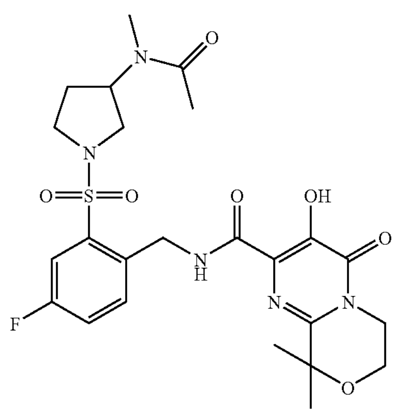 | Lavender foam (63% yield). $^1$H NMR (500 MHz, CDCl$_3$) δ: 11.79 (1H, bs), 8.60 (1H, bs), 7.70-7.67 (1H, m), 7.58 (1H, dd, J=7.9, 2.1 Hz), 7.30-7.27 (1H, m), 5.23 (1H, t, J=7.5 Hz), 4.80 (2H, d, J= 3.0 Hz), 4.00 (4H, s), 3.68-3.65 (1H, m), 3.47-3.43 (1H, m), 3.28-3.23 (2H, m), 2.96 (3H, s), 2.17-2.14 (1H, m), 2.11 (3H, m), 2.07-2.02 (1H, m), 1.59 (6H, s). HRMS (M + H) calcd for C$_{24}$H$_{31}$FN$_5$O$_7$S: 552.1928; found: 552.1915. |
| 35 | 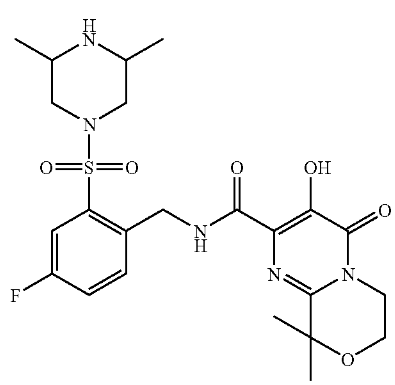 | Lavender foam TFA salt (1% yield). $^1$H NMR (300 MHz, CDCl$_3$) δ: 8.49 (1H, t, J= 6.7 Hz), 7.69 (1H, dd, J=8.5, 5.2 Hz), 7.54 (1H, dd, J=8.1, 2.4 Hz), 7.33 (1H, td, J=8.0, 2.4 Hz), 4.76 (2H, d, J=6.7 Hz), 4.00 (4H, s), 3.86-3.83 (2H, m), 3.50-3.46 (2H, m), 3.02 (2H, t, J=12.5 Hz), 1.59 (6H, s), 1.38 (3H, s), 1.37 (3H, s). HRMS (M + H) calcd for C$_{23}$H$_{31}$FN$_5$O$_6$S: 524.1979; found: 524.2003. |

| Example | Structure | Data |
| --- | --- | --- |
| 36 | 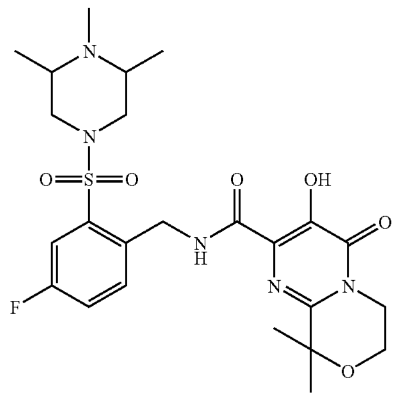 | Brown foam TFA salt (1% yield). $^1$H NMR (500 MHz, CDCl$_3$) δ: 11.79 (1H, bs), 7.67 (1H, dd, J=8.4, 5.3 Hz), 7.55-7.53 (1H, m), 7.29-7.24 (1H, m), 4.78 (2H, d, J=6.7 Hz), 3.99 (4H, s), 3.55 (2H, d, J=8.2 Hz), 2.52 (2H, bs), 2.33 (2H, bs), 2.26 (3H, s), 1.59 (6H, s). HRMS (M + H) calcd for C$_{24}$H$_{33}$FN$_5$O$_6$S: 538.2136; found: 538.2137. |
| 37 | 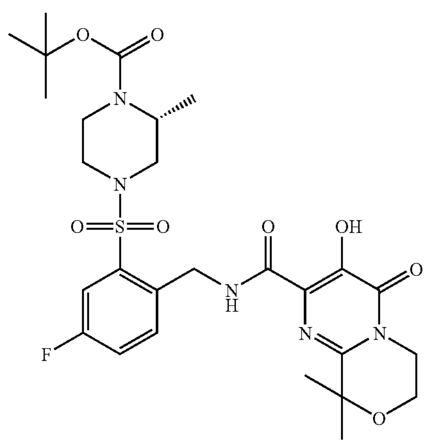 | Pale brown solid (57% yield). $^1$H NMR (300 MHz, CDCl$_3$) δ: 11.76 (1H, s), 8.59 (1H, t, J=6.9 Hz), 7.65 (1H, dd, J=8.4, 5.5 Hz), 7.47 (1H, dd, J=8.2, 2.7 Hz), 7.25 (1H, td, J=7.9, 2.7 Hz), 4.75 (2H, dd, J=7.0, 2.6 Hz), 4.38-4.32 (1H, m), 3.97 (4H, s), 3.97-3.93 (1H, m), 3.72-3.67 (1H, m), 3.49 (1H, d, J=11.7 Hz), 3.18-3.08 (1H, m), 2.87-2.81 (1H, m), 2.65 (1H, td, J=11.9, 3.3 Hz), 1.56 (6H, s), 1.41 (9H, s), 1.21 (3H, d, J=6.6 Hz). HRMS (M + H) calcd for C$_{27}$H$_{37}$FN$_5$O$_8$S: 610.2347; found: 610.2338. Anal calcd for C$_{27}$H$_{36}$FN$_5$O$_8$S: C, 53.19; H, 5.95; N, 11.48; F, 3.11; S, 5.26. found: C, 52.82; H, 5.74; N, 10.99; F, 3.36; S, 5.50. |
| 38 | 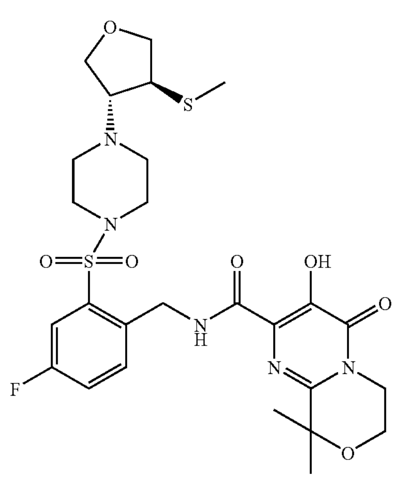 | Pale yellow foam (9% yield). $^1$H NMR (500 MHz, CDCl$_3$) δ: 11.50 (1H, bs), 8.44 (1H, t, J=6.9 Hz), 7.66 (1H, dd, J=8.5, 5.2 Hz), 7.61 (1H, dd, J=8.1, 2.6 Hz), 7.34 (1H, td, J=7.9, 2.7 Hz), 4.76 (2H, d, J=6.7 Hz), 4.37-4.32 (1H, m), 4.24 (1H, dd, J = 11.3, 2.4 Hz), 4.01 (4H, s), 3.99-3.95 (1H, m), 3.69-3.61 (6H, m), 3.45 (2H, bs), 3.31-3.29 (2H, m), 2.19 (3H, s), 1.59 (6H, s). HRMS (M + H) calcd for C$_{26}$H$_{35}$FN$_5$O$_7$S$_2$: 612.1962; found: 612.1953. |

-continued

| Example | Structure | Data |
|---|---|---|
| 39 | 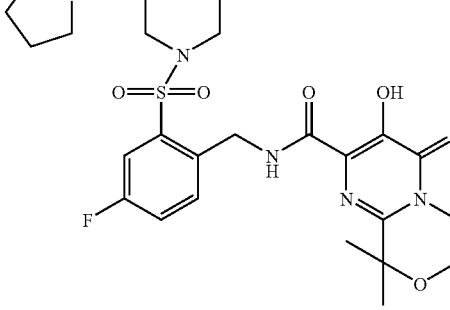 | Brown foam (41% yield). $^1$H NMR (500 MHz, CDCl$_3$) δ: 11.65 (1H, bs), 8.55 (1H, bs), 7.65 (1H, dd, J=7.3, 5.2 Hz), 7.57 (1H, d, J=7.0 Hz), 7.29 (1H, t, J=7.3 Hz), 4.76 (2H, d, J=5.5 Hz), 4.07-3.85 (8H, m), 3.74-3.61 (2H, m), 3.53 (1H, d, J=11.9 Hz), 3.34 (1H, bs), 3.07 (1H, bs), 2.97 (1H, bs), 2.89-2.85 (2H, m), 2.61 (1H, bs), 2.08 (4H, bs), 1.58 (6H, s). HRMS (M + H) calcd for C$_{26}$H$_{35}$FN$_5$O$_7$S: 580.2241; found: 580.2219. |
| 40 | 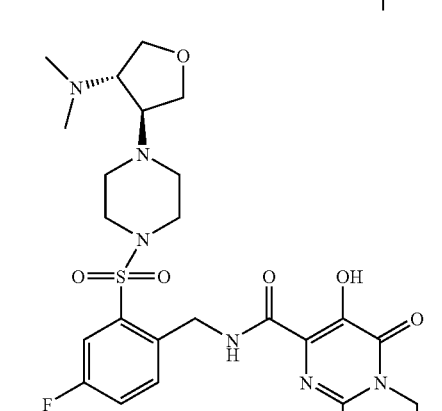 | Brown foam (39% yield). $^1$H NMR (500 MHz, CD$_3$OD) δ: 9.13 (1H, t, J=5.7 Hz), 7.69-7.66 (2H, m), 7.46-7.42 (1H, m), 4.91 (2H, s), 4.09-3.94 (9H, m), 3.67 (1H, bs), 3.33-3.25 (4H, m0, 2.95 (6H, s), 2.82-2.77 (4H, m), 1.65 (6H, s). HRMS (M + H) calcd for C$_{27}$H$_{38}$FN$_6$O$_7$S: 609.2507; found: 609.2509. |

1.22 (3H, d, J=6.4 Hz). HRMS (M+H) calcd for C$_{22}$H$_{29}$FN$_5$O$_6$S: 510.1823; found: 510.1818.

Compound 41

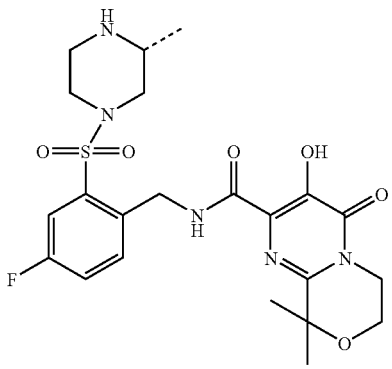

To a solution of Compound 37 (0.21 g, 0.35 mmol) in CH$_2$Cl$_2$ (2 mL) was added TFA (2 mL) and the resulting mixture was stirred at room temp for 2 h and concentrated to give the title compound as a brown foam TFA salt (0.168 g, 77% yield). $^1$H NMR (500 MHz, DMSO) δ: 7.71 (1H, dd, J=8.4, 2.4 Hz), 7.64 (1H, td, J=8.3, 2.6 Hz), 7.55 (1H, dd, J=8.7, 5.3 Hz), 4.79 (2H, s), 4.01-3.99 (2H, m), 3.86-3.84 (2H, m), 3.82-3.76 (2H, m), 3.44-3.39 (2H, m), 3.16-3.12 (1H, m), 3.03-2.98 (1H, m), 2.83-2.79 (1H, m), 1.56 (6H, s), Compound 42

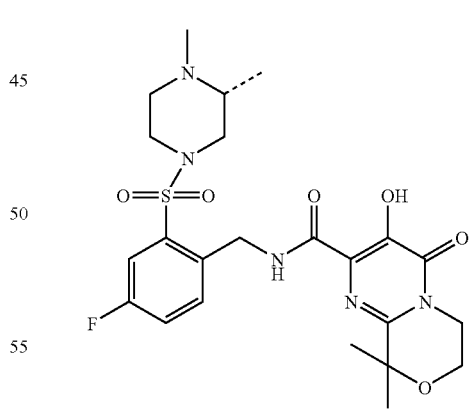

To a mixture of compound 41 (0.10 g, 0.16 mmol), triethylamine (0.07 mL, 0.5 mmol) and formaldehyde (0.12 mL, 1.6 mmol, 37 wt % in H$_2$O) in 1,2-dichloroethane (4 mL) was added sodium triacetoxyborohydride (0.106 g, 0.5 mmol). The resulting mixture was stirred at room temp for 18 h. After quenching with saturated aqueous sodium bicarbonate the aqueous phase was washed with CH$_2$Cl$_2$. The organic phases were combined and dried (Na$_2$SO$_4$) and concentrated. Purification by flash chromatography (5% MeOH/CH$_2$Cl$_2$) gave the title compound as a white solid (0.0126 g, 15% yield). $^1$H NMR (500 MHz, CDCl$_3$) δ: 11.83 (1H, bs), 8.62 (1H, t, J=6.6 Hz), 7.66 (1H, dd, J=8.5, 5.2 Hz), 7.53 (1H, dd, J=8.4, 2.6 Hz), 7.27 (1H, td, J=7.9, 2.4 Hz), 4.77 (2H, d, J=6.7 Hz), 3.99 (4H, s), 3.63-3.61 (1H, m), 3.53-3.51 (1H, m), 2.97 (1H, t, J=8.8 Hz), 2.87-2.85 (1H, m), 2.58 (1H, t, J=8.8 Hz), 2.40 (1H, t, J=10.4 hz), 2.32 (3H, s), 2.30 (1H, bs), 1.58 (6H, s). 1.09 (3H, d, J=6.1 Hz). HRMS (M+H) calcd for C$_{23}$H$_{31}$FN$_5$O$_6$S: 524.1979; found: 524.1996.

We claim:

1. A compound of formula I

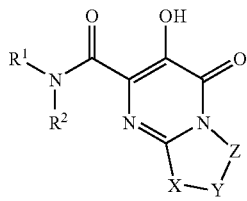

R$^1$ is (Ar$^1$)alkyl;
R$^2$ is hydrogen, alkyl, hydroxy, or alkoxy;
R$^3$ is SO$_2$N(R$^6$)(R$^7$);
R$^4$ is hydrogen, halo, hydroxy, cyano, alkyl, alkoxy, haloalkyl, or haloalkoxy;
R$^5$ is hydrogen, halo, hydroxy, cyano, alkyl, alkoxy, haloalkyl, or haloalkoxy;
R$^6$ and R$^7$ taken together with the nitrogen to which they are attached is azetidinyl, (R$^8$)-azetidinyl, pyrrolidinyl, (R$^8$)-pyrrolidinyl, piperidinyl, (R$^8$)-piperidinyl, dialkylpiperidinyl, trialkylpiperidinyl, piperazinyl, 4-(R$^9$)-piperazinyl, dialkylpiperazinyl, dialkyl-4-(R$^9$)-piperazinyl, homopiperidinyl, morpholinyl, thiomorpholinyl,

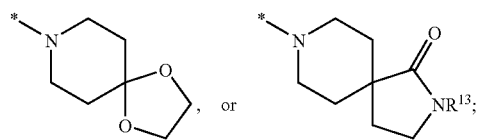

R$^8$ is alkyl, hydroxy, alkoxy, amino, alkylamino, dialkylamino, alkylCONH, alkylCON(alkyl), (methylthio)tetrahydrofuranyl, (amino)tetrahydrofuranyl, (alkylamino)tetrahydrofuranyl, (dialkylamino)tetrahydrofuranyl, azetidinyl, pyrrolidinyl, piperidinyl, piperazinyl, homopiperidinyl, morpholinyl, (azetidinyl)alkyl, (pyrrolidinyl)alkyl, (piperidinyl)alkyl, (piperazinyl)alkyl, (homopiperidinyl)alkyl, or (morpholinyl)alkyl;
R$^9$ is alkyl, (cycloalkyl)alkyl, SO$_2$R$^{10}$, or COR$^{11}$;
R$^{10}$ is hydrogen, alkyl, amino, alkylamino, dialkylamino, azetidinyl, pyrrolidinyl, piperidinyl, hydroxypiperidinyl, piperizinyl, 4-(alkyl)piperizinyl, morpholinyl, or thiomorpholinyl;
R$^{11}$ is hydrogen, alkyl, hydroxy, alkoxy, amino, alkylamino, dialkylamino, azetidinyl, pyrrolidinyl, piperidinyl, hydroxypiperidinyl, piperizinyl, 4-(alkyl)piperizinyl, morpholinyl, or thiomorpholinyl;
R$^{12}$ is hydrogen or alkyl;
R$^{13}$ is hydrogen or alkyl;

Ar$^1$ is

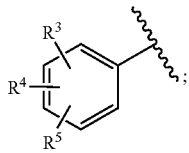

and
X-Y-Z is C(R$^{12}$)$_2$OC(R$^{12}$)$_2$C(R$^{12}$)$_2$;
or a pharmaceutically acceptable salt thereof.

2. A compound of claim 1 where
R$^6$ and R$^7$ taken together with the nitrogen to which they are attached is azetidinyl, pyrrolidinyl, piperidinyl, (R$^8$)-piperidinyl, piperazinyl, 4-(R$^9$)-piperazinyl, homopiperidinyl, morpholinyl, or thiomorpholinyl;
R$^8$ is hydroxy or alkyl; and
R$^9$ is alkyl, (cycloalkyl)alkyl, SO$_2$R$^{10}$, or COR$^{11}$.

3. A compound of claim 1 where R$^1$ is

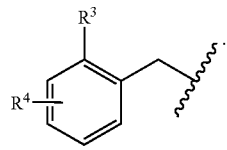

4. A compound of claim 3 where R$^4$ is hydrogen or halo.
5. A compound of claim 1 where R$^2$ is hydrogen.
6. A compound of claim 1 selected from the group consisting of

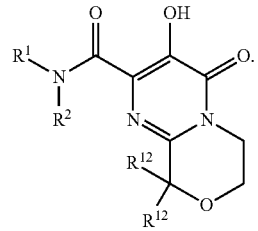

7. A compound selected from the group consisting of

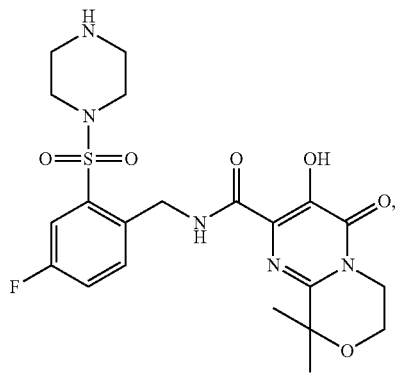

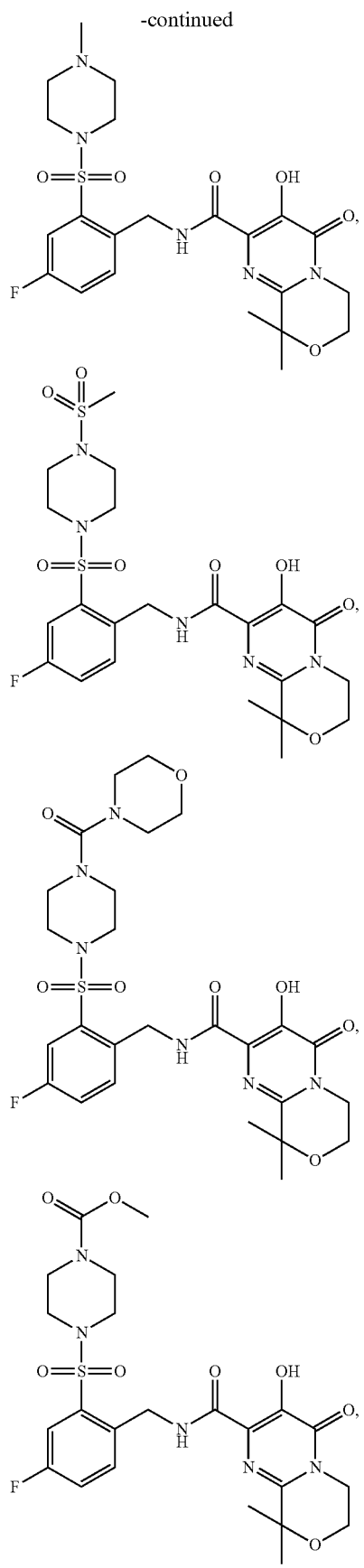
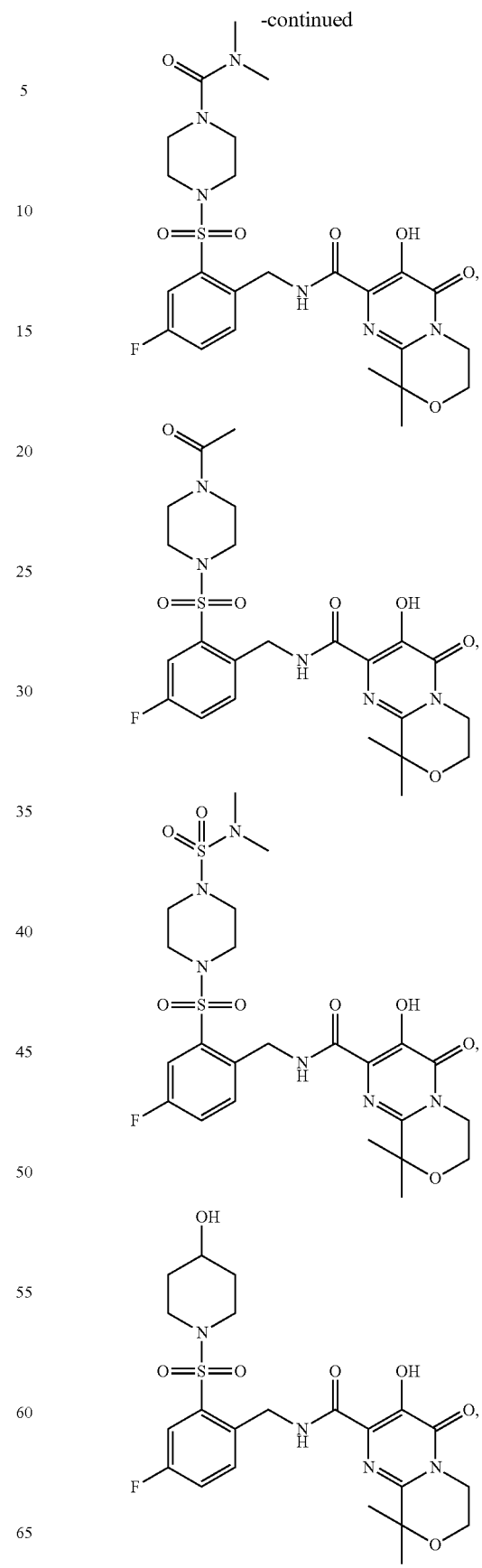

-continued
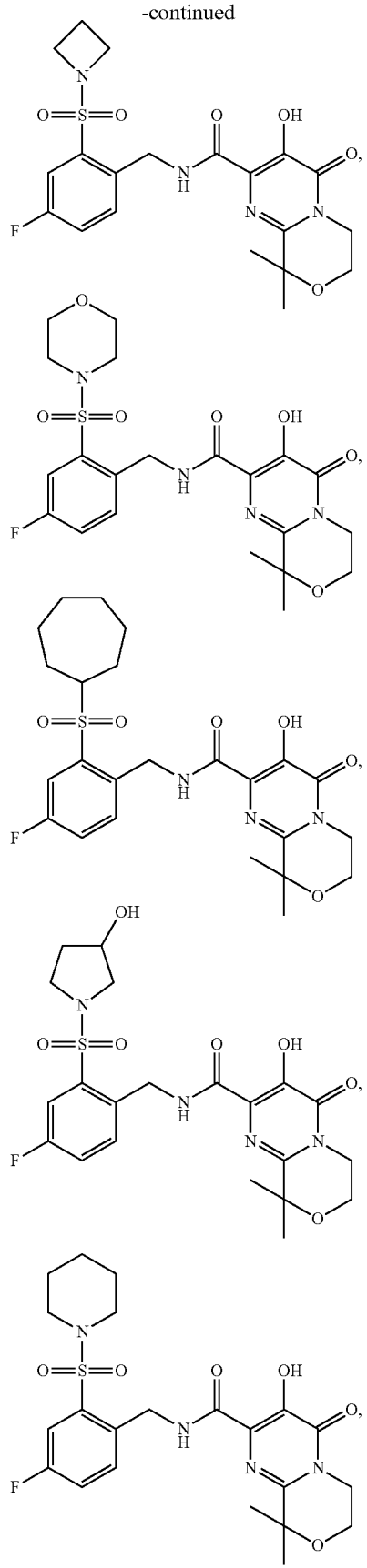
-continued
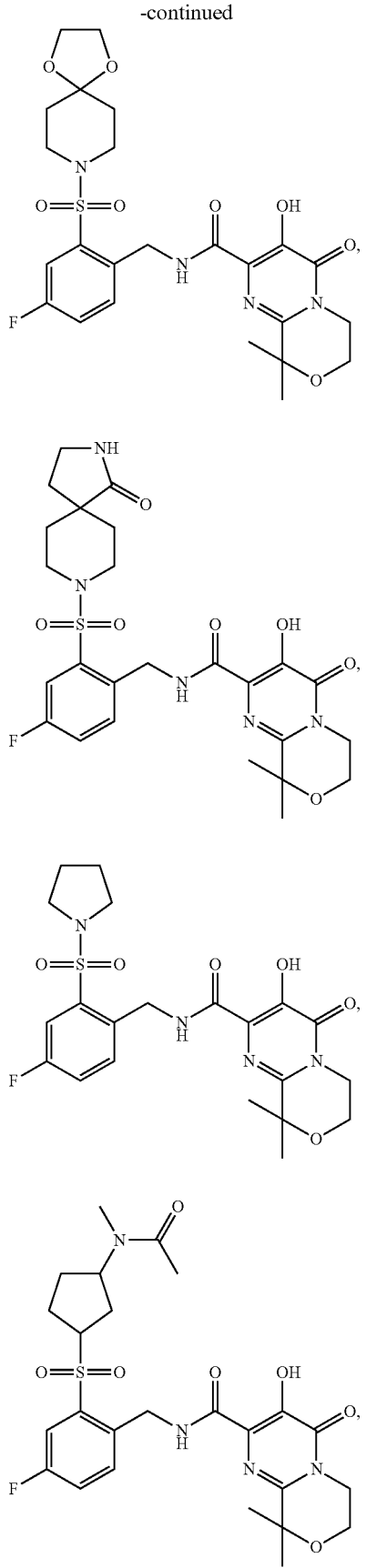

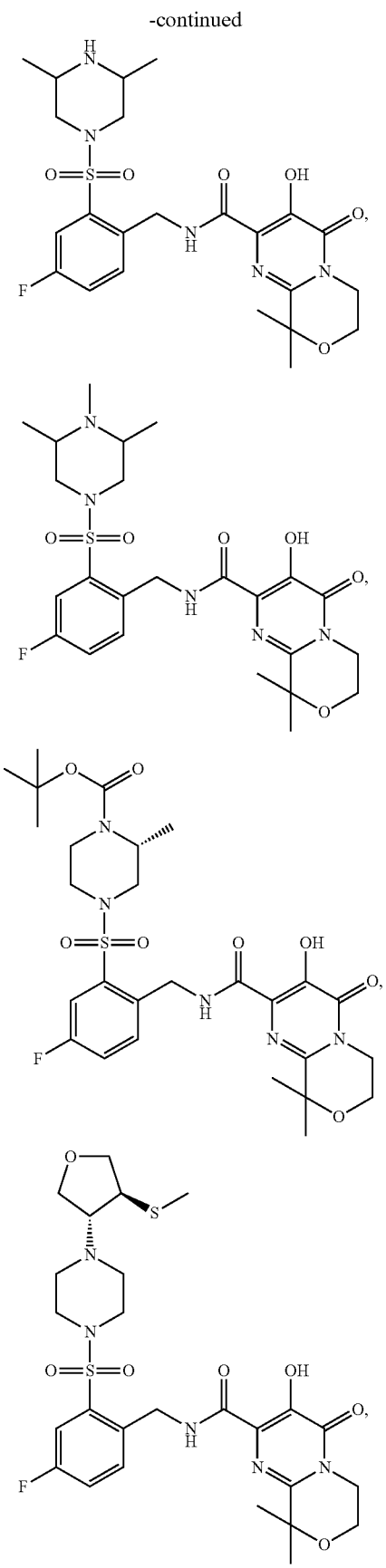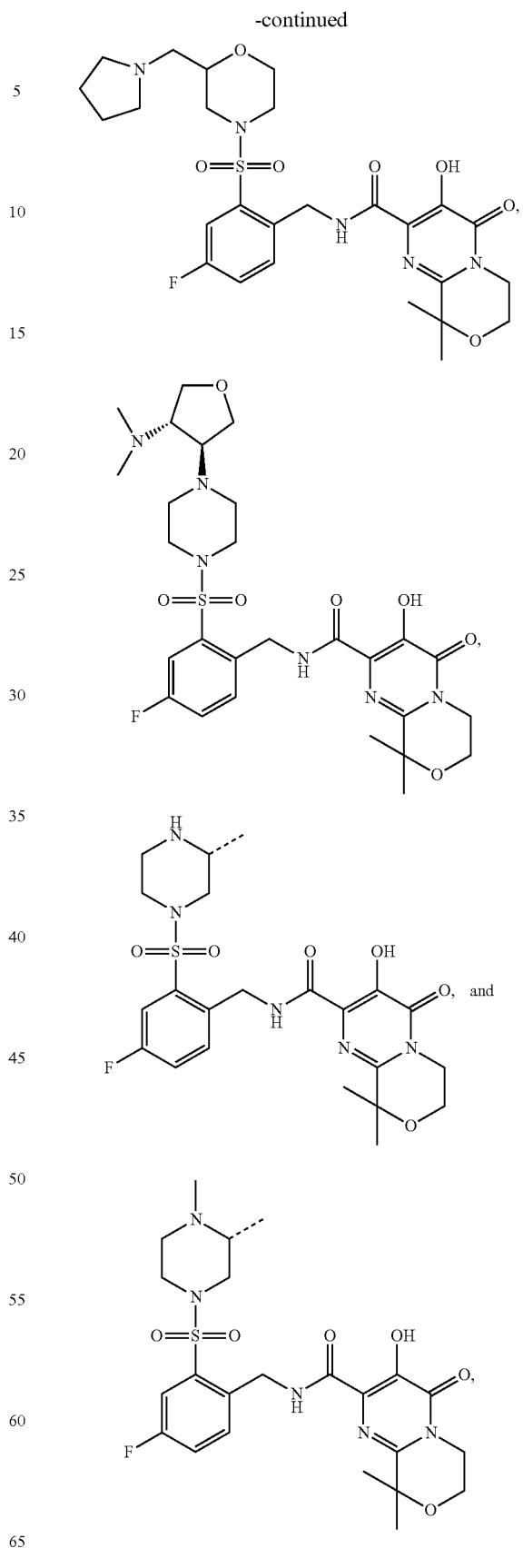
or a pharmaceutically acceptable salt thereof.

8. A composition comprising a therapeutic amount of a compound of claim 1 and a pharmaceutically acceptable carrier.

9. A method for treating HIV infection comprising administering a therapeutically effective amount of a compound of claim 1, or a pharmaceutically acceptable salt or solvate thereof, to a patient in need thereof.

* * * * *

UNITED STATES PATENT AND TRADEMARK OFFICE
CERTIFICATE OF CORRECTION

PATENT NO. : 7,902,182 B2  Page 1 of 1
APPLICATION NO. : 11/595429
DATED : March 8, 2011
INVENTOR(S) : B. Narasimhulu Naidu et al.

It is certified that error appears in the above-identified patent and that said Letters Patent is hereby corrected as shown below:

In the Claims:

Claim 1:

Column 111, lines 47 and 48, change "dialklyamino" to -- dialkylamino --.

Claim 7:

Column 115, lines 26 to 39, change

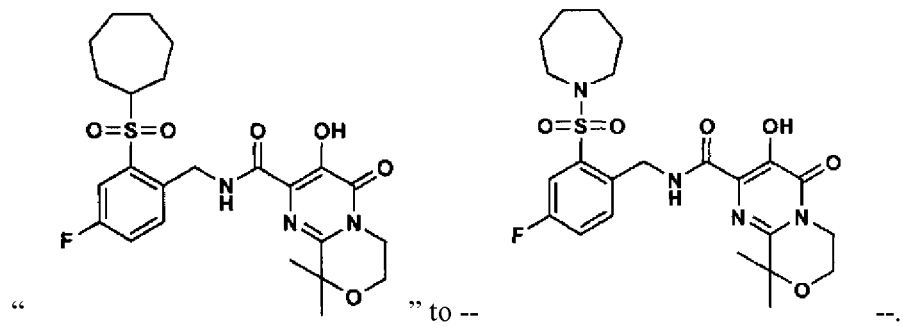

Column 116, lines 51 to 66, change

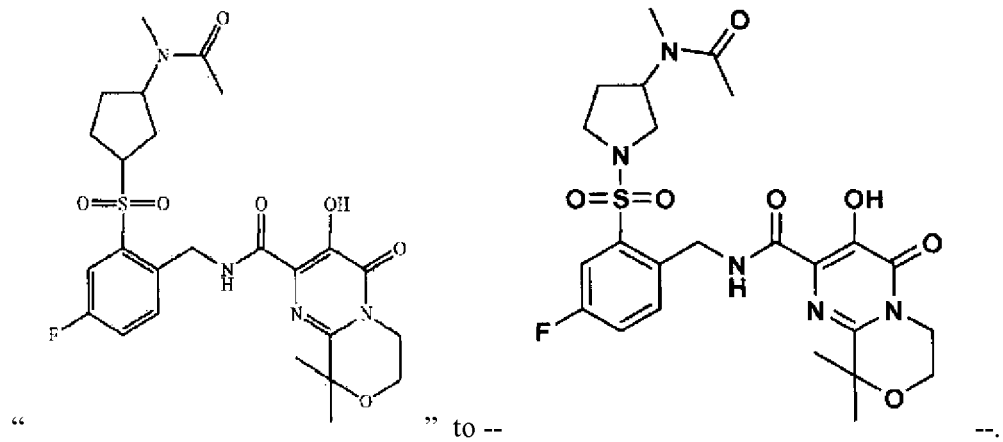

Signed and Sealed this
Sixth Day of December, 2011

David J. Kappos
*Director of the United States Patent and Trademark Office*